(12) United States Patent
Imbriglio et al.

(10) Patent No.: US 9,877,957 B2
(45) Date of Patent: Jan. 30, 2018

(54) TETRAHYDROISOQUINOLINE DERIVATIVES USEFUL AS INHIBITORS OF DIACYLGLYCERIDE O-ACYLTRANSFERASE 2

(71) Applicant: Merck Sharp & Dohme Corp., Rahway, NJ (US)

(72) Inventors: Jason Imbriglio, Piscataway, NJ (US); Clare London, Chatham, NJ (US); Zhijian Lu, Plainfield, IN (US); James Tata, Westfield, NJ (US); Yusheng Xiong, Plainsboro, NJ (US); Ming You, Monroe, NJ (US); Hyewon Youm, Berkeley Heights, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/508,557

(22) PCT Filed: Aug. 31, 2015

(86) PCT No.: PCT/US2015/047655
§ 371 (c)(1),
(2) Date: Mar. 3, 2017

(87) PCT Pub. No.: WO2016/036636
PCT Pub. Date: Mar. 10, 2016

(65) Prior Publication Data
US 2017/0273966 A1 Sep. 28, 2017

Related U.S. Application Data

(60) Provisional application No. 62/046,234, filed on Sep. 5, 2014.

(51) Int. Cl.
| | | |
|---|---|---|
| C07D 217/06 | (2006.01) |
| A61K 31/47 | (2006.01) |
| C07C 13/04 | (2006.01) |
| A61K 31/16 | (2006.01) |
| C07D 417/12 | (2006.01) |

(52) U.S. Cl.
CPC .............. *A61K 31/47* (2013.01); *A61K 31/16* (2013.01); *C07C 13/04* (2013.01); *C07D 217/06* (2013.01); *C07D 417/12* (2013.01)

(58) Field of Classification Search
CPC .... C07D 217/06; C07D 417/12; C07C 13/04; A61K 31/16; A61K 31/47
See application file for complete search history.

(56) References Cited

U.S. PATENT DOCUMENTS

2006/0189606 A1 8/2006 Karp et al.
2008/0004272 A1 1/2008 Vohra et al.
2009/0253740 A1 10/2009 Kawashima et al.
2012/0022057 A1 1/2012 Zhou et al.
2012/0202847 A1 8/2012 Uto et al.
2014/0080788 A1 3/2014 Robl et al.

FOREIGN PATENT DOCUMENTS

| WO | 2003053363 | 7/2003 |
| WO | 2006019831 | 2/2006 |
| WO | 2006117314 | 11/2006 |
| WO | 2007084413 | 7/2007 |
| WO | 2007084435 | 7/2007 |
| WO | 2008015125 | 2/2008 |
| WO | 2008088692 | 7/2008 |

(Continued)

OTHER PUBLICATIONS

Choi et al., Suppression of Diacylglycerol Acyltransferase-2 (DGAT2), but Not DGAT1, with Antisense Oligonucleotides Reverses Diet-induced Hepatic Steatosis and Insulin Resistance, Journal of Biological Chemistry, 2007, 22678-22688, 282(31).
Hubbard et al., Antisense and small-molecule modulation of diacylglycerol acyltransferase, Expert Opinion on Therapeutic Patents, 2007, 1331-1339, 17(11).
Levin et al., Increased lipid accumulation and insulin resistance in transgenic mice expressing DGAT2 in glycolytic (type II) muscle, American Journal of Physiology, 2007, E1772-E1781, 293.

(Continued)

*Primary Examiner* — D M Seaman
(74) *Attorney, Agent, or Firm* — Sarah Hooson; Catherine D. Fitch

(57) ABSTRACT

The present invention relates to a compound represented by formula I: and pharmaceutically acceptable salts thereof. The compounds of formula I are inhibitors of diacylglyceride O-acyltransferase 2 ("DGAT2") and may be useful in the treatment, prevention and suppression of diseases mediated by DGAT2. The compounds of the present invention may be useful in the treatment of hepatic steatosis, diabetes mellitus, obesity, hyperlipidemia, hypercholesterolemia, atherosclerosis, cardio renal diseases such as chronic kidney diseases and heart failure and related diseases and conditions.

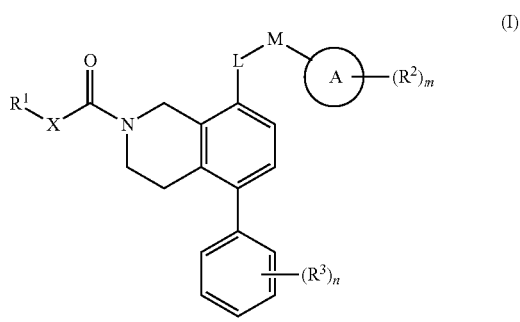

16 Claims, No Drawings

(56) References Cited

FOREIGN PATENT DOCUMENTS

| WO | 2009058298 | | 5/2009 |
|---|---|---|---|
| WO | 2009058299 | | 5/2009 |
| WO | 2010051188 | | 5/2010 |
| WO | 2010107765 | | 9/2010 |
| WO | 2010111058 | | 9/2010 |
| WO | 2010111059 | | 9/2010 |
| WO | 2010111060 | | 9/2010 |
| WO | 2010118009 | | 10/2010 |
| WO | 2016/036633 | * | 3/2016 |
| WO | 2016036633 | | 3/2016 |
| WO | 2016036638 | | 3/2016 |
| WO | 2016187384 | | 11/2016 |

OTHER PUBLICATIONS

Liu et al., Knockdown of Acyl-CoA:diacylglycerol acyltransferase 2 with antisense oligonucleotide reduces VLDL TG and ApoB secretion in mice, Biochimica et Biophysics Acta, Molecular and Cell Biology of Lipids, 2008, 97-104, 1781 (3).

Monetti et al., Dissociation of Hepatic Steatosis and Insulin Resistance in Mice Overexpressing DGAT in the Liver, Cell Metabolism, 2007, 69-78, 6(1).

Stone et al., The Endoplasmic Reticulum Enzyme DGAT2 is Found in Mitochondria-associated Membranes and has a Mitochondrial Targeting Signal That Promotes its Association with Mitochondria, Journal of Biological Chemistry, 2009, 5352-5361, 284(8).

* cited by examiner

TETRAHYDROISOQUINOLINE DERIVATIVES USEFUL AS INHIBITORS OF DIACYLGLYCERIDE O-ACYLTRANSFERASE 2

CROSS-REFERENCE TO RELATED APPLICATIONS

This application is a U.S. National Phase application under 35 U.S.C. §371 of PCT/US2015/047655, filed Aug. 31, 2015, which published as WO2016/036636 on Mar. 10, 2016, which claims priority from U.S. provisional application 62/046,234 filed Sep. 5, 2014.

FIELD OF THE INVENTION

The present invention is directed to tetrahydroisoquinoline derivative compounds which inhibit diacylglyceride O-acyltransferase 2 ("DGAT2"), and their use for preventing, treating or acting as a remedial agent for hepatic steatosis, type-2 diabetic mellitus, obesity, hyperlipidemia, hypercholesterolemia, atherosclerosis, cardio-renal diseases such as chronic kidney diseases and heart failure, and related diseases and conditions, as well as pharmaceutical compositions comprising such a compound and a pharmaceutical carrier.

BACKGROUND OF THE INVENTION

Triacylglycerols ("TGs") serve several functions in living organisms. One such function of TGs is in the storage of energy. TGs also play a role in the synthesis of membrane lipids. TG synthesis in cells may protect them from the potentially toxic effects of excess fatty acid ("FA"). In enterocytes and hepatocytes, TGs are synthesized for the assembly and secretion of lipoproteins which transport FA between tissues. TGs play a role in the skin's surface water barrier, and TGs in adipose tissue provide insulation for organisms.

The glycerol phosphate and the monoacylglycerol pathways are the major pathways for the biosynthesis of TG. However, the last step in the synthesis of TG involves the reaction of a fatty acyl-CoA and diacylglycerol ("DG") to form TG. The reaction is catalyzed by acyl-CoA:diacylglycerol acyltransferase ("DGAT") enzymes. There have been identified two DGAT enzymes, DGAT1 and DGAT2. Although DGAT1 and DGAT2 catalyze the same reaction, they differ significantly at the level of DNA and protein sequences.

DGAT2 is an integral membrane protein of the endoplasmic reticulum ("ER") and is expressed strongly in adipose tissue and the liver. DGAT2 appears to be the dominant DGAT enzyme controlling TG homeostasis in vivo. DGAT2 deficient mice survive for only a few hours after birth. On the other hand, DGAT1 deficient mice are viable.

In a study, DGAT2 knockdown in ob/ob mice with a DGAT2 gene-specific antisense oligonucleotide resulted in a dose dependent decrease in very low density lipoprotein ("VLDL") and a reduction in plasma TG, total cholesterol, and ApoB. Liu, et al., *Biochim. Biophys Acta* 2008, 1781, 97. In the same study, DGAT2 antisense oligonucleotide treatment of ob/ob mice showed a decrease in weight gain, adipose weight and hepatic TG content. Id. In another study, antisense treatment of ob/ob mice improved hepatic steatosis and hyperlipidemia. Yu, et al., *Hepatology*, 2005, 42, 362. In another study, diet-induced hepatic steatosis and insulin resistance was improved by knocking down DGAT2 in rats. Choi et al., *J. Bio. Chem.*, 2007, 282, 22678.

In light of the above description, inhibitors of DGAT2 are considered useful as agents for treating and/or preventing hepatic steatosis, diabetes mellitus, obesity, hyperlipidemia, hypercholesterolemia, atherosclerosis, cardio renal diseases such as chronic kidney diseases and heart failure and related diseases and conditions.

SUMMARY OF THE INVENTION

The present invention relates to compounds represented by formula I:

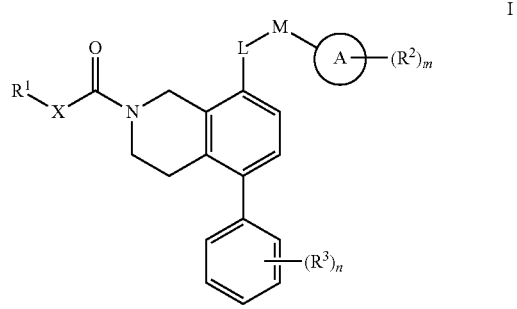

as well as pharmaceutically acceptable salts thereof, and pharmaceutical compositions comprising a compound of formula I.

The present invention further relates to methods of treating hepatic steatosis, diabetes mellitus, obesity, hyperlipidemia, hypercholesterolemia, atherosclerosis, cardio renal diseases such as chronic kidney diseases and heart failure and related diseases and conditions, comprising administering a compound of formula I to a patient in need thereof.

DETAILED DESCRIPTION OF THE INVENTION

The present invention is directed to compounds having structural Formula I:

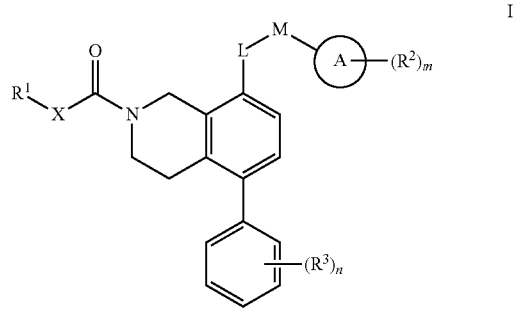

or a pharmaceutically acceptable salt thereof wherein:
L is
  (1) —$CH_2$—, or
  (2) —C(O)—;
M is
  (1) —N($R^4$)—,
  (2) *—N($R^4$)—($C_{1-3}$)alkylene wherein the alkylene is unsubstituted or substituted by ($C_{1-3}$)alkyl, hydroxy ($C_{1-3}$)alkyl, or morpholinyl, (3) *—N(R⁴)—C(O)—,
(4) *—N(R⁴)—C(O)-heterocyclyl-, wherein the heterocyclyl is a 4- to 6-membered monocyclic ring containing 1-2 heteroatoms selected from the group consisting of N, O, and S,
(5) *—N(R⁴)—(C₃₋₆)cycloalkyl-,
(6) *—N(R⁴)—(C₁₋₂)alkyl-(C₃₋₆)cycloalkyl-, or
(7)

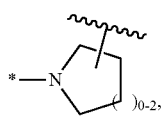

wherein * indicates the point of attachment to group L;
X is
   (1) —O—, or
   (2) —NH—;
R¹ is
   (1) (C₁₋₆)alkyl,
   (2) halo(C₁₋₈)alkyl, or
   (3) (C₃₋₆)cycloalkyl-;
ring A is
   (1) 4- to 6-membered heterocyclyl containing 1-2 heteroatoms selected from the group consisting of N, O, and S,
   (2) aryl,
   (3) fused phenyl,
   (4) 5- or 6-membered heteroaryl containing 1-4 heteroatoms selected from the group consisting of N, O, and S, or
   (5) fused 8- to 10-membered heteroaryl containing 1-4 heteroatoms selected from the group consisting of N, O, and S;
R² is
   (1) (C₁₋₆)alkyl,
   (2) halo(C₁₋₆)alkyl,
   (3) (C₁₋₆)alkoxy,
   (4) halo(C₁₋₆)alkoxy,
   (5) cyano,
   (6) aryl,
   (7) 5- or 6-membered heteroaryl containing 1-4 heteroatoms selected from the group consisting of N, O, or S,
   (8) fused 8- to 10-membered heteroaryl containing 1-4 heteroatoms selected from the group consisting of N, O, and S,
   (9) oxo,
   (10) (C₃₋₆)cycloalkyl, or
   (11) halo;
R³ is
   (1) (C₁₋₆)alkyl,
   (2) halo(C₁₋₆)alkyl,
   (3) (C₁₋₆)alkoxy,
   (4) halo(C₁₋₆)alkoxy,
   (5) —CO₂(C₁₋₆)alkyl,
   (6) halo, or
   (7) hydroxy;
R⁴ is
   (1) hydrogen, or
   (2) (C₁₋₃)alkyl;
m is 0, 1, 2, or 3; and
n is 0, 1 or 2.

In one embodiment, L is —CH₂—. In one class of this embodiment, M is *—N(R⁴)—C(O)—, or *—N(R⁴)—C(O)-heterocyclyl, wherein the heterocyclyl is a 5- to 6-membered monocyclic ring containing 1-2 heteroatoms selected from the group consisting of N, O, and S; wherein * indicates the point of attachment to group L. In one subclass of this class, X is —NH—. In one sub-subclass of this subclass, R¹ is (C₁₋₆)alkyl or halo(C₁₋₆)alkyl. In one sub-subclass of this subclass, R¹ is —(C₃₋₆)cycloalkyl-. In one sub-subclass of this subclass, R¹ is (C₁₋₆)alkyl. In one sub-subclass of this subclass, R¹ is halo(C₁₋₆)alkyl.

In one embodiment, L is —C(O)—. In one class of this embodiment, M is —N(R⁴)—, *—N(R⁴)—(C₁₋₃)alkylene wherein the alkylene is unsubstituted or substituted by (C₁₋₃)alkyl, hydroxy(C₁₋₃)alkyl, or morpholinyl, *—N(R⁴)—(C₃₋₆)cycloalkyl-, *—N(R⁴)—(C₁₋₂)alkyl-(C₃₋₆)cycloalkyl-, or

wherein * indicates the point of attachment to group L. In one subclass of this class, X is —NH—. In one sub-subclass of this subclass, R¹ is (C₁₋₆)alkyl or halo(C₁₋₆)alkyl. In one sub-subclass of this subclass, R¹ is —(C₃₋₆)cycloalkyl-. In one sub-subclass of this subclass, R¹ is (C₁₋₆)alkyl. In one sub-subclass of this subclass, R¹ is halo(C₁₋₆)alkyl.

In one embodiment, ring A is 4- to 6-membered heterocyclyl containing 1-2 heteroatoms selected from the group consisting of N, O, and S or fused 8- to 10-membered heterocyclyl containing 1-4 heteroatoms selected from the group consisting of N, O, and S. In one class of this embodiment, ring A is 5- or 6-membered heterocyclyl containing 1-2 heteroatoms selected from the group consisting of N, O, and S.

In one embodiment, ring A is aryl or fused phenyl. In a class of this embodiment, L is —CH₂—, and X is —NH—. In a class of this embodiment, L is —C(O)—, and X is —NH—.

In one class of this embodiment, ring A is 1,2,3,4-tetrahydroquinolinyl. In a subclass of this class, L is —CH₂—, and X is —NH—. In a subclass of this class, L is —C(O)—, and X is —NH—.

In one embodiment, ring A is 5- or 6-membered heteroaryl containing 1-4 heteroatoms selected from the group consisting of N, O, and S or a fused 8- to 10-membered heteroaryl containing 1-4 heteroatoms selected from the group consisting of N, O, and S. In one class of this embodiment, L is —CH₂—. In one subclass of this class, X is —NH—. In one class of this embodiment, L is —C(O)—. In one subclass of this class, X is —NH—.

In one class of this embodiment, ring A is 5- or 6-membered heteroaryl containing 1-4 heteroatoms selected from the group consisting of N, O, and S. In one class of this embodiment, ring A is fused 8- to 10-membered heteroaryl containing 1-4 heteroatoms selected from the group consisting of N, O, and S.

In one embodiment, ring A is phenyl, 1,2,3,4-tetrahydroquinolinyl, pyrazolyl, isoquinolinyl, quinolinyl, imidazolyl, 1H-benzo[d]imidazolyl, imidazo[1,2-a]pyrimidinyl, imidazo[1,2-a]pyridinyl, benzo[c][1,2,5]oxadiazolyl, imidazo[2,1-b]thiazolyl, pyridinyl, 1,7-naphthyridinyl, imidazo[2,1-b][1,3,4]thiadiazolyl, isoxazolyl, 1,2,4-oxadiazolyl, isothiazolyl, pyrazolo[1,5-a]pyridinyl, 6,7-dihydro-5H-pyrrolo[2,1-c][1,2,4]triazolyl, 1H-benzo[d][1,2,3]triazolyl, 1,4,5,6-tetrahydrocyclopenta[c]pyrazolyl, 1H-1,2,3-triazolyl, pyrimidinyl, 1H-1,2,4-triazolyl, oxazolyl, or 1,2,5-oxadiazolyl. In a class of this embodiment, L is —CH$_2$—, and X is —NH—. In a class of this embodiment, L is —C(O)—, and X is —NH—.

In one class of this embodiment, ring A is phenyl or 1,2,3,4-tetrahydroquinolinyl. In a subclass of this class, L is —CH$_2$—, and X is —NH—. In a subclass of this class, L is —C(O)—, and X is —NH—.

In one class of this embodiment, ring A is phenyl. In a subclass of this class, L is —CH$_2$—, and X is —NH—. In a subclass of this class, L is —C(O)—, and X is —NH—.

In one class of this embodiment, ring A is a fused phenyl. In one subclass of this class, ring A is 1,2,3,4-tetrahydroquinolinyl. In a sub-subclass of this subclass, L is —CH$_2$—, and X is —NH—. In a sub-subclass of this subclass, L is —C(O)—, and X is —NH—.

In one class of this embodiment, ring A is pyrazolyl, isoquinolinyl, quinolinyl, imidazolyl, 1H-benzo[d]imidazolyl, imidazo[1,2-a]pyrimidinyl, imidazo[1,2-a]pyridinyl, benzo[c][1,2,5]oxadiazolyl, imidazo[2,1-b]thiazolyl, pyridinyl, 1,7-naphthyridinyl, imidazo[2,1-b][1,3,4]thiadiazolyl, isoxazolyl, 1,2,4-oxadiazolyl, isothiazolyl, pyrazolo[1,5-a]pyridinyl, 6,7-dihydro-5H-pyrrolo[2,1-c][1,2,4]triazolyl, 1H-benzo[d][1,2,3]triazolyl, 1,4,5,6-tetrahydrocyclopenta[c]pyrazolyl, 1H-1,2,3-triazolyl, pyrimidinyl, 1H-1,2,4-triazolyl, oxazolyl, or 1,2,5-oxadiazolyl.

In a subclass of this class, ring A is pyrazolyl, imidazolyl, pyridinyl, isoxazolyl, 1,2,4-oxadiazolyl, isothiazolyl, 1H-1,2,3-triazolyl, pyrimidinyl, 1H-1,2,4-triazolyl, oxazolyl, or 1,2,5-oxadiazolyl. In a sub-subclass of this subclass, L is —CH$_2$—, and X is —NH—. In a sub-subclass of this subclass, L is —C(O)—, and X is —NH—.

In a sub-subclass of this subclass, ring A is pyrazolyl. In a sub-subclass of this subclass, ring A is imidazolyl. In a sub-subclass of this subclass, ring A is pyridinyl. In a sub-subclass of this subclass, ring A is isoxazolyl. In a sub-subclass of this subclass, ring A is 1,2,4-oxadiazolyl. In a sub-subclass of this subclass, ring A is isothiazolyl. In a sub-subclass of this subclass, ring A is 1H-1,2,3-triazolyl. In a sub-subclass of this subclass, ring A is pyrimidinyl. In a sub-subclass of this subclass, ring A is 1H-1,2,4-triazolyl. In a sub-subclass of this subclass, ring A is oxazolyl. In a sub-subclass of this subclass, ring A is 1,2,5-oxadiazolyl.

In a subclass of this class, ring A is isoquinolinyl, quinolinyl, 1H-benzo[d]imidazolyl, imidazo[1,2-a]pyrimidinyl, imidazo[1,2-a]pyridinyl, benzo[c][1,2,5]oxadiazolyl, imidazo[2,1-b]thiazolyl, 1,7-naphthyridinyl, imidazo[2,1-b][1,3,4]thiadiazolyl, pyrazolo[1,5-a]pyridinyl, 6,7-dihydro-5H-pyrrolo[2,1-c][1,2,4]triazolyl, 1H-benzo[d][1,2,3]triazolyl, or 1,4,5,6-tetrahydrocyclopenta[c]pyrazolyl. In a sub-subclass of this subclass, L is —CH$_2$—. In a sub-subclass of this subclass, L is —C(O)—.

In a sub-subclass of this subclass, ring A is isoquinolinyl. In a sub-subclass of this subclass, ring A is quinolinyl. In a sub-subclass of this subclass, ring A is 1H-benzo[d]imidazolyl. In a sub-subclass of this subclass, ring A is imidazo[1,2-a]pyrimidinyl. In a sub-subclass of this subclass, ring A is imidazo[1,2-a]pyridinyl. In a sub-subclass of this subclass, ring A is benzo[c][1,2,5]oxadiazolyl. In a sub-subclass of this subclass, ring A is imidazo[2,1-b]thiazolyl. In a sub-subclass of this subclass, ring A is 1,7-naphthyridinyl. In a sub-subclass of this subclass, ring A is imidazo[2,1-b][1,3,4]thiadiazolyl. In a sub-subclass of this subclass, ring A is pyrazolo[1,5-a]pyridinyl. In a sub-subclass of this subclass, ring A is 6,7-dihydro-5H-pyrrolo[2,1-c][1,2,4]triazolyl. In a sub-subclass of this subclass, ring A is 1H-benzo[d][1,2,3]triazolyl. In a sub-subclass of this subclass, ring A is 1,4,5,6-tetrahydrocyclopenta[c]pyrazolyl.

In one embodiment, M is *—N(R$^4$)—C(O)—, and *N(R$^4$)—C(O)-heterocyclyl, wherein the heterocyclyl is a 5- to 6-membered monocyclic ring containing 1-2 heteroatoms selected from the group consisting of N, O, and S; wherein * indicates the point of attachment to group L. In one class of this embodiment, L is —C(O)—. In one class of this embodiment, M is

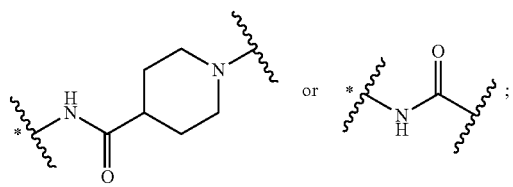 [SMILES: *NC(=O)C1CCN(*)CC1 ; *NC(*)=O]

wherein * indicates the point of attachment to group L. In one subclass of this class, L is —CH$_2$—.

In one embodiment, M is —N(R$^4$)—, *—N(R$^4$)—(C$_{1-3}$)alkylene wherein the alkylene is unsubstituted or substituted by (C$_{1-3}$)alkyl, hydroxy(C$_{1-3}$)alkyl, or morpholinyl, *—N(R$^4$)—(C$_{3-6}$)cycloalkyl-, *—N(R$^4$)—(C$_{1-2}$)alkyl-(C$_{3-6}$)cycloalkyl-, or

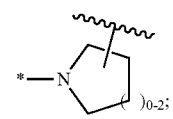

wherein * indicates the point of attachment to group L. In one class of this embodiment, L is —C(O)—.

In one class of this embodiment, M is

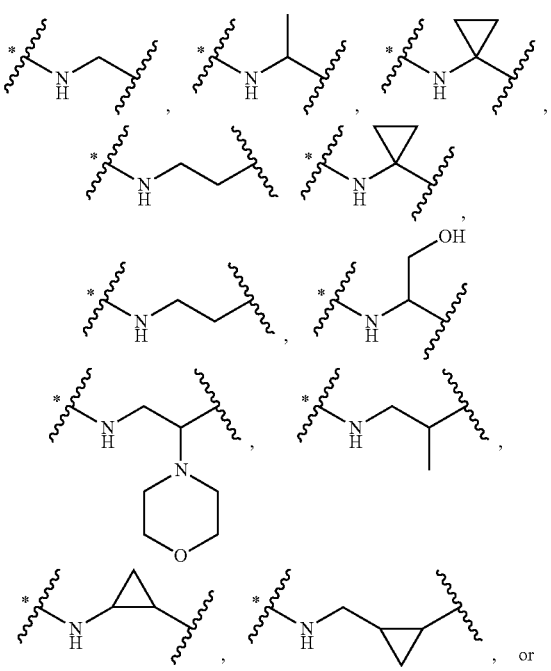

-continued

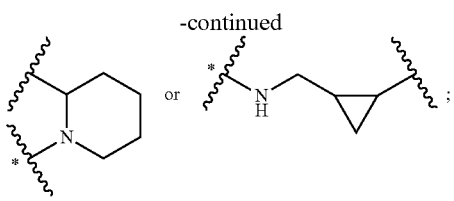

wherein * indicates the point of attachment to group L. In one subclass of this class, L is —C(O)—.

In one embodiment, M is

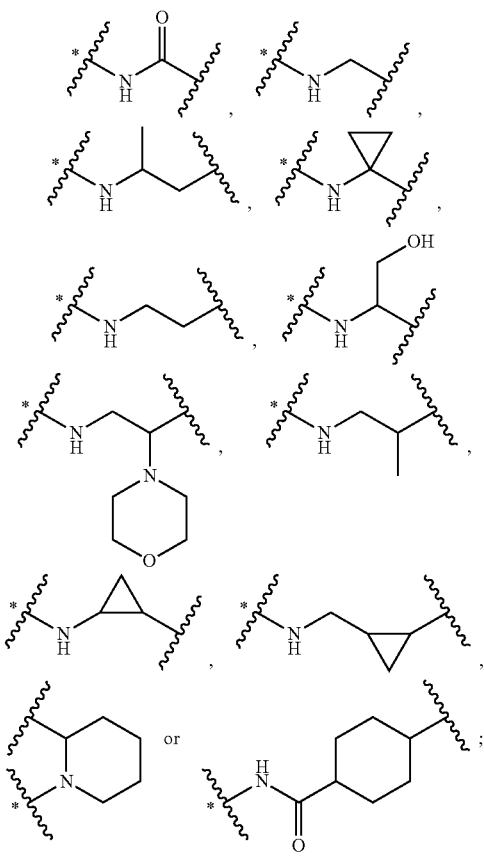

wherein * indicates the point of attachment to group L.

In one embodiment, $R^3$ is $(C_{1-6})$alkyl, halo$(C_{1-6})$alkyl, $(C_{1-6})$alkoxy, halo$(C_{1-6})$alkyl, or —CO$_2$(C$_{1-6}$)alkyl. In one class of this embodiment, $R^3$ is —COOMe, —OCH$_3$, —OCF$_3$, or —CF$_3$.

In particular embodiments, the present invention relates to:
- (R)—N$^2$-(tert-butyl)-N$^8$-(2-hydroxy-1-(6-(trifluoromethyl)pyridin-3-yl)ethyl)-5-(3-(trifluoromethyl)phenyl)-3,4-dihydroisoquinoline-2,8(1H)-dicarboxamide;
- N$^2$-(tert-butyl)-N$^8$-((1R)-2-phenylcyclopropyl)-5-(3-(trifluoromethyl)phenyl)-3,4-dihydroisoquinoline-2,8(1H)-dicarboxamide,
- N$^2$-(tert-butyl)-N$^8$-(((1R,2R)-2-phenylcyclopropyl)methyl)-5-(3-(trifluoromethyl)phenyl)-3,4-dihydroisoquinoline-2,8(1H)-dicarboxamide,
- N$^2$-(tert-butyl)-N$^8$-(imidazo[1,2-a]pyridin-3-ylmethyl)-5-(3-(trifluoromethyl)phenyl)-3,4-dihydroisoquinoline-2,8(1H)-dicarboxamide, or a pharmaceutically acceptable salt thereof.

In specific embodiments, the present invention relates to:
- (S)—N$^2$-(tert-butyl)-N$^8$-(2-hydroxy-1-(6-(trifluoromethyl)pyridin-3-yl)ethyl)-5-(3-(trifluoromethyl)phenyl)-3,4-dihydroisoquinoline-2,8(1H)-dicarboxamide,
- N$^2$-(tert-butyl)-N$^8$-((1S,2R)-2-phenylcyclopropyl)-5-(3-(trifluoromethyl)phenyl)-3,4-dihydroisoquinoline-2,8(1H)-dicarboxamide,
- N$^2$-(tert-butyl)-N$^8$-((1R,2S)-2-phenylcyclopropyl)-5-(3-(trifluoromethyl)phenyl)-3,4-dihydroisoquinoline-2,8(1H)-dicarboxamide,
- N2-(tert-butyl)-N8-(((1S,2S)-2-phenylcyclopropyl)methyl)-5-(3-(trifluoromethyl)phenyl)-3,4-dihydroisoquinoline-2,8(1H)-dicarboxamide, or a pharmaceutically acceptable salt thereof.

All structural Formulas, embodiments and classes thereof described herein include the pharmaceutically acceptable salts of the compounds defined therein. Reference to the compounds of structural Formula I includes the compounds of other generic structural Formulas and embodiments that fall within the scope of Formula I.

"Alkyl" means branched- and straight-chain saturated aliphatic hydrocarbon groups having the specified number of carbon atoms when noted. If no number is specified, 1-6 carbon atoms are intended for linear and 3-7 carbon atoms for branched alkyl groups. Examples of alkyl groups include methyl, ethyl, propyl, isopropyl, butyl, sec- and tert-butyl, pentyl, hexyl, octyl, nonyl, and the like.

"Alkoxy" refers to an alkyl group linked to oxygen. Examples of alkoxy group includes methoxy, ethoxy, propoxy and the like.

"Aryl" means phenyl or naphthyl.

"Fused Phenyl" means a phenyl ring fused with heterocyclyl or cycloalkyl. Fused phenyl can be a 9- or 10-membered ring system. Examples include 1,2,3,4-tetrahydronaphthalenyl, 1,2,3,4-tetrahydroquinolinyl, and indolinyl.

"Halogen" (halo) includes fluorine, chlorine, bromine and iodine.

"Cycloalkyl" means a saturated cyclic hydrocarbon radical having the number of carbon atoms designated. If no number of atoms is specified, 3-7 carbon atoms are intended. Cycloalkyl may be fused forming 1-3 carbocyclic rings. If no number of carbon atoms is specified, 4-11 carbon atoms are intended. Other variations may be used. Examples of cycloalkyl include cyclopropyl, cyclobutyl, cyclopentyl, cyclohexyl, cycloheptyl, tetrahydronaphthyl, decahydronaphthyl, indanyl and the like.

Alkyl and cycloalkyl are each intended to include such carbon moieties containing isotopic forms of hydrogen (H) such as protium ($^1$H), for example but not limited to —CH$_3$, and/or deuterium ($^2$H, also denoted herein as D), for example but not limited to —CD$_3$.

"Haloalkyl" and derivatives such as "halo(C$_{1-6}$)alkyl" include mono-substituted as well as multiple halo substituted alkyl groups, up to perhalo substituted alkyl. For example, trifluoromethyl is included.

"Haloalkoxy," "haloalkyl-O" and derivatives such as "halo(C$_{1-6}$)alkoxy" are used interchangeably and refer to halo substituted alkyl groups linked through the oxygen atom. Haloalkoxy include mono-substituted as well as multiple halo substituted alkoxy groups, up to perhalo substituted alkoxy. For example trifluoromethoxy is included.

"Heterocyclyl," "heterocycle" or "heterocyclic" refers to nonaromatic monocyclic ring structures in which one or more atoms in the ring, the heteroatom(s), is an element other than carbon. Heteroatoms are typically O, S or N atoms. Examples of heterocyclyl groups include: piperidine, piperazine, morpholine, pyrrolidine, tetrahydrofuran, azetidine, oxirane, or aziridine, and the like.

"Heteroaryl" unless otherwise indicated, means a monocyclic-aromatic ring or ring system, wherein the ring or ring system is made up of a specified number of atoms when noted, and which contains at least one heteroatom selected from O, S and N or a specified number and selection of heteroatoms when noted. Examples include, but are not limited to, pyrrolyl, isoxazolyl, isothiazolyl, pyrazolyl, pyridyl, oxazolyl, oxadiazolyl, 1,3,4-oxadiazolyl-2(3H)-one, thiadiazolyl, thiazolyl, imidazolyl, triazolyl, tetrazolyl, furanyl, triazinyl, thienyl, pyridinyl, pyrimidinyl, pyrimidyl, pyridazinyl, pyrazinyl, and the like.

"Fused heteroaryl" means a heteroaryl fused to an aryl, cycloalkyl, heterocyclyl, or another heteroaryl. Fused heteroaryl ring can be a 7-, 8-, 9-, 10, or 11-membered ring or combinations thereof. One such combination is from a 7- to 10 membered ring system. Examples include indole, 4,5,6,7-tetrahydro-1H-indole, 1H-benzo[d][1,2,3]triazole, benzo[d]isoxazole, and [1,2,4]triazolo[1,5-α]pyridine.

"Oxo" means an oxygen linked to an atom by a double bond. An example of an oxo group is a doubly bonded oxygen in a ketone, sulfoxide, sulfone and sulfate.

"Hydroxyalkyl" means an alkyl group having one or more hydrogen atoms replaced by hydroxyl groups.

When any variable (e.g., $R^2$, $R^3$, etc.) occurs more than one time in any constituent or in Formula I or other generic Formulae herein, its definition on each occurrence is independent of its definition at every other occurrence. Combinations of substituents and/or variables are permissible only if such combinations result in stable compounds. In choosing compounds of the present invention, one of ordinary skill in the art will recognize that the various substituents, i.e. $R^2$, $R^3$, etc., are to be chosen in conformity with well-known principles of chemical structure connectivity and stability. Unless expressly stated to the contrary, substitution by a named substituent is permitted on any atom in a ring (e.g., aryl, a heteroaryl ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Unless expressly depicted or described otherwise, variables depicted in a structural formula with a "floating" bond, such as $R^2$ and $R^3$, are permitted on any available carbon atom in the ring to which the variable is attached. When a moiety is noted as being "optionally substituted" in Formula I or any embodiment thereof, it means that Formula I or the embodiment thereof encompasses compounds that contain the noted substituent (or substituents) on the moiety and also compounds that do not contain the noted substituent (or substituents) on the moiety.

Compounds of structural Formula I may contain one or more asymmetric centers and can thus occur as racemates and racemic mixtures, single enantiomers, diastereoisomeric mixtures and individual diastereoisomers. Centers of asymmetry that are present in the compounds of Formula I can all independently of one another have S configuration or R configuration. The compounds of this invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The present invention is meant to comprehend all such stereo-isomeric forms of the compounds of structural Formula I.

Compounds of structural Formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration. Alternatively, any stereoisomer or isomers of a compound of Formula I may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

For compounds of Formula I described herein which contain olefinic double bonds, unless specified otherwise, they are meant to include both E and Z geometric isomers.

Some of the compounds described herein may exist as tautomers which have different points of attachment of hydrogen accompanied by one or more double bond shifts. For example, a ketone and its enol form are keto-enol tautomers. The individual tautomers as well as mixtures thereof are encompassed with compounds of Formula I of the present invention.

In the compounds of structural Formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention as described and claimed herein is meant to include all suitable isotopic variations of the compounds of structural Formula I and embodiments thereof. For example, different isotopic forms of hydrogen (H) include protium ($^1$H) and deuterium ($^2$H, also denoted herein as D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural Formula I, can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of structural Formula I are meant to also include the pharmaceutically acceptable salts thereof and also salts that are not pharmaceutically acceptable when they are used as precursors to the free compounds or their pharmaceutically acceptable salts or in other synthetic manipulations. The compounds of the present invention, including the compounds of the Examples, also includes all salts of the compounds of Formula I which, owing to low physiological compatibility, are not directly suitable for use in pharmaceuticals but which can be used, for example, as intermediates for chemical reactions or for the preparation of physiologically acceptable salts.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, benzenesulfonate, benzoate, bicarbonate, bisulfate, bitartrate, borate, bromide, butyrate, camphorate, camphorsulfonate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, methanesulfonate, mucate, napsylate, nitrate, N-methylglucamine ammonium salt, oleate, oxalate, pamoate (embonate), palmitate, pantothenate, phosphate/diphosphate, polygalacturonate, propionate, salicylate, stearate, sulfate, subacetate, succinate, tannate, tartrate, teoclate, thiocyanate, tosylate, triethiodide, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. In particular embodiments are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts.

Furthermore, compounds of the present invention may exist in amorphous form and/or one or more crystalline forms, and as such all amorphous and crystalline forms and mixtures thereof of the compounds of Formula I, including the Examples, are intended to be included within the scope of the present invention. In addition, some of the compounds of the instant invention may form solvates with water (i.e., a hydrate) or common organic solvents such as but not limited to ethyl acetate. Such solvates and hydrates, particularly the pharmaceutically acceptable solvates and hydrates, of the instant compounds are likewise encompassed within the scope of this invention, along with un-solvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid (—COOH) group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Included are those esters and acyl groups known in the art for modifying the solubility or hydrolysis characteristics for use as sustained-release or prodrug formulations. Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed.

Accordingly, the compounds within the generic structural formulas, embodiments and specific compounds described in the Examples and claimed herein encompass salts, all possible stereoisomers and tautomers, physical forms (e.g., amorphous and crystalline forms), solvate and hydrate forms thereof and any combination of these forms, as well as the salts, pro-drug forms thereof, and salts of pro-drug forms thereof, where such forms are possible unless specified otherwise.

The present invention also relates to processes for the preparation of the compounds of Formula I which are described in the following and by which the compounds of the invention are obtainable.

The terms "therapeutically effective (or efficacious) amount" and similar descriptions such as "an amount efficacious for treatment" are intended to mean that amount of a pharmaceutical drug that will elicit the biological or medical response of a tissue, a system, animal or human that is being sought by a researcher, veterinarian, medical doctor or other clinician. The terms "prophylactically effective (or efficacious) amount" and similar descriptions such as "an amount efficacious for prevention" are intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of hepatic steatosis, diabetes mellitus, obesity, hyperlipidemia, hypercholesterolemia, and a prophylactically effective amount, e.g., for prevention of atherosclerosis.

Disorders and pathological conditions which can be treated or prevented by inhibiting DGAT2 by using the compounds of Formula I are, for example, diseases such as hyperlipidemia, type I diabetes, type II diabetes mellitus, coronary heart disease, ischemic stroke, restenosis, peripheral vascular disease, intermittent claudication, myocardial infarction, dyslipidemia, post-prandial lipemia, obesity, osteoporosis, hypertension, congestive heart failure, left ventricular hypertrophy, peripheral arterial disease, diabetic retinopathy, diabetic nephropathy, glomerulosclerosis, chronic renal failure, diabetic neuropathy, metabolic syndrome, syndrome X, coronary heart disease, angina pectoris, thrombosis, atherosclerosis, myocardial infarction, transient ischemic attacks, stroke, hyperglycemia, hyperinsulinemia, hypertriglyceridemia, insulin resistance, impaired glucose tolerance, erectile dysfunction, skin and connective tissue disorders, hyper-apo B lipoproteinemia, non-alcoholic steatohepatitis (NASH), non-alcoholic fatty liver disease, cardiorenal diseases such as chronic kidney diseases and heart failure, and related diseases and conditions.

The compounds of Formula I and their pharmaceutically acceptable salts can be administered to animals, preferably to mammals, and in particular to humans, as pharmaceuticals by themselves, in mixtures with one another or in the form of pharmaceutical preparations. The term "patient" includes animals, preferably mammals and especially humans, who use the instant active agents for the prevention or treatment of a medical condition. Administering of the drug to the patient includes both self-administration and administration to the patient by another person. The patient may be in need of, or desire, treatment for an existing disease or medical condition, or may be in need of or desire prophylactic treatment to prevent or reduce the risk of occurrence of said disease or medical condition. As used herein, a patient "in need" of treatment of an existing condition or of prophylactic treatment encompasses both a determination of need by a medical professional as well as the desire of a patient for such treatment.

A therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment of hepatic steatosis, diabetes mellitus, obesity, hyperlipidemia, hypercholesterolemia, atherosclerosis, and cardiorenal diseases.

Furthermore, a subject of the present invention are pharmaceutical preparations (or pharmaceutical compositions) which comprise as active component a therapeutically effective dose of at least one compound of Formula I and/or a pharmaceutically acceptable salt thereof and a customary pharmaceutically acceptable carrier, i.e., one or more pharmaceutically acceptable carrier substances and/or additives.

Thus, a subject of the invention are, for example, said compound and its pharmaceutically acceptable salts for use as a pharmaceutical, pharmaceutical preparations which comprise as active component a therapeutically effective dose of said compound and/or a pharmaceutically acceptable salt thereof and a customary pharmaceutically acceptable carrier, and the uses of said compound and/or a pharmaceutically acceptable salt thereof in the therapy or prophylaxis of the above mentioned syndromes as well as their use for preparing medicaments for these purposes.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of Formula I and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical preparations can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the active compound of Formula I and/or of a pharmaceutically acceptable salt thereof to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I.

One or more additional pharmacologically active agents may be administered in combination with a compound of Formula I. An additional active agent (or agents) is intended to mean a pharmaceutically active agent (or agents) that is active in the body, including pro-drugs that convert to pharmaceutically active form after administration, which are different from the compound of Formula I, and also includes free-acid, free-base and pharmaceutically acceptable salts of said additional active agents. Generally, any suitable additional active agent or agents, including but not limited to anti-hypertensive agents, anti-atherosclerotic agents such as a lipid modifying compound, anti-diabetic agents and/or antiobesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents).

Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan i.e., COZAAR®, valsartan, candesartan, olmesartan, telmesartan and any of these drugs used in combination with hydrochlorothiazide such as HYZAAR®); neutral endopeptidase inhibitors (e.g., thiorphan and phosphoramidon), aldosterone antagonists, aldosterone synthase inhibitors, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, phosphodiesterase-5 inhibitors (e.g. sildenafil, tadalfil and vardenafil), vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine); lipid lowering agents e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®) and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and/or with an HMG-CoA reductase inhibitor; niacin receptor agonists such as acipimox and acifran, as well as niacin receptor partial agonists; metabolic altering agents including insulin and insulin mimetics (e.g., insulin degludec, insulin glargine, insulin lispro), dipeptidyl peptidase-IV (DPP-4) inhibitors (e.g., sitagliptin, alogliptin, omarigliptin, linagliptin, vildagliptin); insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814); insulin or insulin analogs (e.g., insulin detemir, insulin glulisine, insulin degludec, insulin glargine, insulin lispro and inhalable formulations of each); leptin and leptin derivatives and agonists; amylin and amylin analogs (e.g., pramlintide); sulfonylurea and non-sulfonylurea insulin secretagogues (e.g., tolbutamide, glyburide, glipizide, glimepiride, mitiglinide, meglitinides, nateglinide and repaglinide); α-glucosidase inhibitors (e.g., acarbose, voglibose and miglitol); glucagon receptor antagonists (e.g., MK-3577, MK-0893, LY-2409021 and KT6-971); incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof); LDL cholesterol lowering agents such as (i) HMG-CoA reductase inhibitors (e.g., simvastatin, lovastatin, pravastatin, cerivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA:cholesterol acyltransferase inhibitors, (e.g., avasimibe); HDL-raising drugs, (e.g., niacin and nicotinic acid receptor agonists, and extended-release versions thereof; MK-524A, which is a combination of niacin extended-release and the DP-1 antagonist MK-524); antiobesity compounds; agents intended for use in inflammatory conditions, such as aspirin, non-steroidal anti-inflammatory drugs or NSAIDs, glucocorticoids, and selective cyclooxygenase-2 or COX-2 inhibitors; glucokinase activators (GKAs) (e.g., AZD6370); inhibitors of 11β-hydroxysteroid dehydrogenase type 1, (e.g., such as those disclosed in U.S. Pat. No. 6,730,690, and LY-2523199); CETP inhibitors (e.g., anacetrapib, and torcetrapib); inhibitors of fructose 1,6-bisphosphatase, (e.g., such as those disclosed in U.S. Pat. Nos. 6,054,587; 6,110,903; 6,284,748; 6,399,782; and 6,489,476); inhibitors of acetyl CoA carboxylase-1 or 2 (ACC1 or ACC2); AMP-activated Protein Kinase (AMPK) activators; other agonists of the G-protein-coupled receptors: (i) GPR-109, (ii) GPR-119 (e.g., MBX2982 and PSN821), and (iii) GPR-40 (e.g., TAK875); SSTR3 antagonists (e.g., such as those disclosed in WO 2009/001836); neuromedin U receptor agonists (e.g., such as those disclosed in WO 2009/042053, including, but not limited to, neuromedin S (NMS)); SCD modulators; GPR-105 antagonists (e.g., such as those disclosed in WO 2009/000087); SGLT inhibitors (e.g., ASP1941, SGLT-3, empagliflozin, dapagliflozin, canagliflozin, BI-10773, PF-04971729, remogliflozin, TS-071, tofogliflozin, ipragliflozin, and LX-4211); inhibitors of acyl coenzyme A: diacylglycerol acyltransferase 1 and 2 (DGAT-1 and DGAT-2); inhibitors of fatty acid synthase; inhibitors of acyl coenzyme A: monoacylglycerol acyltransferase 1 and 2 (MGAT-1 and MGAT-2); agonists of the TGR5 receptor (also known as GPBAR1, BG37, GPCR19, GPR131, and M-BAR); ileal bile acid transporter inhibitors; PACAP, PACAP mimetics, and PACAP receptor 3 agonists; PPAR agonists; protein tyrosine phosphatase-1B (PTP-1B) inhibitors; IL-1b antibodies, (e.g., XOMA052 and canakinumab); and bromocriptine mesylate and rapid-release formulations thereof; or with other drugs beneficial for the prevention or the treatment of the above-mentioned diseases including nitroprusside and diazoxide the free-acid, free-base, and pharmaceutically acceptable salt forms of the above active agents where chemically possible.

The following examples are provided so that the invention might be more fully understood. Unless otherwise indicated, the starting materials are commercially available. They should not be construed as limiting the invention in any way. A representative structure is provided for each mixture of isomers in the Examples. For each mixture of isomers, every isomer therein forms a specific embodiment of the present invention. Where a mixture of 4 isomers is specified, an additional embodiment encompasses a mixture of the 2 trans isomers.

Several methods for preparing the compounds of this invention are described in the following Schemes and Examples. Starting materials and intermediates are purchased, made from known procedures, or as otherwise illustrated. Some frequently applied routes to the compounds of Formula I are also described by the Schemes as follows. In some cases the order of carrying out the steps of reaction schemes may be varied to facilitate the reaction or to avoid unwanted reaction products. The "R" groups in the Schemes correspond to the variables defined in Formula I at the same positions on the structures.

1. General Synthetic Schemes

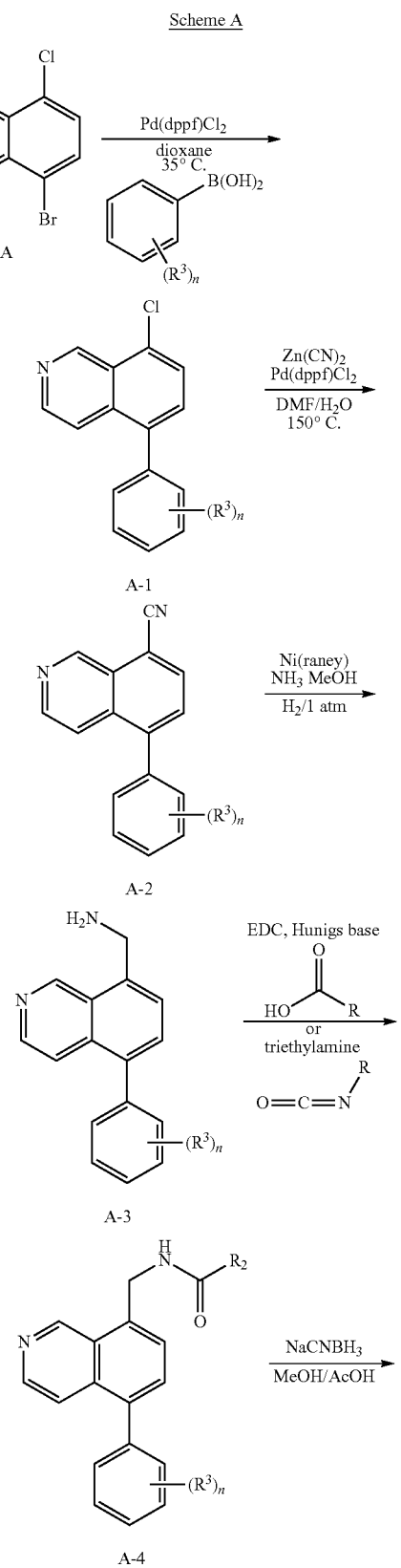

-continued

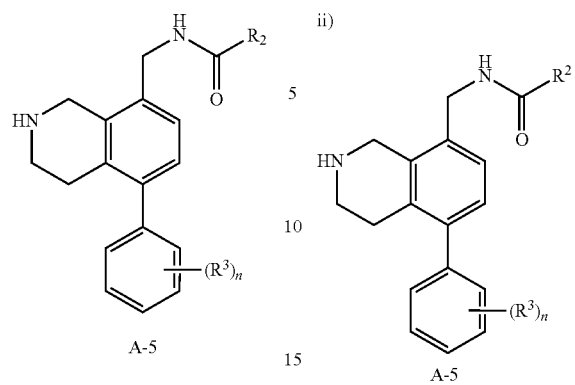

A-5

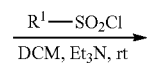

Compounds of structure A-5 can be prepared by treating the commercially available isoquinoline derivative A with Pd(dppf)Cl$_2$ and the corresponding boronic acid and heating in dioxane at 35° C. to afford A-1. The isoquinoline A-1 can be cynanated with Zn(CN)$_2$ and Pd(dppf)Cl$_2$ in mixed solvent at 150° C. to yield A-2. The cyanide is reduced to the amine under conditions of Raney nickel in ammonia methanol (7M) under an atmosphere of hydrogen to provide the amine A-3. The amide A-4 is provided via treatment of A-3 with EDC in Hunigs base and the corresponding acid, while the urea is afforded from treatment of A-3 with the corresponding isocynate in triethylamine. The tetrahydroisoquinoline A-5 is prepared through reduction of A-4 with sodium cyanoborohydride in mixed solvent of methanol and acetic acid.

Scheme B

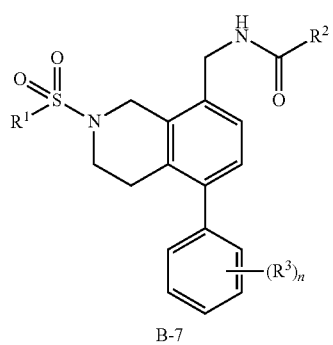

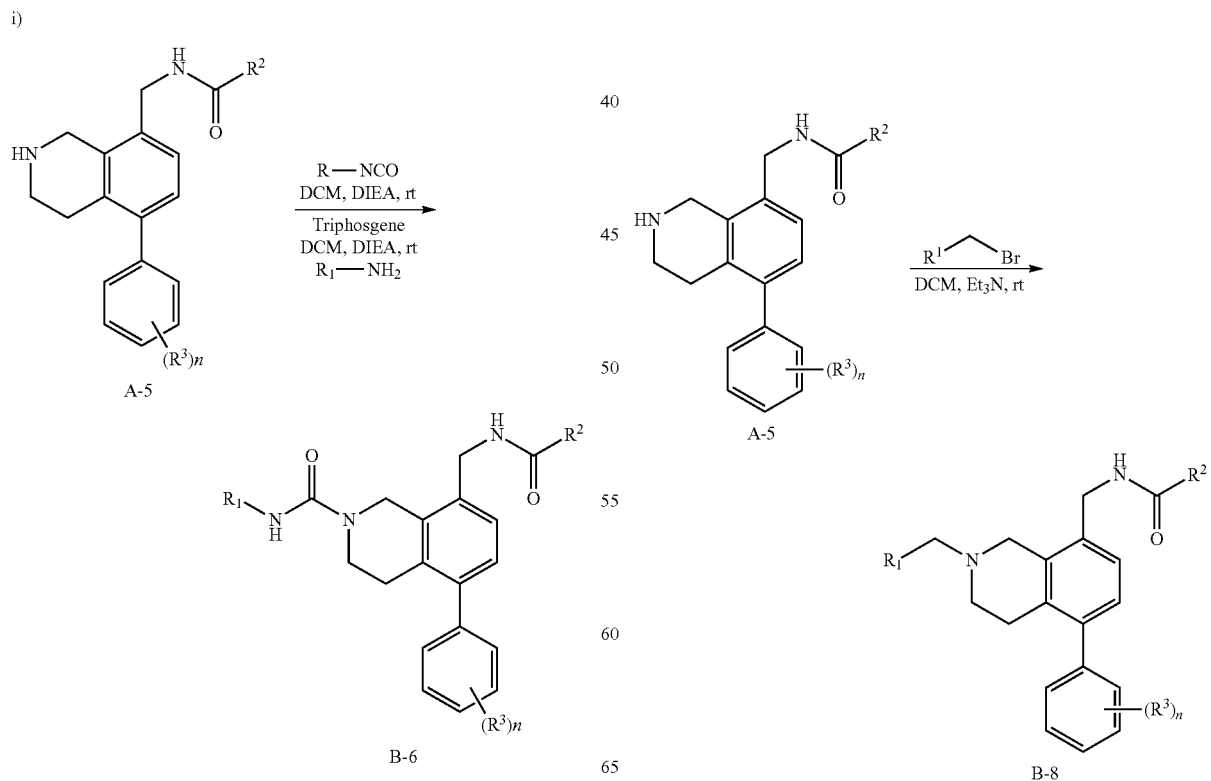

-continued iv)

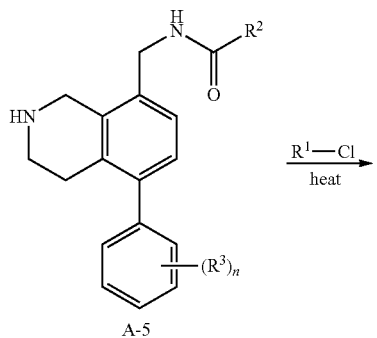

A-5

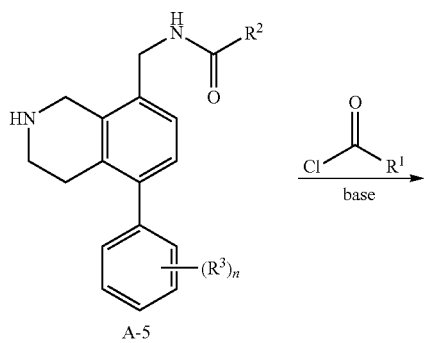

A-5

B-10

Compounds of structure B-6 to B-10 can be prepared via treatment of intermediate A-5 with either i) an isocyanate in the presence of base or a chloroformate in base followed by an amine to afford products such as B-6 ii) a sulfonyl chloride in base to yield sulfonylamides B-7 iii) an alkyl halide in base to afford products such as B-8, iv) the corresponding aryl chloride under thermal conditions to afford compounds such as B-9, or v) the corresponding carboxylic acid chloride in the presence of base to afford amides such as B-10.

Scheme C

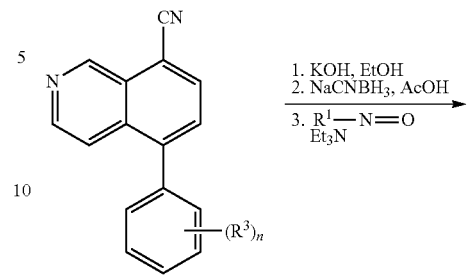

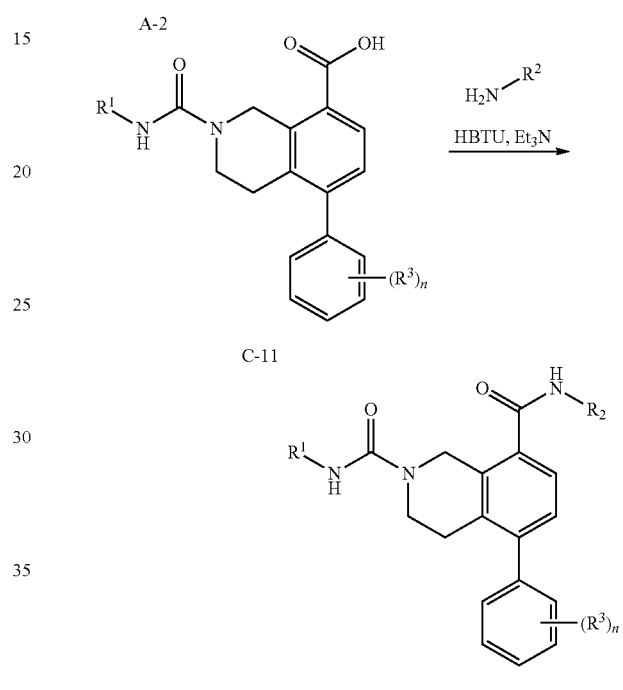

Compounds of the structure C-12 can be prepared by first converting the cyanide A-2 to the acid by treatment with potassium hydroxide. The resulting acid is then treated by sodium cyanoborohydride followed by treatment with $R^1$—N=O to yield the substituted tetrahydroisoquinoline C-11. The treatment of C-11 with HBTU in the presence of base and the desired amine results in the desired amide analog(s) C-12.

The invention will now be illustrated by the following non-limiting examples in which, unless stated otherwise:
(i) all operations were carried out at room or ambient temperature, that is, at a temperature in the range 18-25° C.;
(ii) evaporation of solvent was carried out using a rotary evaporator under reduced pressure (600-4000 Pascals) with a bath temperature of up to 50° C.;
(iii) the course of reactions was followed by thin layer chromatography (TLC) and/or tandem high performance liquid chromatography (HPLC) followed by mass spectroscopy (MS), herein termed LCMS, and any reaction times are given for illustration only;
(iv) the structure of all final compounds was assured by at least one of the following techniques: MS or proton nuclear magnetic resonance ($^1$H NMR) spectrometry, and the purity was assured by at least one of the following techniques: TLC or HPLC;

(v) yields, if given, are for illustration only;
(vi) ¹H NMR spectra were recorded on either a Varian Unity or a Varian Inova instrument at 500 or 600 MHz using the indicated solvent; when line-listed, NMR data is in the form of delta (δ) values for major diagnostic protons, given in parts per million (ppm) relative to residual solvent peaks (multiplicity and number of hydrogens); conventional abbreviations used for signal shape are: s. singlet; d. doublet (apparent); t. triplet (apparent); m. multiplet; br. broad; etc.;
(vii) MS data were recorded on a Waters Micromass unit, interfaced with a Hewlett-Packard (Agilent 1100) HPLC instrument, and operating on MASSLYNX/ OpenLynx software; electrospray ionization was used with positive (ES+) or negative ion (ES−) detection; the method for LCMS ES+ was 1-2 mL/min, 10-95% B linear gradient over 5.5 min (B=0.05% TFA-acetonitrile, A=0.05% TFA-water), and the method for LCMS ES− was 1-2 mL/min, 10-95% B linear gradient over 5.5 min (B=0.1% formic acid-acetonitrile, A=0.1% formic acid-water), Waters XTerra C18—3.5 μm—50× 3.0 mmID and diode array detection;
(viii) the purification of compounds by preparative reverse phase HPLC (RPHPLC) was conducted on either a Waters Symmetry Prep C18—5 μm—30×100 mmID, or a Waters Atlantis Prep dC18—5 μm—20× 100 mmID; 20 mL/min, 10-100% B linear gradient over 15 min (B=0.05% TFA-acetonitrile, A=0.05% TFA-water), and diode array detection;
(ix) the automated purification of compounds by preparative reverse phase HPLC was performed on a Gilson system using a YMC-Pack Pro C18 column (150×20 mm i.d.) eluting at 20 mL/min with 0-50% acetonitrile in water (0.1% TFA);
(x) the purification of compounds by preparative thin layer chromatography (PTLC) was conducted on 20×20 cm glass prep plates coated with silica gel, commercially available from Analtech;
(xi) chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq or equiv (equivalent(s)), $IC_{50}$ (molar concentration which results in 50% of maximum possible inhibition), $EC_{50}$ (molar concentration which produces 50% of the maximum possible efficacy or response), μM (micromolar), nM (nanomolar), dichloromethane (DCM), diethylisopropylamine (DIEA or Hunig's base), room temperature (rt), O-Benzotriazole-N,N,N',N'-tetramethyl-uronium-hexafluoro-phosphate (HBTU), tetrahydrofuran (THF), N-Methyl-2-pyrrolidone (NMP), dimethylsulfoxide (DMSO), diatomaceous earth (CELITE), hydroxybenzotriazole (HOBT), 1-ethyl-3-(3-dimethylaminopropyl)carbodiimide (EDC).

The following examples are provided so that the invention might be more fully understood. They should not be construed as limiting the invention in any way. The preparation of Intermediates and examples is described below:

INTERMEDIATES

Intermediate 1

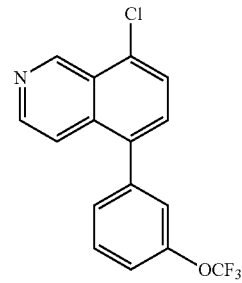 [SMILES: FC(F)(F)Oc1cccc(-c2ccc(Cl)c3cnccc23)c1]

8-chloro-5-(3-(trifluoromethoxy)phenyl)isoquinoline

To a solution of 8-chloro-5-bromo-isoquinoline (1 g, 4.12 mmol) in 20 ml DMF and 2 ml water, under nitrogen, was added 3-(trifluoromethoxy)-phenylboronic acid (1.019 g, 4.95 mmol), potassium carbonate (1.140 g, 8.25 mmol), and catalyst $PdCl_2(dppf)$ (91 mg, 0.124 mmol). The reaction mixture was bubbling with nitrogen at room temperature for 20 min, and then heated in an oil bath at 40° C. overnight under a nitrogen atmosphere. The reaction mixture was then cooled to room temperature, diluted with 20 ml DCM, filtered through silica gel, and concentrated in vacuo. The residue was purified by flash chromatography (BIOTAGE, Horizon) using hexane/DCM/MeOH (75/24/1) to yield the title compound. ¹H NMR (500 MHz, $CD_3OD$) δ 9.62 (s, 1H); 8.52 (d, j=6, 1H); 7.81 (d, j=8.0, 1H); 7.68 (m, 3H); 7.45 (m, 2H); 7.38 (s, 1H). MS: $[M+H]^+$ 323.64.

Intermediate 2

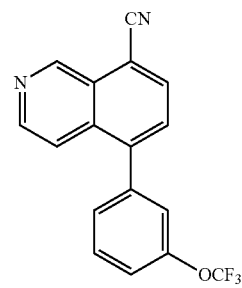

5-(3-(trifluoromethoxy)phenyl)isoquinoline-8-carbonitrile

To a solution of Intermediate 1 (300 mg, 4.12 mmol) in DMF (20 mL) was added $PdCl_2(dppf)$ (34 mg, 0.05 mmol) and zinc cyanide (1.1 g, 9.3 mmol). The reaction mixture was bubbling with nitrogen at room temperature for 20 min, and then the reaction mixture was heated in an oil bath at 150° C. overnight under a nitrogen atmosphere. The reaction mixture was then cooled to room temperature and filtered through silica gel. The organics were taken up into ethyl acetate (50 mL) and washed with water (3×50 mL). The organic layer was dried over sodium sulfate, filtered and concentrated in vacuo to give the crude product. The crude product was purified by flash chromatography (BIOTAGE, Horizon) using hexane/ethyl acetate (0 to 100%) to yield the title compound. ¹H NMR (500 MHz, CD₃OD) δ 9.60 (s, 1H); 8.66 (d, j=5.5, 1H); 8.26 (d, j=6.5, 1H); 7.90 (d, j=7.5, 1H); 7.84 (d, j=5.5, 1H); 7.72 (m, 1H); 7.56 (d, j=7.5, 1H); 7.49 (m, 2H). MS: [M]⁺ 314.71.

Intermediate 3

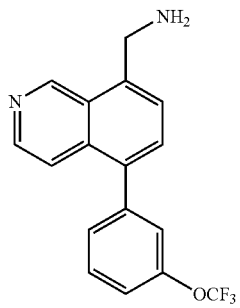 [SMILES: NCc1ccc(-c2cccc(OC(F)(F)F)c2)c2ccncc12]

(5-(3-(trifluoromethoxy)phenyl)isoquinolin-8-yl)methanamine

Intermediate 2 (280 mg, 0.891 mmol) and Raney Nickel (52.3 mg, 0.891 mmol) in 7 N ammonia in MeOH (30 mL) was stirred under a hydrogen atmosphere (1 atm) for 80 min. The reaction mixture was filtered, concentrated in vacuo, and purified on Gilson preparative HPLC to yield the title compound after lyophilization from H₂O/AcCN (3:1). ¹H NMR (500 MHz, CD₃OD) δ 9.86 (s, 1H); 8.64 (d, j=6.5, 1H); 8.06 (d, j=7.0, 1H); 8.02 (s, 2H); 7.73 (m, 1H); 7.53 (m, 2H); 7.46 (s, 1H); 4.88 (s, 2H). MS: [M+H]⁺ 319.73.

Intermediate 4

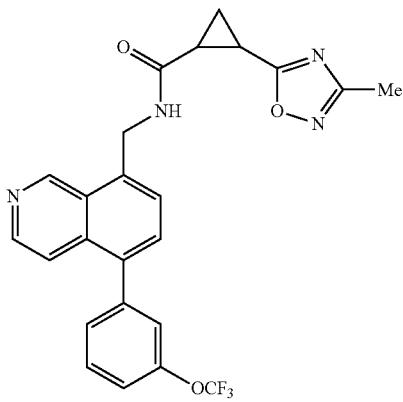 [SMILES: Cc1noc(C2CC2C(=O)NCc2ccc(-c3cccc(OC(F)(F)F)c3)c3ccncc23)n1]

(trans)-2-(3-methyl-1,2,4-oxadiazol-5-yl)-N-((5-(3-trifluoromethoxy)phenyl)isoquinolin-8-yl)methyl)cyclopropanecarboxamide To Intermediate 3 (245 mg, 0.691 mmol) in dry DMF (10 ml) was added DIEA (0.482 ml, 2.76 mmol) and HBTU (548 mg, 1.381 mmol), This reaction mixture was stirred for 15 min, then Intermediate 7 (150 mg, 0.898 mmol) was added. The resulting mixture was stirred at room temperature overnight. Upon completion, the reaction was concentrated in vacuo and the residue was purified on the Gilson preparative HPLC with 12 min method (CH₃CN/H₂O 20%-90%) to give the title compound after lyophilization from H₂O/AcCN (3:1). ¹H NMR (500 MHz, CD3OD) δ 10.07 (s, 1H); 8.61 (d, j=7.0, 1H); 8.30 (d, j=7.0, 1H); 8.15 (d, j=7.5, 1H); 8.07 (d, j=7.5, 1H); 7.72 (m, 1H); 7.55 (d, j=8.0, 1H); 7.50 (m, 2H); 5.14 (s, 2H); 2.69 (m, 1H); 2.42 (m, 1H); 2.29 (s, 3H); 1.72 (m, 1H); 1.60 (m, 1H). [M+H]⁺: 469.14.

Intermediate 5

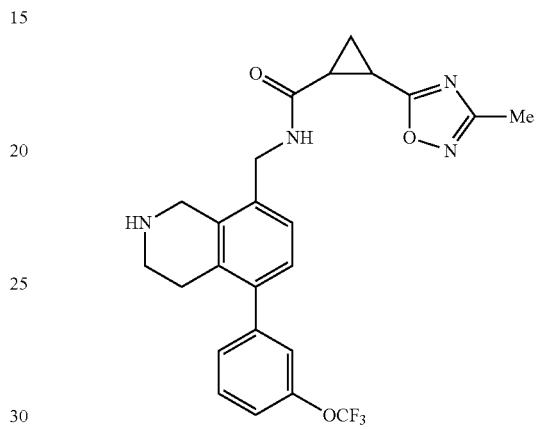

(trans)-2-(3-methyl-1,2,4-oxadiazol-5-yl)-N-((5-(3-(trifluoromethoxy)phenyl)-1,2,3,4-tetrahydroisoquinolin-8-yl)methyl)cyclopropanecarboxamide To Intermediate 4 (310 mg, 0.637 mmol) in MeOH (20 mL) and glacial acetic acid (3 mL) was added sodium cyanoborohydride (125 mg, 1.99 mmol) in portions. The resulting reaction mixture was stirred overnight at room temperature and upon completion, as judged by LCMS, the reaction was concentrated and used without further purification. ¹H NMR (500 MHz, CD₃OD) δ 8.91 (s, 1H); 7.58 (m, 1H); 7.31 (m, 5H); 4.50 (s, 2H); 4.45 (s, 2H); 3.41 (m, 2H); 2.93 (m, 2H); 2.67 (m, 1H); 2.40 (m, 1H): 2.32 (s, 3H); 1.71 (m, 1H); 1.60 (m, 1H). MS: [M+H]⁺ 472.78.

Intermediate 6

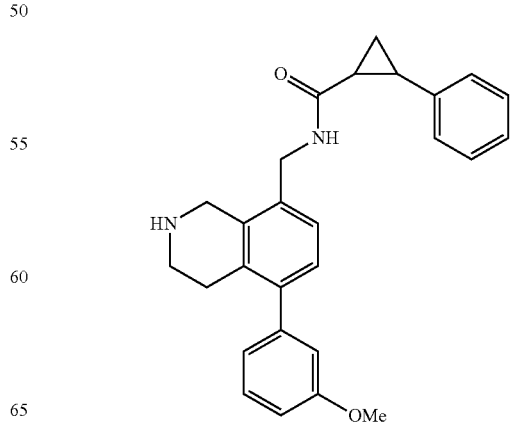

N-((5-(3-methoxyphenyl)-1,2,3,4-tetrahydroisoquinolin-8-yl)methyl)-2-phenylcyclopropanecarboxamide: Intermediate 6 was prepared by adapting the procedures for the synthesis of Intermediate 5. [M+H]+ 413.18.

Intermediate 7

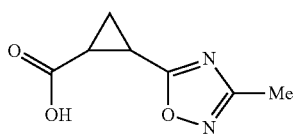 [SMILES: Cc1noc(C2CC2C(=O)O)n1]

Step A. Methyl 2-(chlorocarbonyl)cyclopropanecarboxylate

Sulfuryl dichloride (330 g, 2.77 mmol, 2.0 equiv.) was added dropwise to a solution of 2-(methoxycarbonyl)cyclopropane-carboxylic acid (200 g, 1.39 mol, 1.00 equiv) in toluene (2000 mL) under a nitrogen atmosphere at 0-5° C. for 30 min. The resulting reaction mixture was stirred for 3 h at 80° C., then cooled and concentrated in vacuo to give the title compound as a crude product.

Step B. Methyl 2-(3-methyl-1,2,4-oxadiazol-5-yl)cyclopropanecarboxylate

Methyl 2-(chlorocarbonyl)cyclopropanecarboxylate (220 g, 1.35 mol, 1.00 equiv) was added to a mixture of (E)-N-hydroxyacetamidine (150 g, 2.03 mol, 1.50 equiv), pyridine (330 g, 4.18 mol, 3.00 equiv) and toluene (2000 mL) at 0-5° C. over a 60 min period. The resulting reaction mixture was stirred for 1 h at room temperature, and then heated to reflux overnight. The reaction mixture was cooled, washed with 1 N HCL (2×1500 mL), and then brine (1×1500 mL). The organic layer was dried over anhydrous sodium sulfate and concentrated in vacuo to give the title compound as a crude product.

Step C. 2-(3-Methyl-1,2,4-oxadiazol-5-yl)cyclopropanecarboxylic acid

Sodium hydroxide (57 g, 1.43 mol, 2.0 equiv.) in water (800 mL) was added to a solution of methyl 2-(3-methyl-1,2,4-oxadiazol-5-yl)cyclopropanecarboxylate (130 g, 714.29 mmol, 1.00 equiv.) in tetrahydrofuran (1500 mL). The resulting reaction mixture was stirred overnight at room temperature, and then the reaction mixture concentrated in vacuo to remove the THF. The residual solution was washed with EtOAc (800 mL), and the pH of the remaining aqueous solution was adjusted to pH 3 with HCl (1 mol/L). The resulting solution was extracted with ethyl acetate (3×2 L). The organic layers were combined, dried over anhydrous sodium sulfate and concentrated in vacuo to give the title compound. MS: [M+H]+ 169.

Intermediate 8

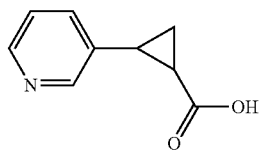 [SMILES: O=C(O)C1CC1c1cccnc1]

Step A. (Z)-ethyl 3-(pyridin-3-yl)acrylate

In order Pd(OAc)2 (4 g, 17.82 mmol, 0.05 equiv), PPh3 (14 g, 53.37 mmol, 0.15 equiv), Et3N (400 g, 3.96 mol, 2.50 equiv), ethyl acrylate (237 g, 2.37 mol, 1.50 equiv), and 3-bromopyridine (250 g, 1.58 mol, 1.00 equiv) in NMP (500 ml) were added to a round bottom flask. The resulting reaction mixture was stirred 24 hours at 110° C. in an oil bath. Then the reaction mixture was diluted with H2O (2 L). The reaction mixture was washed with EtOAc (3×800 mL), and the organic layers were combined. The organic layer was dried over Na2SO4 and concentrated in vacuo to give the title compound as a crude product.

Step B. Ethyl 2-(pyridin-3-yl)cyclopropanecarboxylate (Z)-ethyl 3-(pyridin-3-yl)acrylate (150 g, 846.5 mmol, 1.00 equiv) in DMSO (1200 ml) was added to a mixture of Me3SOI (225 g, 1.0227 mol, 1.20 equiv) and NaH (25 g, 1.0417 mol, 1.20 equiv) at 25° C. The reaction mixture was stirred for 40 minutes at 50-60° C. in an oil bath. The reaction mixture was washed with water (2 L) and the mixture was washed with DCM (3×500 mL). The organic layer was then washed with water (3×1 L). The organic layers were combined, dried over MgSO4, and concentrated in vacuo to give the crude product. The crude product was purified by flash chromatography (1:5 EtOAc/petroleum ether) to give the title compound.

Step C. 2-(pyridin-3-yl)cyclopropanecarboxylic acid

NaOH (50 g, 1.25 mol, 2.00 equiv) in H2O (50 g) was added to a solution of ethyl 2-(pyridin-3-yl)cyclopropanecarboxylate (75 g, 392.67 mmol, 1.00 equiv) in THF (1000 ml). The resulting reaction mixture was refluxed overnight in an oil bath. The reaction mixture was cooled to room temperature and filtered through CELITE, and the filter cake was washed with THF. A filtration was performed. The filter cake was washed with THF. Adjustment of the pH to 2 was accomplished by the addition of HCl. A filtration was performed. The residue was dissolved in MeOH. A filtration was performed. The filtrate was concentrated by evaporation under vacuum using a rotary evaporator. The resulting mixture was washed with CH3COCH3. The resulting compound was obtained after evaporating the filtrate in vacuo. MS: [M+HCl]+ 200.

Intermediate 9

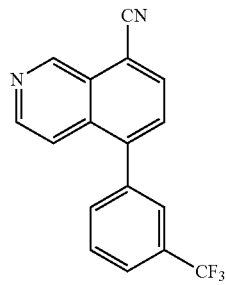 [SMILES: N#Cc1ccc(-c2cccc(C(F)(F)F)c2)c2ccncc12]

Step A. 8-chloro-5-(3-(trifluoromethyl)phenyl)isoquinoline

To a solution of 5-bromo-8-chloroisoquinoline (2 g, 8.25 mmol) in toluene (50 ml), ethanol (25 ml), and water (12.5 ml) was added (3-(trifluoromethyl)phenyl)boronic acid (2.350 g, 12.37 mmol), Pd(PPh₃)₄ (0.477 g, 0.412 mmol), and K₂CO₃ (2.508 g, 18.14 mmol). The reaction mixture was stirred at 90° C. for 1 h. Then the reaction mixture was cooled to room temperature. The solvent was removed in vacuo and the residue was disolved in EtOAc (100 mL) and washed with brine (30 ml). The organic layer was dried over Na₂SO₄, filtered, and concentrated in vacuo. The crude product was purified by silica gel column chromatography (EtOAc/isohexane 20/80) to give the title compound.

Step B. 5-(3-(trifluoromethyl)phenyl)isoquinoline-8-carbonitrile 8-chloro-5-(3-(trifluoromethyl)phenyl)isoquinoline (2.52 g) was mixed with Zn(CN)₂ (0.763 g, 6.50 mmol), CS₂CO₃ (2.118 g, 6.50 mmol), and [PdCl₂(dppf)] (0.162 mmol) in 15 ml THF. The mixture was heated at 140° C. for 1 h under microwave irradiation, and then water (10 ml) was added. The aqueous mixture was extracted with EtOAc (3×20 ml). The combined organic layers were washed with brine and dried over Na₂SO₄. The crude product was purified by silica gel column chromatography (EtOAc/isohexane 10:90) to give the title compound. MS: [M+H]⁺ 299.23.

Intermediate 10

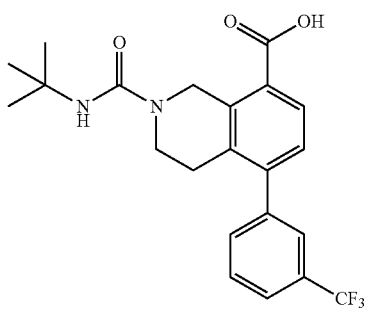 [SMILES: CC(C)(C)NC(=O)N1CCc2c(-c3cccc(C(F)(F)F)c3)ccc(C(=O)O)c2C1]

2-(tert-butylcarbamoyl)-5-(3-(trifluoromethyl)phenyl)-1,2,3,4-tetrahydroisoquinoline-8-carboxylic acid Intermediate 9 (0.70 g, 2.34 mmol) and KOH (0.263 g, 4.69 mmol) in 20 ml water and 20 ml EtOH were stirred at 60° C. overnight. The solvent was evaporated in vacuo. The residue was dissolved in AcOH (20 ml), and NaCNBH₃ (0.885 g, 14.08 mmol) was added. The resulting reaction mixture was heated to 80° C. for 1 h. The solvent was evaporated in vacuo, and the residue was diluted in CH₂Cl₂ (20 ml). Then tert-Butyl isocyanate (0.349 g, 3.52 mmol) and Et₃N (0.522 g, 5.16 mmol) was added to the solution. The resulting reaction mixture was stirred at room temperature for 2 h. Then water was added and the mixture was washed with water and then brine. The organic layer was dried over Na₂SO₄, filtered, and concentrated in vacuo. The crude product was purified on Gilson preparative HPLC (12 min method, eluting with CH₃CN/H₂O), to give the title compound. MS: [M+H]⁺ 21.49.

EXAMPLES

Example 1

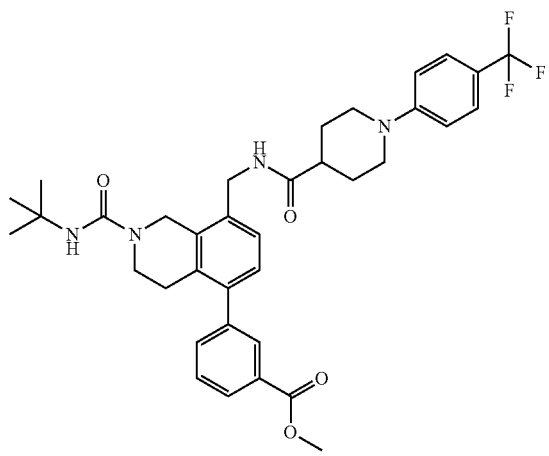 [SMILES: COC(=O)c1cccc(-c2ccc(CNC(=O)C3CCN(c4ccc(C(F)(F)F)cc4)CC3)c3c2CCN(C(=O)NC(C)(C)C)C3)c1]

Step A. 5-chloroisoquinoline-8-carbonitrile

Zinc cyanide (3.63 mg, 0.03 mmol) and PdCl₂(dppf) (2.2 mg, 0.003 mmol) were added to a solution of 8-bromo-5-chloroisoquinoline (15 mg, 0.06 mmol) in DMF(3 mL), and the reaction mixture was heated to 116 degrees for 5 hours. The reaction mixture was concentrated in vacuo, and the resulting crude product was purified on flash chromatography (BIOTAGE, Horizon) (hexanes:ethyl acetate) to afford the title compound.

Step B. methyl 3-(8-cyanoisoquinolin-5-yl)benzoate

5-Chloroisoquinoline-8-carbonitrile (50 mg, 0.27 mmol) was treated with dioxane (4 mL), 2 N potassium carbonate (0.5 mL), methyl 3-(4,4,5,5-tetramethyl-1,3,2-dioxaborolan-2-yl)benzoate (104 mg, 0.4 mmol), and PdCl₂(dppf) (19 mg, 0.03 mmol). The reaction mixture was stirred under nitrogen at room temperature overnight. The reaction was concentrated and the crude product was purified by flash chromatography (Biotage, Horizon) (hexanes:ethyl acetate) to afford the title compound.

Step C. methyl 3-(8-(aminomethyl)isoquinolin-5-yl)benzoate

Methyl 3-(8-cyanoisoquinolin-5-yl)benzoate (33 mg, 0.11 mmol) was treated with Raney Ni in 7 M ammonium/methanol (15 mL), and the resulting reaction mixture was stirred under a hydrogen atmosphere for 1 hour. The reaction mixture was filtered, concentrated in vacuo, and used in the next step without further purification.

Step D. methyl 3-(8-((1-(4-(trifluoromethyl)phenyl) piperidine-4-carboxamido)methyl)isoquinolin-5-yl) benzoate To methyl 3-(8-(aminomethyl)isoquinolin-5-yl)benzoate (40 mg, 0.14 mmol) in DMF/DCM (1:2) was treated with EDC (26.2, 0.14 mmol), HOBT (21 mg, 0.14 mmol), and 1-(4-(trifluoromethyl)phenyl)piperidine-4-carboxylic acid (37 mg, 0.14 mmol). The reaction mixture was stirred overnight, and the reaction mixture was diluted with DCM and washed with brine. The organic layer was dried over sodium sulfate, filtered and concentrated in vacuo to give the crude product. The crude product was purified on the Gilson preparative HPLC (12 min method, eluting with CH$_3$CN/H$_2$O) to give the title compound.

Step E. methyl 3-(2-(tert-butylcarbamoyl)-8-((1-(4-(trifluoromethyl)phenyl)piperidine-4-carboxamido)methyl)-1,2,3,4-tetrahydroisoquinolin-5-yl)benzoate Sodium cyanoborohydride (4 mg, 0.06 mmol) was added to a mixture of methyl 3-(8-((1-(4-(trifluoromethyl)phenyl)piperidine-4-carboxamido)methyl)isoquinolin-5-yl)benzoate (7 mg, 0.013 mmol) in methanol and glacial acetic acid (10:1). The reaction mixture was stirred overnight, and the reaction mixture was concentrated in vacuo. The residue was dissolved in DCM (5 mL) and triethylamine (13 mg, 0.13 mmol) and t-butyl isocyanate (2.5 mg, 0.03 mmol) was added. The resulting reaction mixture was stirred for 5 hours. The reaction mixture was concentrated in vacuo to give the crude product. The crude product was purified on the Gilson preparative HPLC (12 min method, eluting with CH$_3$CN/H$_2$O) to give the title compound. [M+H]$^+$: 651.46.

The synthetic procedure used to synthesize Example 1 was adapted to synthesize Examples 2-5 in Table 1.

TABLE 1

| Ex. # | Structure | Name | MS |
|---|---|---|---|
| 2 | 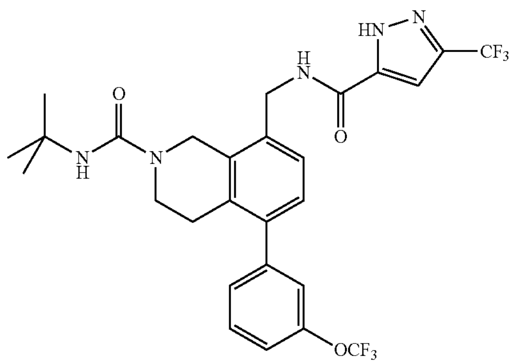 [SMILES: CC(C)(C)NC(=O)N1CCc2c(-c3cccc(OC(F)(F)F)c3)ccc(CNC(=O)c3cc(C(F)(F)F)n[nH]3)c2C1] | N-(tert-butyl)-5-(3-(trifluoromethoxy)phenyl)-8-((3-(trifluoromethyl)-1H-pyrazole-5-carboxamido)methyl)-3,4-dihydroisoquinoline-2(1H)-carboxamide | 584.2 |
| 3 | 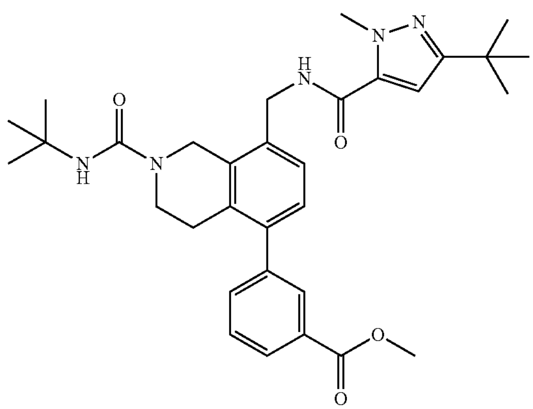 [SMILES: COC(=O)c1cccc(-c2ccc(CNC(=O)c3cc(C(C)(C)C)nn3C)c3c2CCN(C(=O)NC(C)(C)C)C3)c1] | methyl 3-(8-((3-(tert-butyl)-1-methyl-1H-pyrazole-5-carboxamido)methyl)-2-(tert-butylcarbamoyl)-1,2,3,4-tetrahydroisoquinolin-5-yl)benzoate | 560.39 |
| 4 | 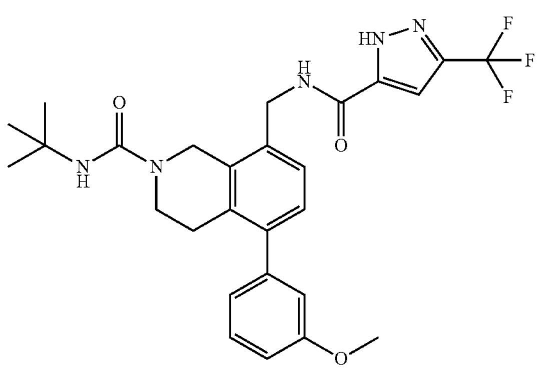 [SMILES: COc1cccc(-c2ccc(CNC(=O)c3cc(C(F)(F)F)n[nH]3)c3c2CCN(C(=O)NC(C)(C)C)C3)c1] | N-(tert-butyl)-5-(3-methoxyphenyl)-8-((3-(trifluoromethyl)-1H-pyrazole-5-carboxamido)methyl)-3,4-dihydroisoquinoline-2(1H)-carboxamide | 530.30 |

TABLE 1-continued

| Ex. # | Structure | Name | MS |
|---|---|---|---|
| 5 | 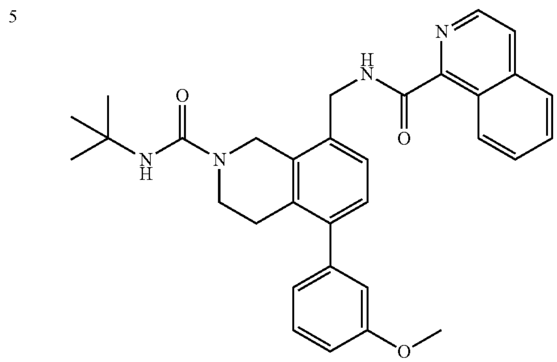 | N-((2-(tert-butylcarbamoyl)-5-(3-methoxyphenyl)-1,2,3,4-tetrahydroisoquinolin-8-yl)methyl)isoquinoline-1-carboxamide | 523.38 |

Example 6

$N^2$-(tert-butyl)-$N^8$-(2-(5-chloro-1H-benzo[d]imidazol-2-yl)ethyl)-5-(3-(trifluoromethyl)phenyl)-3,4-dihydroisoquinoline-2,8(1H)-dicarboxamide

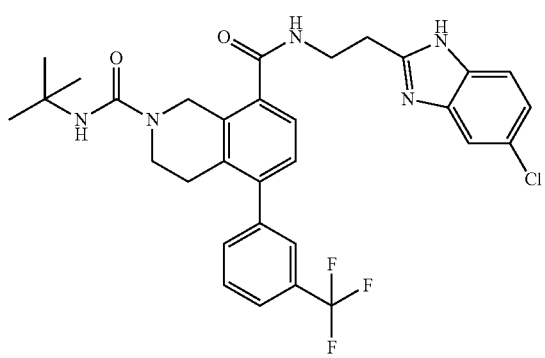 [SMILES: CC(C)(C)NC(=O)N1CCc2c(-c3cccc(C(F)(F)F)c3)ccc(C(=O)NCCc3nc4cc(Cl)ccc4[nH]3)c2C1]

To a solution of Intermediate 10 (20 mg, 0.048 mmol) in 1 mL DCM was added 2-(5-chloro-1H-benzo[d]imidazol-2-yl)ethanamine (20 mg, 0.074 mmol), Et$_3$N (0.05 ml, 0.359 mmol), and HBTU (40 mg, 0.105 mmol). The resulting reaction mixture was stirred at room temperature for 3 h. The reaction mixture was filtered, concentrated in vacuo, and the crude product was purified on a Gilson preparative HPLC (12 min method CH$_3$CN/H$_2$O+0.1% TFA) to give the title compound. MS: [M+H]$^+$ 598.02

The synthetic procedure used to synthesize Example 6 was adapted to synthesize Examples 7-81 in Table 2.

TABLE 2

| Ex. # | Structure | Name | MS |
|---|---|---|---|
| 7 | 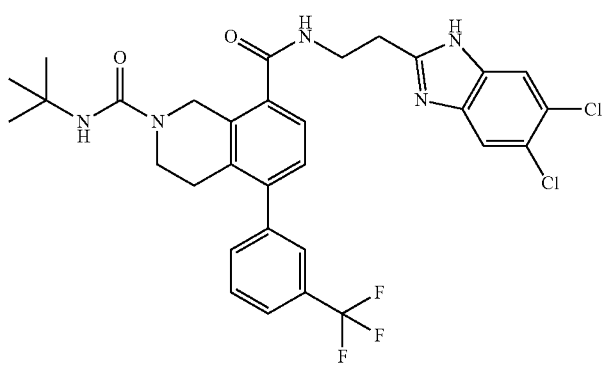 [SMILES: CC(C)(C)NC(=O)N1CCc2c(-c3cccc(C(F)(F)F)c3)ccc(C(=O)NCCc3nc4cc(Cl)c(Cl)cc4[nH]3)c2C1] | $N^2$-(tert-butyl)-$N^8$-(2-(5,6-dichloro-1H-benzo[d]imidazol-2-yl)ethyl)-5-(3-(trifluoromethyl)phenyl)-3,4-dihydroisoquinoline-2,8(1H)-dicarboxamide | 632.02 |

TABLE 2-continued

| Ex. # | Structure | Name | MS |
|---|---|---|---|
| 8 | 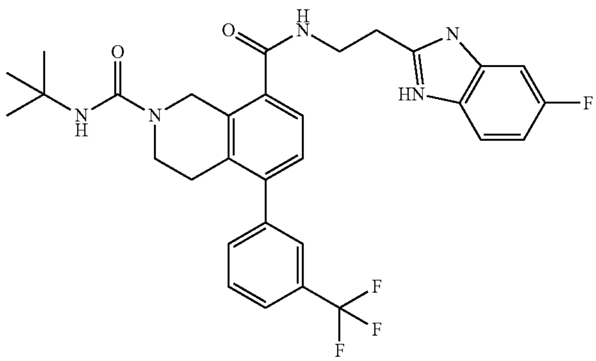 [SMILES: CC(C)(C)NC(=O)N1CCc2c(-c3cccc(C(F)(F)F)c3)ccc(C(=O)NCCc3nc4ccc(F)cc4[nH]3)c2C1] | $N^2$-(tert-butyl)-$N^8$-(2-(5-fluoro-1H-benzo[d]imidazol-2-yl)ethyl)-5-(3-(trifluoromethyl)phenyl)-3,4-dihydroisoquinoline-2,8(1H)-dicarboxamide | 582.01 |
| 9 | 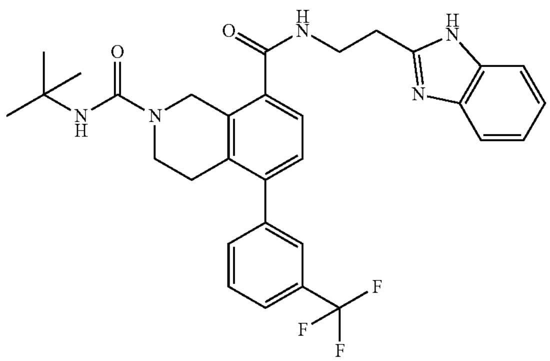 [SMILES: CC(C)(C)NC(=O)N1CCc2c(-c3cccc(C(F)(F)F)c3)ccc(C(=O)NCCc3nc4ccccc4[nH]3)c2C1] | $N^8$-(2-(1H-benzo[d]imidazol-2-yl)ethyl)-$N^2$-(tert-butyl)-5-(3-(trifluoromethyl)phenyl)-3,4-dihydroisoquinoline-2,8(1H)-dicarboxamide | 564.04 |
| 10 | 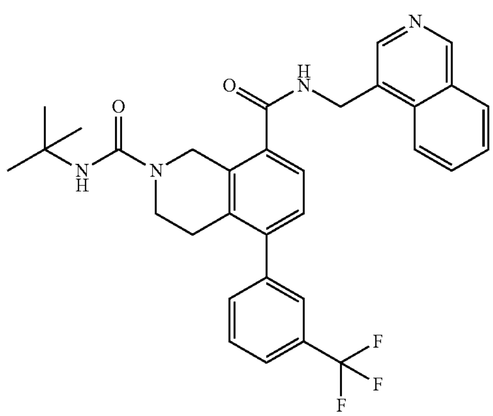 [SMILES: CC(C)(C)NC(=O)N1CCc2c(-c3cccc(C(F)(F)F)c3)ccc(C(=O)NCc3cncc4ccccc34)c2C1] | $N^2$-(tert-butyl)-$N^8$-(isoquinolin-4-ylmethyl)-5-(3-(trifluoromethyl)phenyl)-3,4-dihydroisoquinoline-2,8(1H)-dicarboxamide | 561.11 |
| 11 | 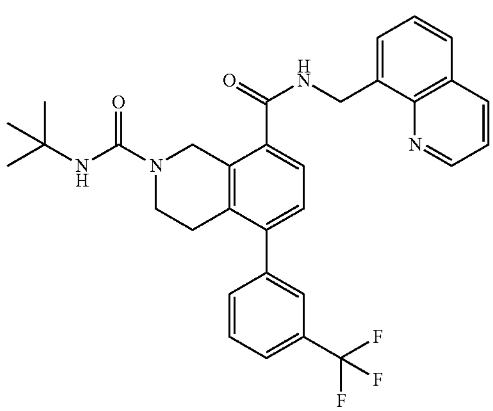 [SMILES: CC(C)(C)NC(=O)N1CCc2c(-c3cccc(C(F)(F)F)c3)ccc(C(=O)NCc3cccc4cccnc34)c2C1] | $N^2$-(tert-butyl)-$N^8$-quinolin-8-ylmethyl)-5-(3-(trifluoromethyl)phenyl)-3,4-dihydroisoquinoline-2,8(1H)-dicarbox-amide | 561.12 |

TABLE 2-continued

| Ex. # | Structure | Name | MS |
|---|---|---|---|
| 12 | 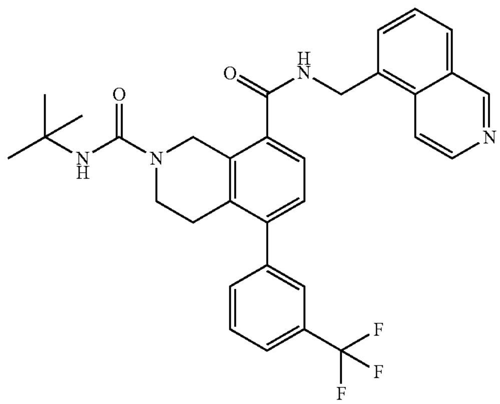 [SMILES: CC(C)(C)NC(=O)N1CCc2c(-c3cccc(C(F)(F)F)c3)ccc(C(=O)NCc3cccc4cnccc34)c2C1] | $N^2$-(tert-butyl)-$N^8$-(isoquinolin-5-ylmethyl)-5-(3-(trifluoromethyl)phenyl)-3,4-dihydroisoquinoline-2,8(1H)-dicarboxamide | 561.11 |
| 13 | 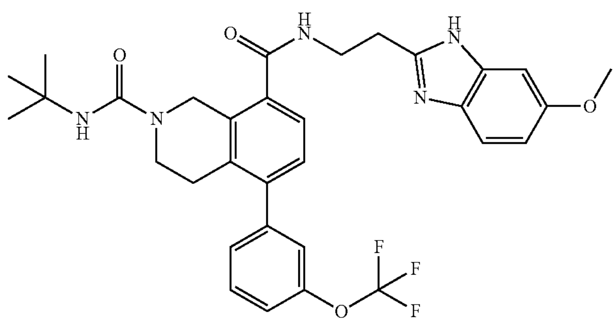 [SMILES: COc1ccc2nc(CCNC(=O)c3ccc(-c4cccc(OC(F)(F)F)c4)c4c3CN(C(=O)NC(C)(C)C)CC4)[nH]c2c1] | $N^2$-(tert-butyl)-$N^8$-(2-(6-methoxy-1H-benzo[d]imidazol-2-yl)ethyl)-5-(3-(trifluoromethoxy)phenyl)-3,4-dihydroisoquinoline-2,8(1H)-dicarboxamide | 610.09 |
| 14 | 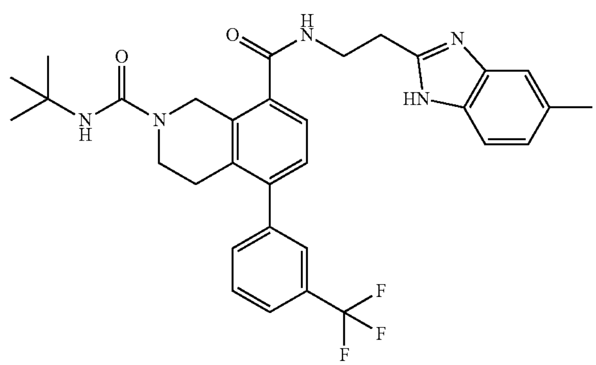 [SMILES: Cc1ccc2[nH]c(CCNC(=O)c3ccc(-c4cccc(C(F)(F)F)c4)c4c3CN(C(=O)NC(C)(C)C)CC4)nc2c1] | $N^2$-(tert-butyl)-$N^8$-(2-(5-methyl-1H-benzo[d]imidazol-2-yl)ethyl)-5-(3-(trifluoromethyl)phenyl)-3,4-dihydroisoquinoline-2,8(1H)-dicarboxamide | 578.07 |
| 15 | 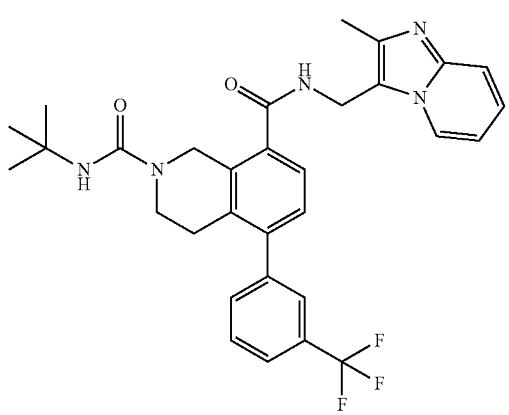 [SMILES: Cc1nc2ccccn2c1CNC(=O)c1ccc(-c2cccc(C(F)(F)F)c2)c2c1CN(C(=O)NC(C)(C)C)CC2] | $N^2$-(tert-butyl)-$N^8$-((2-methylimidazo[1,2-a]pyridin-3-yl)methyl)-5-(3-(trifluoromethyl)phenyl)-3,4-dihydroisoquinoline-2,8(1H)-dicarboxamide | 564.20 |

TABLE 2-continued

| Ex. # | Structure | Name | MS |
|---|---|---|---|
| 16 | 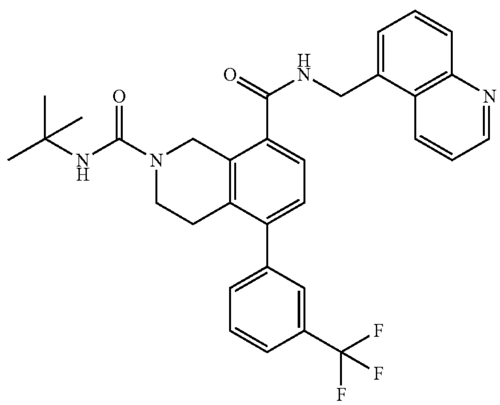 [SMILES: CC(C)(C)NC(=O)N1CCc2c(-c3cccc(C(F)(F)F)c3)ccc(C(=O)NCc3cccc4ncccc34)c2C1] | $N^2$-(tert-butyl)-$N^8$-(quinolin-5-ylmethyl)-5-(3-(trifluoromethyl)phenyl)-3,4-dihydroisoquinoline-2,8(1H)-dicarboxamide | 561.17 |
| 17 | 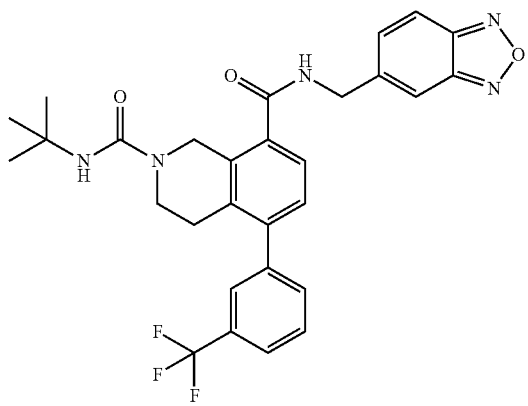 [SMILES: CC(C)(C)NC(=O)N1CCc2c(-c3cccc(C(F)(F)F)c3)ccc(C(=O)NCc3ccc4nonc4c3)c2C1] | $N^8$-(benzo[c][1,2,5]oxadiazol-5-ylmethyl)-$N^2$-(tert-butyl)-5-(3-(trifluoromethyl)phenyl)-3,4-dihydroisoquinoline-2,8(1H)-dicarboxamide | 552.20 |
| 18 | 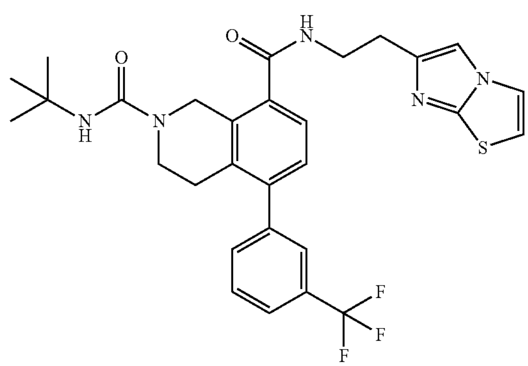 [SMILES: CC(C)(C)NC(=O)N1CCc2c(-c3cccc(C(F)(F)F)c3)ccc(C(=O)NCCc3cn4ccsc4n3)c2C1] | $N^2$-(tert-butyl)-$N^8$-(2-(imidazo[2,1-b]thiazol-6-yl)ethyl)-5-(3-(trifluoromethyl)phenyl)-3,4-dihydroisoquinoline-2,8(1H)-dicarboxamide | 570.19 |
| 19 | 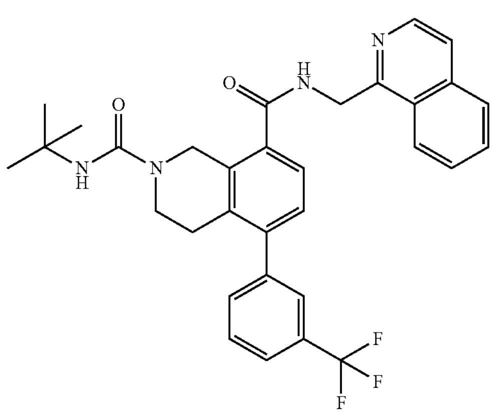 [SMILES: CC(C)(C)NC(=O)N1CCc2c(-c3cccc(C(F)(F)F)c3)ccc(C(=O)NCc3nccc4ccccc34)c2C1] | $N^2$-(tert-butyl)-$N^8$-(isoquinolin-1-ylmethyl)-5-(3-(trifluoromethyl)phenyl)-3,4-dihydroisoquinoline-2,8(1H)-dicarboxamide | 561.12 |

TABLE 2-continued

| Ex. # | Structure | Name | MS |
|---|---|---|---|
| 20 | 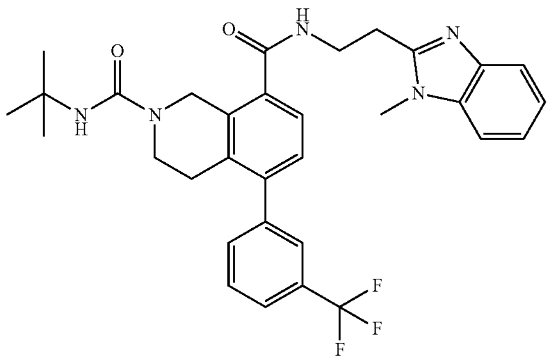 [SMILES: Cn1c(CCNC(=O)c2ccc(-c3cccc(C(F)(F)F)c3)c3c2CN(C(=O)NC(C)(C)C)CC3)nc2ccccc21] | $N^2$-(tert-butyl)-$N^8$-(2-(1-methyl-1H-benzo[d]imidazol-2-yl)ethyl)-5-(3-(trifluoromethyl)phenyl)-3,4-dihydroisoquinoline-2,8(1H)-dicarboxamide | 578.08 |
| 21 | 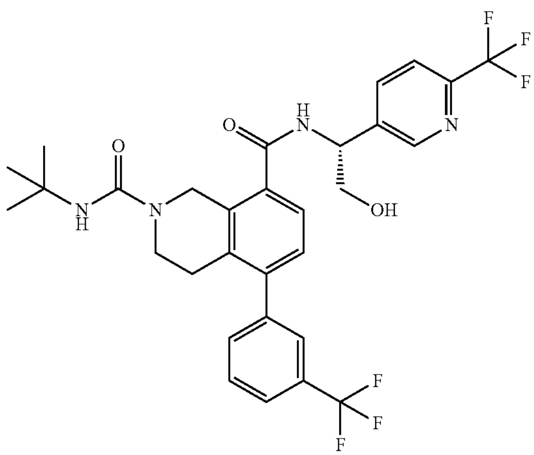 [SMILES: CC(C)(C)NC(=O)N1CCc2c(-c3cccc(C(F)(F)F)c3)ccc(C(=O)N[C@@H](CO)c3ccc(C(F)(F)F)nc3)c2C1] | (R/S)-$N^2$-(tert-butyl)-$N^8$-(2-hydroxy-1-(6-(trifluoromethyl)pyridin-3-yl)ethyl)-5-(3-(trifluoromethyl)phenyl)-3,4-dihydroisoquinoline-2,8(1H)-dicarboxamide (mixture of 2 enantiomers) | 609.08 |
| 22 | 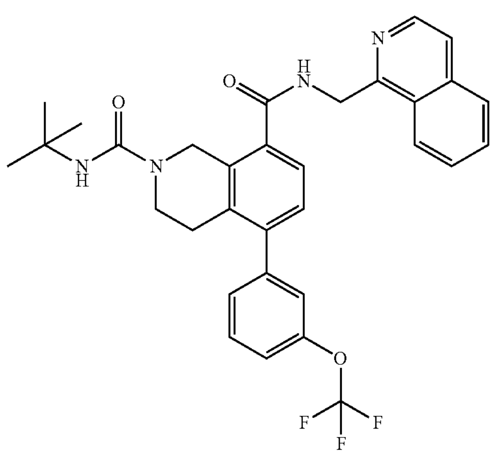 [SMILES: CC(C)(C)NC(=O)N1CCc2c(-c3cccc(OC(F)(F)F)c3)ccc(C(=O)NCc3nccc4ccccc34)c2C1] | $N^2$-(tert-butyl)-$N^8$-(isoquinolin-1-ylmethyl)-5-(3-(trifluoromethoxy)phenyl)-3,4-dihydroisoquinoline-2,8(1H)-dicarboxamide | 577.11 |
| 23 | 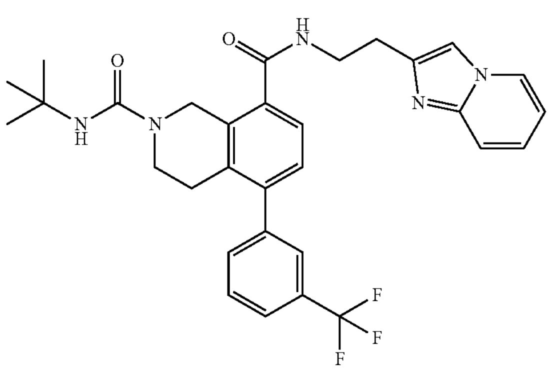 [SMILES: CC(C)(C)NC(=O)N1CCc2c(-c3cccc(C(F)(F)F)c3)ccc(C(=O)NCCc3cn4ccccc4n3)c2C1] | $N^2$-(tert-butyl)-$N^8$-(2-(imidazo[1,2-a]pyridin-2-yl)ethyl)-5-(3-(trifluoromethyl)phenyl)-3,4-dihydroisoquinoline-2,8(1H)-dicarboxamide | 564.21 |

TABLE 2-continued

| Ex. # | Structure | Name | MS |
|---|---|---|---|
| 24 | 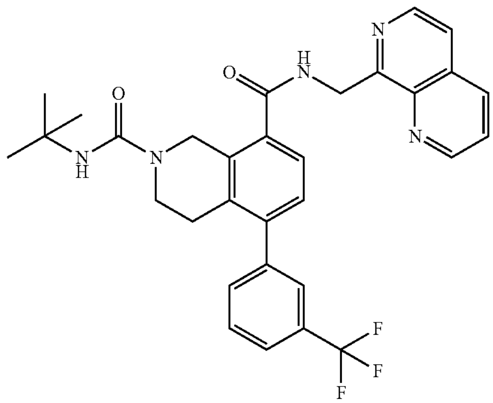 [SMILES: CC(C)(C)NC(=O)N1CCc2c(-c3cccc(C(F)(F)F)c3)ccc(C(=O)NCc3nccc4cccnc34)c2C1] | $N^8$-((1,7-naphthyridin-8-yl)methyl)-$N^2$-(tert-butyl)-5-(3-(trifluoromethyl)phenyl)-3,4-dihydroisoquinoline-2,8(1H)-dicarboxamide | 562.12 |
| 25 | 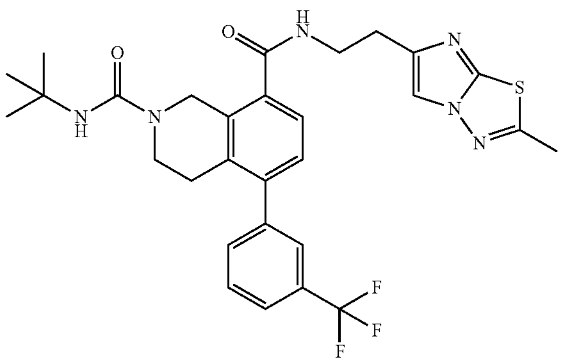 [SMILES: Cc1nn2cc(CCNC(=O)c3ccc(-c4cccc(C(F)(F)F)c4)c4c3CN(C(=O)NC(C)(C)C)CC4)nc2s1] | $N^2$-(tert-butyl)-$N^8$-(2-(2-methylimidazo[2,1-b][1,3,4]thiadiazol-6-yl)ethyl)-5-(3-(trifluoromethyl)phenyl)-3,4-dihydroisoquinoline-2,8(1H)-dicarboxamide | 585.21 |
| 26 | 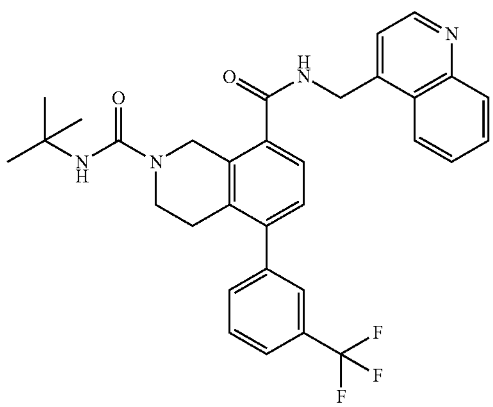 [SMILES: CC(C)(C)NC(=O)N1CCc2c(-c3cccc(C(F)(F)F)c3)ccc(C(=O)NCc3ccnc4ccccc34)c2C1] | $N^2$-(tert-butyl)-$N^8$-(quinolin-4-ylmethyl)-5-(3-(trifluoromethyl)phenyl)-3,4-dihydroisoquinoline-2,8(1H)-dicarboxamide | 561.17 |
| 27 | 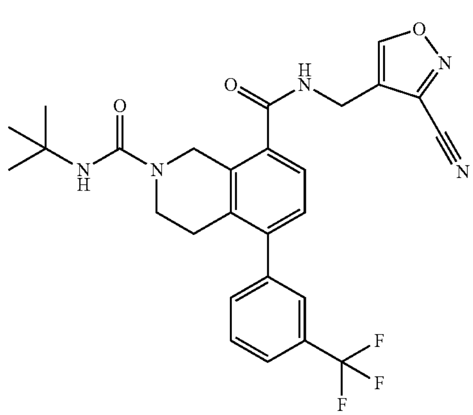 [SMILES: CC(C)(C)NC(=O)N1CCc2c(-c3cccc(C(F)(F)F)c3)ccc(C(=O)NCc3conc3C#N)c2C1] | $N^2$-(tert-butyl)-$N^8$-((3-cyanoisoxazol-4-yl)methyl)-5-(3-(trifluoromethyl)phenyl)-3,4-dihydroisoquinoline-2,8(1H)-dicarboxamide | 526.15 |

TABLE 2-continued

| Ex. # | Structure | Name | MS |
|---|---|---|---|
| 28 | 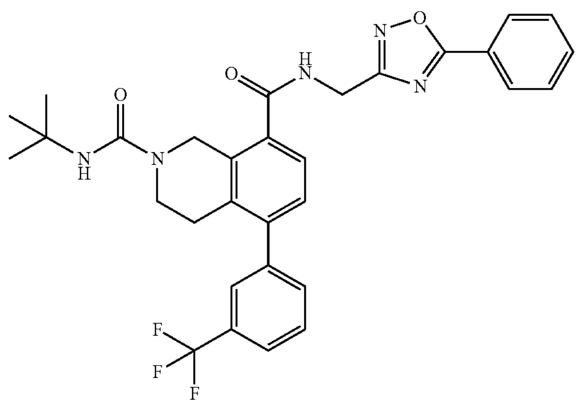 [SMILES: CC(C)(C)NC(=O)N1CCc2c(-c3cccc(C(F)(F)F)c3)ccc(C(=O)NCc3noc(-c4ccccc4)n3)c2C1] | $N^2$-(tert-butyl)-$N^8$-((5-phenyl-1,2,4-oxadiazol-3-yl)methyl)-5-(3-(trifluoromethyl)phenyl)-3,4-dihydroisoquinoline-2,8(1H)-dicarboxamide | 600.15 |
| 29 | 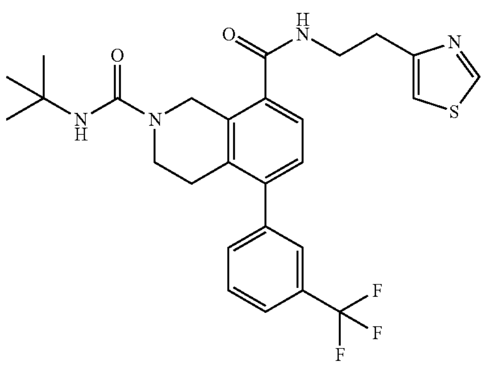 [SMILES: CC(C)(C)NC(=O)N1CCc2c(-c3cccc(C(F)(F)F)c3)ccc(C(=O)NCCc3cscn3)c2C1] | $N^2$-(tert-butyl)-$N^8$-(2-(thiazol-4-yl)ethyl)-5-(3-(trifluoromethyl)phenyl)-3,4-dihydroisoquinoline-2,8(1H)-dicarboxamide | 531.15 |
| 30 | 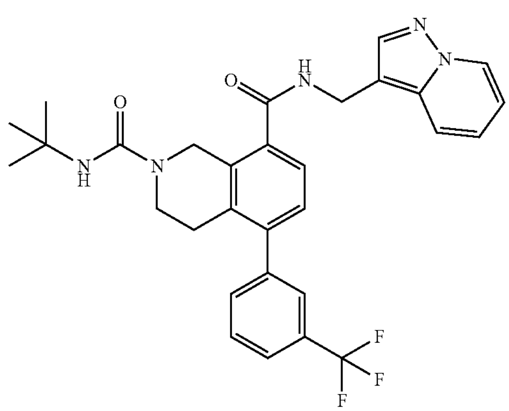 [SMILES: CC(C)(C)NC(=O)N1CCc2c(-c3cccc(C(F)(F)F)c3)ccc(C(=O)NCc3cnn4ccccc34)c2C1] | $N^2$-(tert-butyl)-$N^8$-(pyrazolo[1,5-a]pyridin-3-ylmethyl)-5-(3-(trifluoromethyl)phenyl)-3,4-dihydroisoquinoline-2,8(1H)-dicarboxamide | 550.19 |
| 31 | 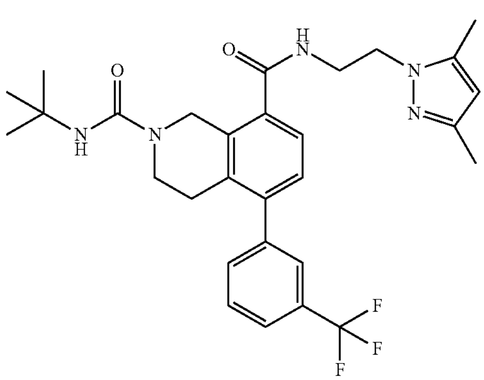 [SMILES: Cc1cc(C)n(CCNC(=O)c2ccc(-c3cccc(C(F)(F)F)c3)c3c2CN(C(=O)NC(C)(C)C)CC3)n1] | $N^2$-(tert-butyl)-$N^8$-(2-(3,5-dimethyl-1H-pyrazol-1-yl)ethyl)-5-(3-(trifluoromethyl)phenyl)-3,4-dihydroisoquinoline-2,8(1H)-dicarboxamide | 542.23 |

TABLE 2-continued

| Ex. # | Structure | Name | MS |
|---|---|---|---|
| 32 | 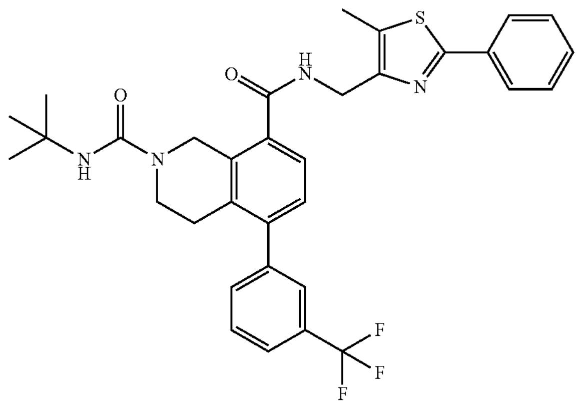 [SMILES: Cc1sc(-c2ccccc2)nc1CNC(=O)c1ccc(-c2cccc(C(F)(F)F)c2)c2c1CN(C(=O)NC(C)(C)C)CC2] | $N^2$-(tert-butyl)-$N^8$-((5-methyl-2-phenylthiazol-4-yl)methyl)-5-(3-(trifluoromethyl)phenyl)-3,4-dihydroisoquinoline-2,8(1H)-dicarboxamide | 607.23 |
| 33 | 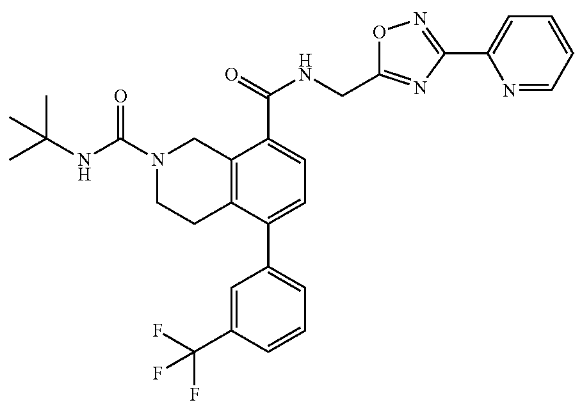 [SMILES: CC(C)(C)NC(=O)N1CCc2c(-c3cccc(C(F)(F)F)c3)ccc(C(=O)NCc3nc(-c4ccccn4)no3)c2C1] | $N^2$-(tert-butyl)-$N^8$-((3-(pyridin-2-yl)-1,2,4-oxadiazol-5-yl)methyl)-5-(3-(trifluoromethyl)phenyl)-3,4-dihydroisoquinoline-2,8(1H)-dicarboxamide | 601.16 |
| 34 | 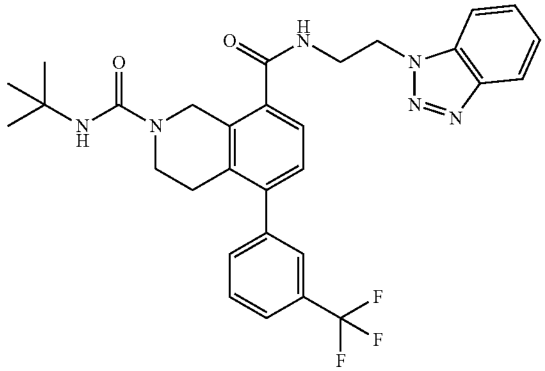 [SMILES: CC(C)(C)NC(=O)N1CCc2c(-c3cccc(C(F)(F)F)c3)ccc(C(=O)NCCn3nnc4ccccc43)c2C1] | $N^8$-(2-(1H-benzo[d][1,2,3]triazol-1-yl)ethyl)-$N^2$-(tert-butyl)-5-(3-(trifluoromethyl)phenyl)-3,4-dihydroisoquinoline-2,8(1H)-dicarboxamide | 565.21 |
| 35 | 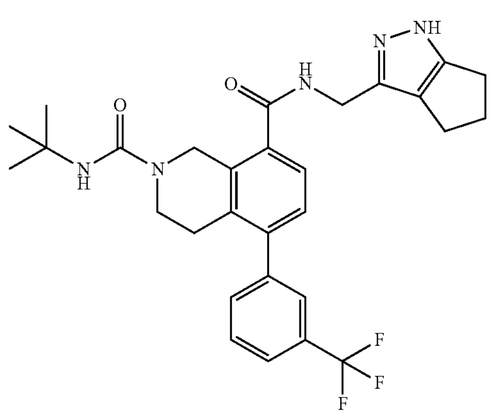 [SMILES: CC(C)(C)NC(=O)N1CCc2c(-c3cccc(C(F)(F)F)c3)ccc(C(=O)NCc3n[nH]c4c3CCC4)c2C1] | $N^2$-(tert-butyl)-$N^8$-((1,4,5,6-tetrahydrocyclopenta[c]pyrazol-3-yl)methyl)-5-(3-(trifluoromethyl)phenyl)-3,4-dihydroisoquinoline-2,8(1H)-dicarboxamide | 540.19 |

TABLE 2-continued

| Ex. # | Structure | Name | MS |
|---|---|---|---|
| 36 | 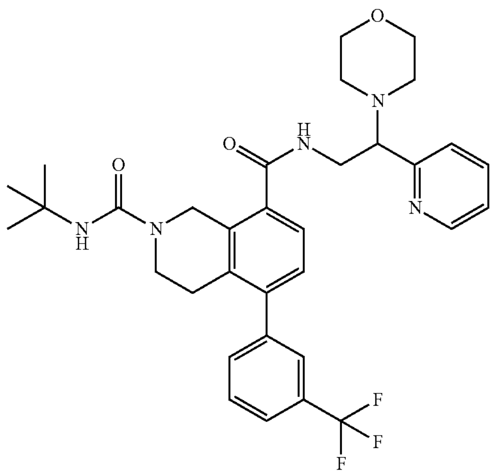 [SMILES: CC(C)(C)NC(=O)N1CCc2c(-c3cccc(C(F)(F)F)c3)ccc(C(=O)NCC(c3ccccn3)N3CCOCC3)c2C1] | $N^2$-(tert-butyl)-$N^8$-(2-morpholino-2-(pyridin-2-yl)ethyl)-5-(3-(trifluoromethyl)phenyl)-3,4-dihydroisoquinoline-2,8(1H)-dicarboxamide | 610.27 |
| 37 | 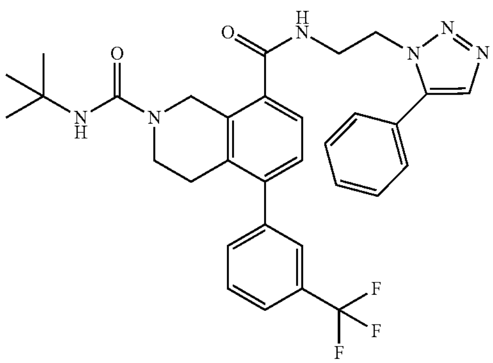 [SMILES: CC(C)(C)NC(=O)N1CCc2c(-c3cccc(C(F)(F)F)c3)ccc(C(=O)NCCn3nncc3-c3ccccc3)c2C1] | $N^2$-(tert-butyl)-$N^8$-(2-(5-phenyl-1H-1,2,3-triazol-1-yl)ethyl)-5-(3-(trifluoromethyl)phenyl)-3,4-dihydroisoquinoline-2,8(1H)-dicarboxamide | 591.26 |
| 38 | 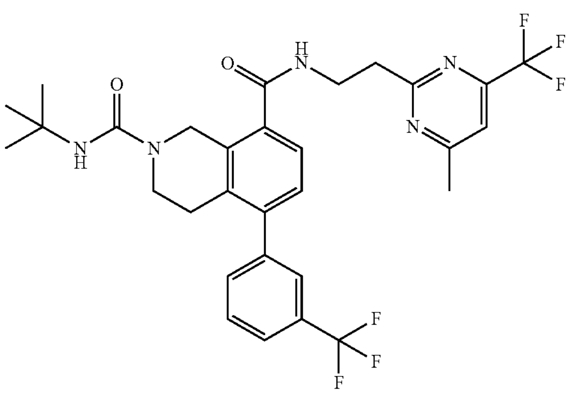 [SMILES: Cc1cc(C(F)(F)F)nc(CCNC(=O)c2ccc(-c3cccc(C(F)(F)F)c3)c3c2CN(C(=O)NC(C)(C)C)CC3)n1] | $N^2$-(tert-butyl)-$N^8$-(2-(4-methyl-6-(trifluoromethyl)pyrimidin-2-yl)ethyl)-5-(3-(trifluoromethyl)phenyl)-3,4-dihydroisoquinoline-2,8(1H)-dicarboxamide | 608.27 |
| 39 | 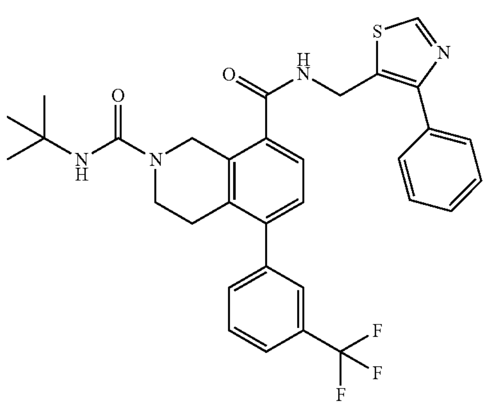 [SMILES: CC(C)(C)NC(=O)N1CCc2c(-c3cccc(C(F)(F)F)c3)ccc(C(=O)NCc3scnc3-c3ccccc3)c2C1] | $N^2$-(tert-butyl)-$N^8$-((4-phenylthiazol-5-yl)methyl)-5-(3-(trifluoromethyl)phenyl)-3,4-dihydroisoquinoline-2,8(1H)-dicarboxamide | 593.15 |

TABLE 2-continued

| Ex. # | Structure | Name | MS |
|---|---|---|---|
| 40 | 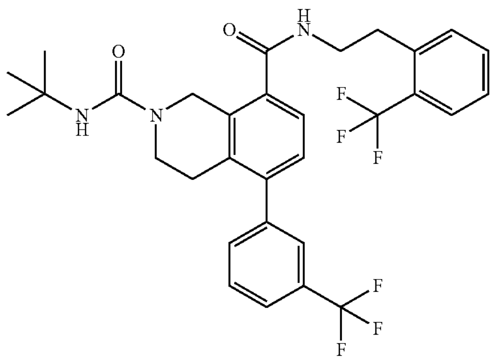 [SMILES: CC(C)(C)NC(=O)N1CCc2c(-c3cccc(C(F)(F)F)c3)ccc(C(=O)NCCc3ccccc3C(F)(F)F)c2C1] | $N^2$-(tert-butyl)-$N^8$-(2-(trifluoromethyl)phenethyl)-5-(3-(trifluoromethyl)phenyl)-3,4-dihydroisoquinoline-2,8(1H)-dicarboxamide | 592.30 |
| 41 | 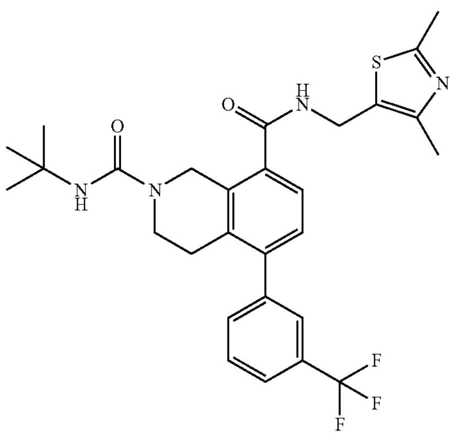 [SMILES: Cc1nc(C)c(CNC(=O)c2ccc(-c3cccc(C(F)(F)F)c3)c3c2CN(C(=O)NC(C)(C)C)CC3)s1] | $N^2$-(tert-butyl)-$N^8$-((2,4-dimethylthiazol-5-yl)methyl)-5-(3-(trifluoromethyl)phenyl)-3,4-dihydroisoquinoline-2,8(1H)-dicarboxamide | 545.18 |
| 42 | 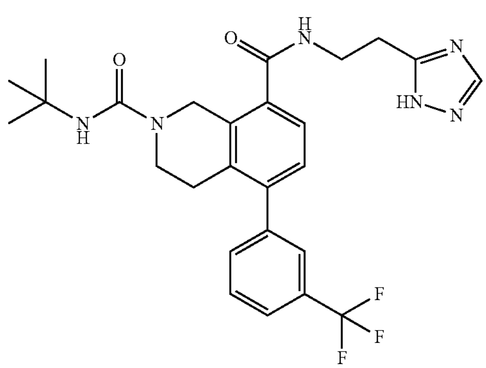 [SMILES: CC(C)(C)NC(=O)N1CCc2c(-c3cccc(C(F)(F)F)c3)ccc(C(=O)NCCc3ncn[nH]3)c2C1] | $N^8$-(2-(1H-1,2,4-triazol-5-yl)ethyl)-$N^2$-(tert-butyl)-5-(3-(trifluoromethyl)phenyl)-3,4-dihydroisoquinoline-2,8(1H)-dicarboxamide | 515.19 |
| 43 | 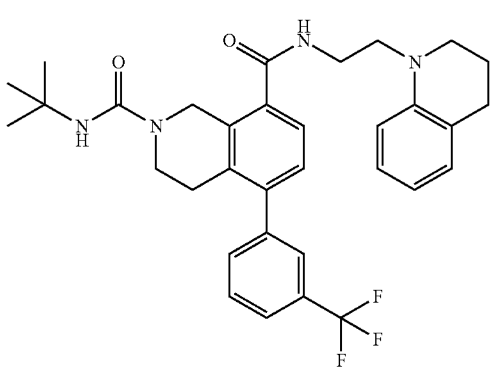 [SMILES: CC(C)(C)NC(=O)N1CCc2c(-c3cccc(C(F)(F)F)c3)ccc(C(=O)NCCN3CCCc4ccccc43)c2C1] | $N^2$-(tert-butyl)-$N^8$-(2-(3,4-dihydroquinolin-1(2H)-yl)ethyl)-5-(3-(trifluoromethyl)phenyl)-3,4-dihydroisoquinoline-2,8(1H)-dicarboxamide | 579.35 |

TABLE 2-continued

| Ex. # | Structure | Name | MS |
|---|---|---|---|
| 44 | 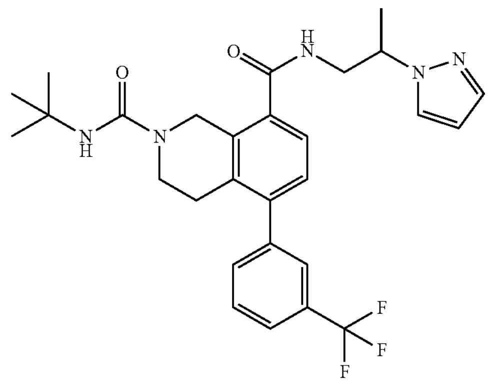 [SMILES: CC(CNC(=O)c1ccc(-c2cccc(C(F)(F)F)c2)c2c1CN(C(=O)NC(C)(C)C)CC2)n1cccn1] | $N^8$-(2-(1H-pyrazol-1-yl)propyl)-$N^2$-(tert-butyl)-5-(3-(trifluoromethyl)phenyl)-3,4-dihydroisoquinoline-2,8(1H)-dicarboxamide | 528.20 |
| 45 | 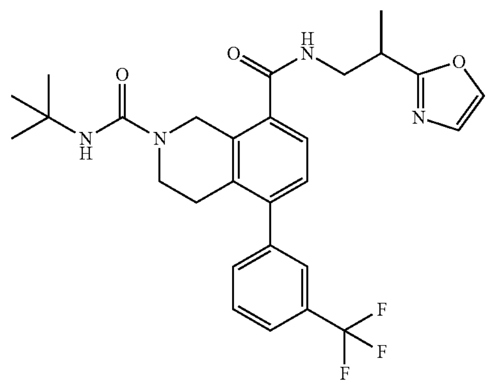 [SMILES: CC(CNC(=O)c1ccc(-c2cccc(C(F)(F)F)c2)c2c1CN(C(=O)NC(C)(C)C)CC2)c1ncco1] | $N^2$-(tert-butyl)-$N^8$-(2-(oxazol-2-yl)propyl)-5-(3-(trifluoromethyl)phenyl)-3,4-dihydroisoquinoline-2,8(1H)-dicarboxamide | 529.18 |
| 46 | 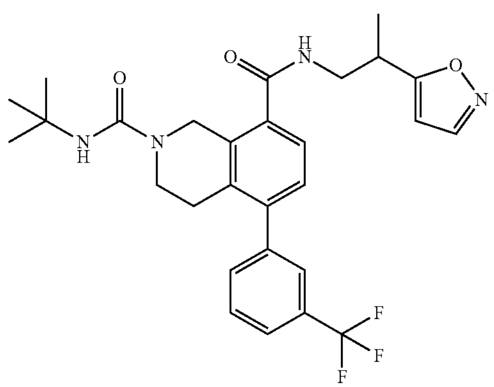 [SMILES: CC(CNC(=O)c1ccc(-c2cccc(C(F)(F)F)c2)c2c1CN(C(=O)NC(C)(C)C)CC2)c1ccno1] | $N^2$-(tert-butyl)-$N^8$-(2-(isoxazol-5-yl)propyl)-5-(3-(trifluoromethyl)phenyl)-3,4-dihydroisoquinoline-2,8(1H)-dicarboxamide | 529.19 |
| 47 | 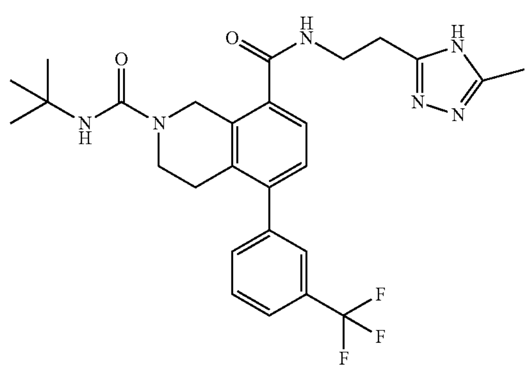 [SMILES: Cc1nnc(CCNC(=O)c2ccc(-c3cccc(C(F)(F)F)c3)c3c2CN(C(=O)NC(C)(C)C)CC3)[nH]1] | $N^2$-(tert-butyl)-$N^8$-(2-(5-methyl-4H-1,2,4-triazol-3-yl)ethyl)-5-(3-(trifluoromethyl)phenyl)-3,4-dihydroisoquinoline-2,8(1H)-dicarboxamide | 529.20 |

TABLE 2-continued

| Ex. # | Structure | Name | MS |
|---|---|---|---|
| 48 | 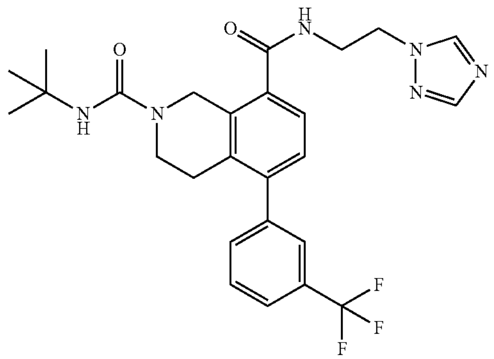 [SMILES: CC(C)(C)NC(=O)N1CCc2c(-c3cccc(C(F)(F)F)c3)ccc(C(=O)NCCn3cncn3)c2C1] | $N^8$-(2-(1H-1,2,4-triazol-1-yl)ethyl)-$N^2$-(tert-butyl)-5-(3-(trifluoromethyl)phenyl)-3,4-dihydroisoquinoline-2,8(1H)-dicarboxamide | 515.18 |
| 49 | 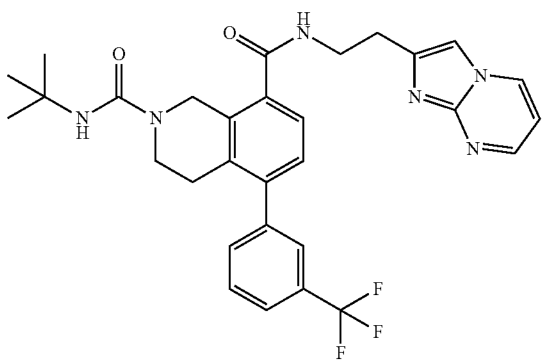 [SMILES: CC(C)(C)NC(=O)N1CCc2c(-c3cccc(C(F)(F)F)c3)ccc(C(=O)NCCc3cn4cccnc4n3)c2C1] | $N^2$-(tert-butyl)-$N^8$-(2-(imidazo[1,2-a]pyrimidin-2-yl)ethyl)-5-(3-(trifluoromethyl)phenyl)-3,4-dihydroisoquinoline-2,8(1H)-dicarboxamide | 565.31 |
| 50 | 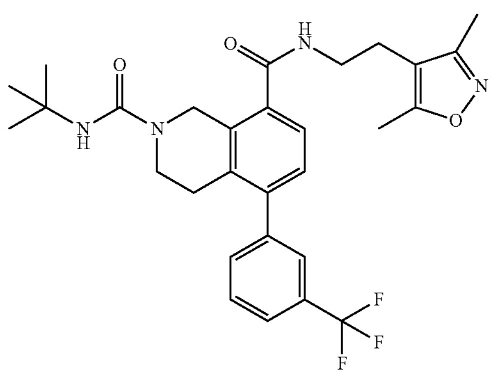 [SMILES: Cc1noc(C)c1CCNC(=O)c1ccc(-c2cccc(C(F)(F)F)c2)c2c1CN(C(=O)NC(C)(C)C)CC2] | $N^2$-(tert-butyl)-$N^8$-(2-(3,5-dimethylisoxazol-4-yl)ethyl)-5-(3-(trifluoromethyl)phenyl)-3,4-dihydroisoquinoline-2,8(1H)-dicarboxamide | 543.20 |
| 51 | 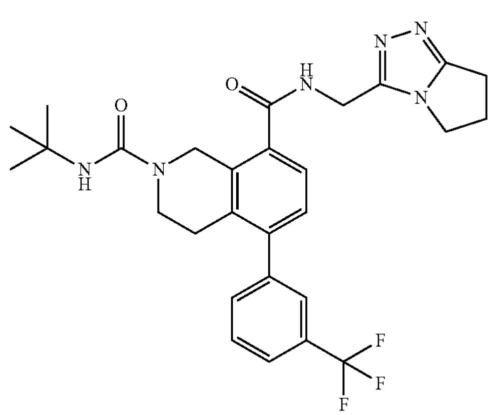 [SMILES: CC(C)(C)NC(=O)N1CCc2c(-c3cccc(C(F)(F)F)c3)ccc(C(=O)NCc3nnc4n3CCC4)c2C1] | $N^2$-(tert-butyl)-$N^8$-((6,7-dihydro-5H-pyrrolo[2,1-c][1,2,4]triazol-3-yl)methyl)-5-(3-(trifluoromethyl)phenyl)-3,4-dihydroisoquinoline-2,8(1H)-dicarboxamide | 541.19 |

TABLE 2-continued

| Ex. # | Structure | Name | MS |
|---|---|---|---|
| 52 | 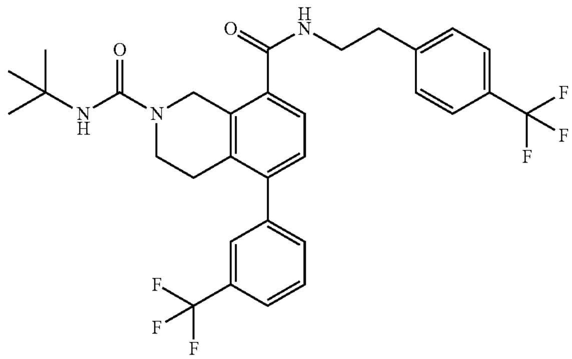 [SMILES: CC(C)(C)NC(=O)N1CCc2c(-c3cccc(C(F)(F)F)c3)ccc(C(=O)NCCc3ccc(C(F)(F)F)cc3)c2C1] | $N^2$-(tert-butyl)-$N^8$-(4-(trifluoromethyl)phenethyl)-5-(3-(trifluoromethyl)phenyl)-3,4-dihydroisoquinoline-2,8(1H)-dicarboxamide | 592.26 |
| 53 | 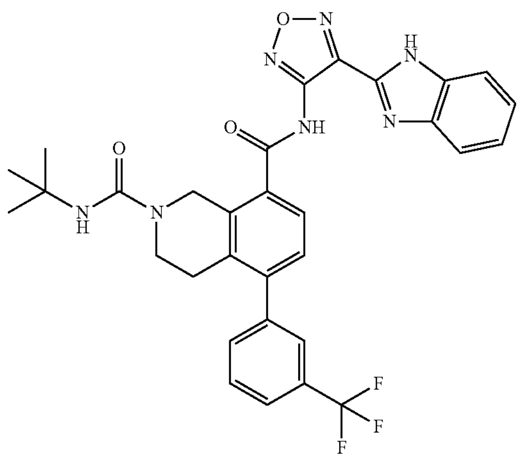 [SMILES: CC(C)(C)NC(=O)N1CCc2c(-c3cccc(C(F)(F)F)c3)ccc(C(=O)Nc3nonc3-c3nc4ccccc4[nH]3)c2C1] | $N^8$-(4-(1H-benzo[d]imidazol-2-yl)-1,2,5-oxadiazol-3-yl)-$N^2$-(tert-butyl)-5-(3-(trifluoromethyl)phenyl)-3,4-dihydroisoquinoline-2,8(1H)-dicarboxamide | 604.06 |
| 54 | 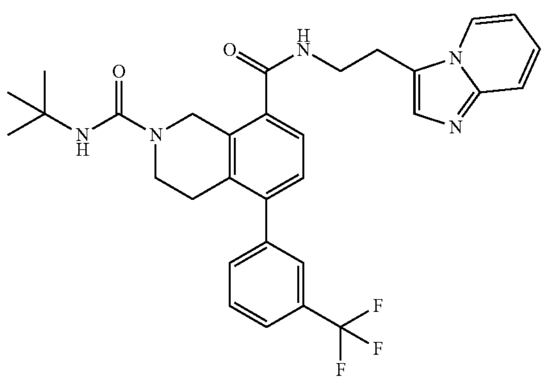 [SMILES: CC(C)(C)NC(=O)N1CCc2c(-c3cccc(C(F)(F)F)c3)ccc(C(=O)NCCc3cnc4ccccn34)c2C1] | $N^2$-(tert-butyl)-$N^8$-(2-(imidazo[1,2-a]pyridin-3-yl)ethyl)-5-(3-(trifluoromethyl)phenyl)-3,4-dihydroisoquinoline-2,8(1H)-dicarboxamide | 564.21 |
| 55 | 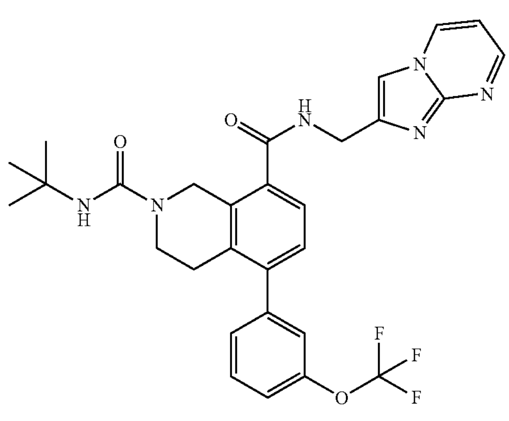 [SMILES: CC(C)(C)NC(=O)N1CCc2c(-c3cccc(OC(F)(F)F)c3)ccc(C(=O)NCc3cn4cccnc4n3)c2C1] | $N^2$-(tert-butyl)-$N^8$-(imidazo[1,2-a]pyrimidin-2-ylmethyl)-5-(3-(trifluoromethoxy)phenyl)-3,4-dihydroisoquinoline-2,8(1H)-dicarboxamide | 567.1 |

TABLE 2-continued

| Ex. # | Structure | Name | MS |
|---|---|---|---|
| 56 | 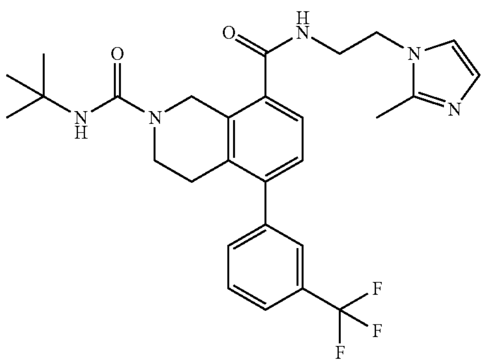 [SMILES: Cc1nccn1CCNC(=O)c1ccc(-c2cccc(C(F)(F)F)c2)c2c1CN(C(=O)NC(C)(C)C)CC2] | N²-(tert-butyl)-N⁸-(2-(2-methyl-1H-imidazol-1-yl)ethyl)-5-(3-(trifluoromethyl)phenyl)-3,4-dihydroisoquinoline-2,8(1H)-dicarboxamide | 528.21 |
| 57 | 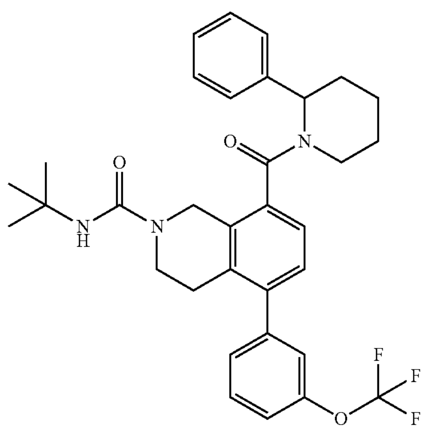 [SMILES: CC(C)(C)NC(=O)N1CCc2c(-c3cccc(OC(F)(F)F)c3)ccc(C(=O)N3CCCCC3c3ccccc3)c2C1] | N-(tert-butyl)-8-(2-phenylpiperidine-1-carbonyl)-5-(3-(trifluoromethoxy)phenyl)-3,4-dihydroisoquinoline-2(1H)-carboxamide | 580.23 |
| 58 | 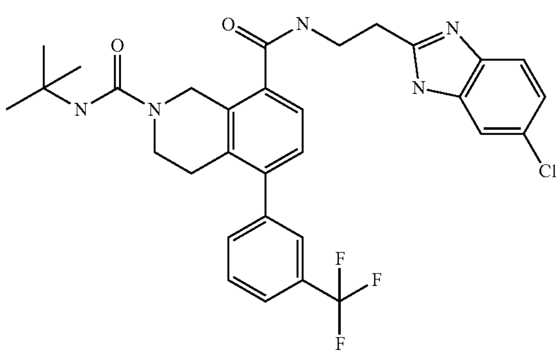 [SMILES: CC(C)(C)NC(=O)N1CCc2c(-c3cccc(C(F)(F)F)c3)ccc(C(=O)NCCc3nc4ccc(Cl)cc4[nH]3)c2C1] | N²-(tert-butyl)-N⁸-(2-(6-chloro-1H-benzo[d]imidazol-2-yl)ethyl)-5-(3-(trifluoromethyl)phenyl)-3,4-dihydroisoquinoline-2,8(1H)-dicarboxamide | 598.07 |
| 59 | 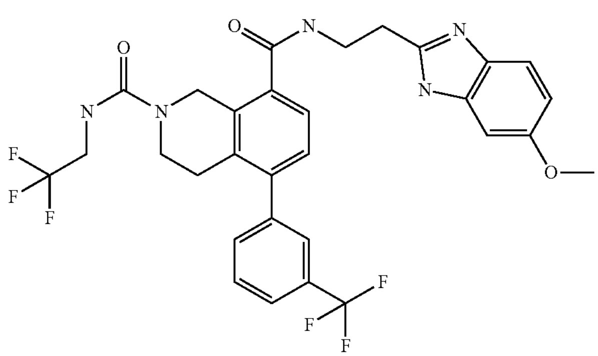 [SMILES: COc1ccc2nc(CCNC(=O)c3ccc(-c4cccc(C(F)(F)F)c4)c4c3CN(C(=O)NCC(F)(F)F)CC4)[nH]c2c1] | N⁸-(2-(6-methoxy-1H-benzo[d]imidazol-2-yl)ethyl)-N²-(2,2,2-trifluoroethyl)-5-(3-(trifluoromethyl)phenyl)-3,4-dihydroisoquinoline-2,8(1H)-dicarboxamide | 620.03 |

TABLE 2-continued

| Ex. # | Structure | Name | MS |
|---|---|---|---|
| 60 | 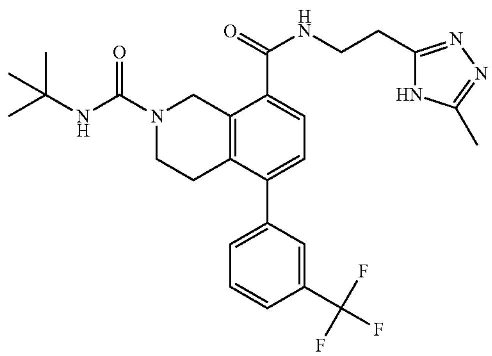 [SMILES: Cc1nnc(CCNC(=O)c2ccc(-c3cccc(C(F)(F)F)c3)c3c2CN(C(=O)NC(C)(C)C)CC3)[nH]1] | $N^2$-(tert-butyl)-$N^8$-(2-(5-methyl-4H-1,2,4-triazol-3-yl)ethyl)-5-(3-(trifluoromethyl)phenyl)-3,4-dihydroisoquinoline-2,8(1H)-dicarboxamide | 529.2 |
| 61 | 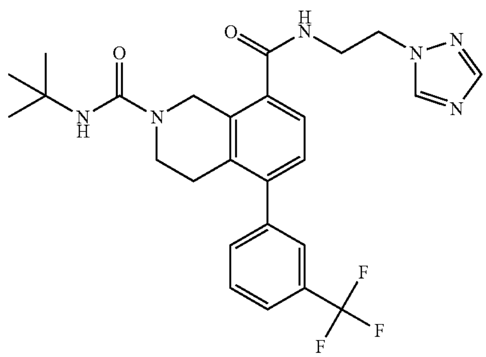 [SMILES: CC(C)(C)NC(=O)N1CCc2c(-c3cccc(C(F)(F)F)c3)ccc(C(=O)NCCn3cncn3)c2C1] | $N^8$-(2-(1H-1,2,4-triazol-1-yl)ethyl)-$N^2$-(tert-butyl)-5-(3-(trifluoromethyl)phenyl)-3,4-dihydroisoquinoline-2,8(1H)-dicarboxamide | 515.18 |
| 62 | 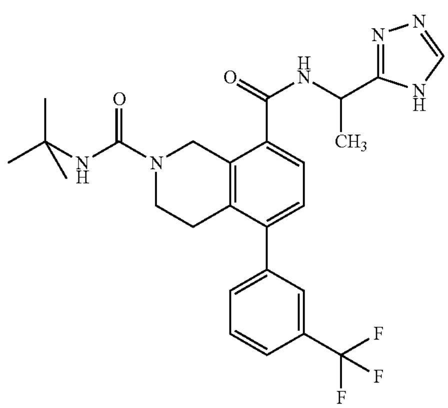 [SMILES: CC(NC(=O)c1ccc(-c2cccc(C(F)(F)F)c2)c2c1CN(C(=O)NC(C)(C)C)CC2)c1nnc[nH]1] | $N^8$-(1-(4H-1,2,4-triazol-3-yl)ethyl)-$N^2$-(tert-butyl)-5-(3-(trifluoromethyl)phenyl)-3,4-dihydroisoquinoline-2,8(1H)-dicarboxamide | 515.3 |
| 63 | 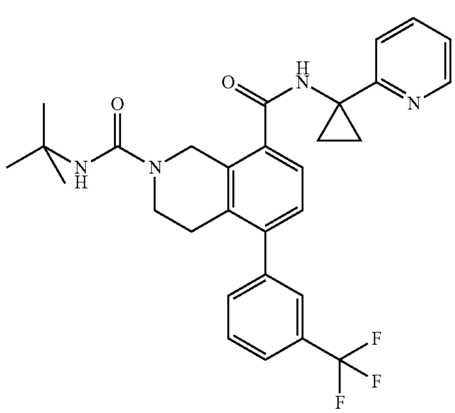 [SMILES: CC(C)(C)NC(=O)N1CCc2c(-c3cccc(C(F)(F)F)c3)ccc(C(=O)NC3(c4ccccn4)CC3)c2C1] | $N^2$-(tert-butyl)-$N^8$-(1-(pyridin-2-yl)cyclopropyl)-5-(3-(trifluoromethyl)phenyl)-3,4-dihydroisoquinoline-2,8(1H)-dicarboxamide | 537.3 |

TABLE 2-continued

| Ex. # | Structure | Name | MS |
|---|---|---|---|
| 64 | 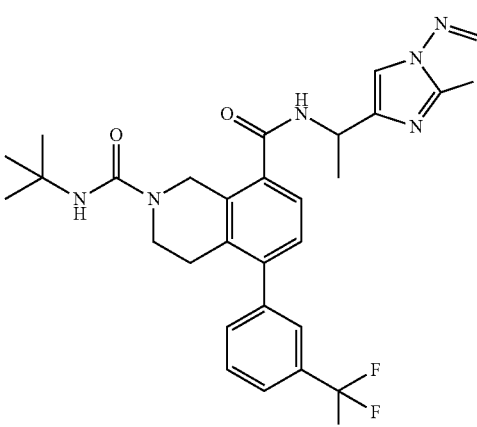 | N²-(tert-butyl)-N⁸-(1-(imidazo[2,1-b][1,3,4]thiadiazol-6-yl)ethyl)-5-(3-(trifluoromethyl)phenyl)-3,4-dihydroisoquinoline-2,8(1H)-dicarboxamide | 571.2 |
| 65 | 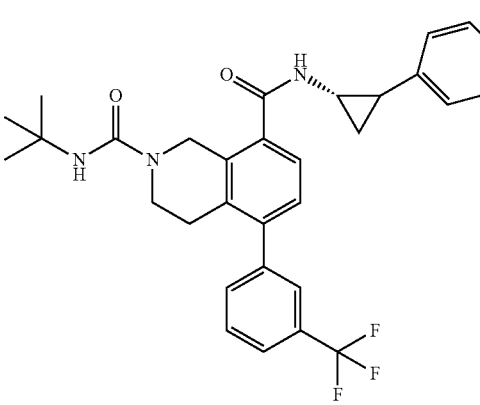 | N²-(tert-butyl)-N⁸-((trans)-2-phenylcyclopropyl)-5-(3-(trifluoromethyl)phenyl)-3,4-dihydroisoquinoline-2,8(1H)-dicarboxamide (mixture of 2 isomers) | 536.2 |
| 66 | 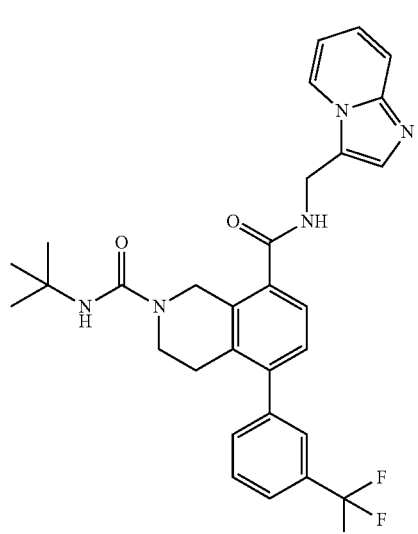 | N²-(tert-butyl)-N⁸-(imidazo[1,2-a]pyridin-3-ylmethyl)-5-(3-(trifluoromethyl)phenyl)-3,4-dihydroisoquinoline-2,8(1H)-dicarboxamide | 550.2 |

TABLE 2-continued

| Ex. # | Structure | Name | MS |
|---|---|---|---|
| 67 | 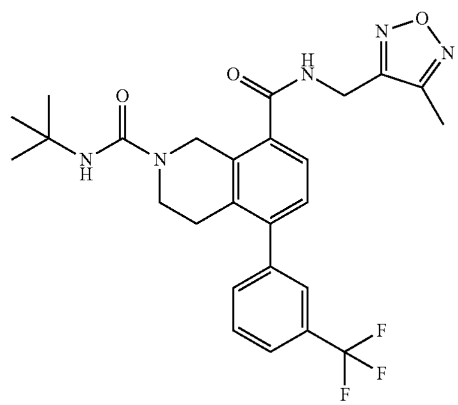 [SMILES: Cc1nonc1CNC(=O)c1ccc(-c2cccc(C(F)(F)F)c2)c2c1CN(C(=O)NC(C)(C)C)CC2] | $N^2$-(tert-butyl)-$N^8$-((4-methyl-1,2,5-oxadiazol-3-yl)methyl)-5-(3-(trifluoromethyl)phenyl)-3,4-dihydroisoquinoline-2,8(1H)-dicarboxamide | 516.2 |
| 68 | 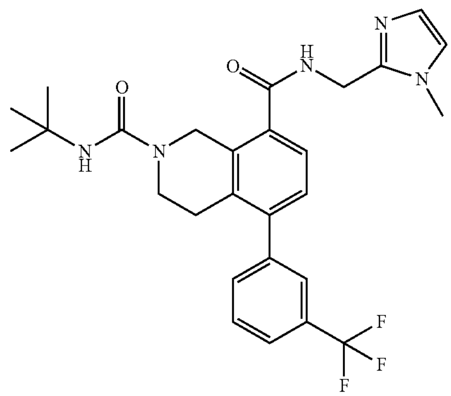 [SMILES: Cn1ccnc1CNC(=O)c1ccc(-c2cccc(C(F)(F)F)c2)c2c1CN(C(=O)NC(C)(C)C)CC2] | $N^2$-(tert-butyl)-$N^8$-((1-methyl-1H-imidazol-2-yl)methyl)-5-(3-(trifluoromethyl)phenyl)-3,4-dihydroisoquinoline-2,8(1H)-dicarboxamide | 514.2 |
| 69 | 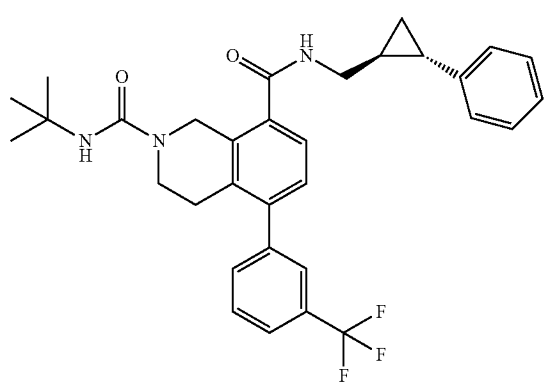 [SMILES: CC(C)(C)NC(=O)N1CCc2c(-c3cccc(C(F)(F)F)c3)ccc(C(=O)NC[C@H]3C[C@@H]3c3ccccc3)c2C1] | $N^2$-(tert-butyl)-$N^8$-(((trans)-2-phenylcyclopropyl)methyl)-5-(3-(trifluoromethyl)phenyl)-3,4-dihydroisoquinoline-2,8(1H)-dicarboxamide (mixture of 2 isomers) | 550.5 |
| 70 | 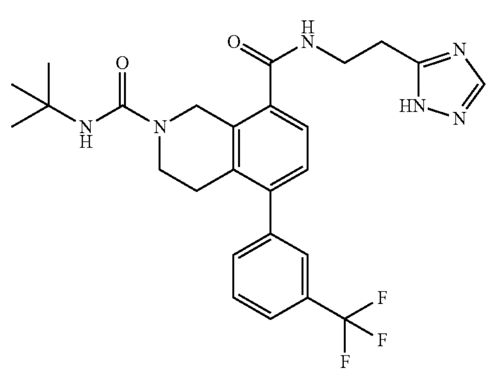 [SMILES: CC(C)(C)NC(=O)N1CCc2c(-c3cccc(C(F)(F)F)c3)ccc(C(=O)NCCc3ncn[nH]3)c2C1] | $N^8$-(2-(1H-1,2,4-triazol-5-yl)ethyl)-$N^2$-(tert-butyl)-5-(3-(trifluoromethyl)phenyl)-3,4-dihydroisoquinoline-2,8(1H)-dicarboxamide | 516.2 |

TABLE 2-continued

| Ex. # | Structure | Name | MS |
|---|---|---|---|
| 71 | 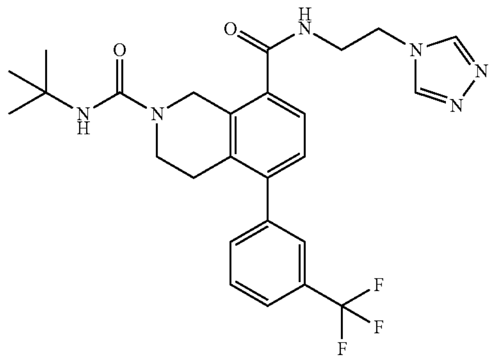 [SMILES: CC(C)(C)NC(=O)N1CCc2c(-c3cccc(C(F)(F)F)c3)ccc(C(=O)NCCn3cnnc3)c2C1] | $N^8$-(2-(4H-1,2,4-triazol-4-yl)ethyl)-$N^2$-(tert-butyl)-5-(3-(trifluoromethyl)phenyl)-3,4-dihydroisoquinoline-2,8(1H)-dicarboxamide | 515.2 |
| 72 | 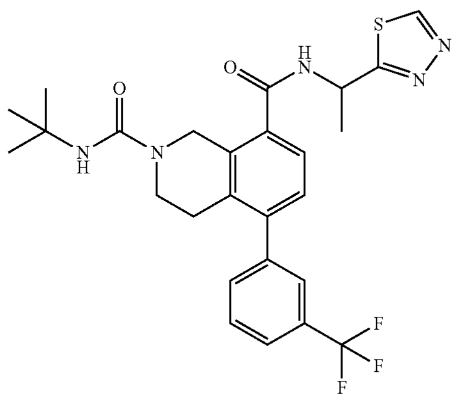 [SMILES: CC(NC(=O)c1ccc(-c2cccc(C(F)(F)F)c2)c2c1CN(C(=O)NC(C)(C)C)CC2)c1nncs1] | $N^8$-(1-(1,3,4-thiadiazol-2-yl)ethyl)-$N^2$-(tert-butyl)-5-(3-(trifluoromethyl)phenyl)-3,4-dihydroisoquinoline-2,8(1H)-dicarboxamide | 532.2 |
| 73 | 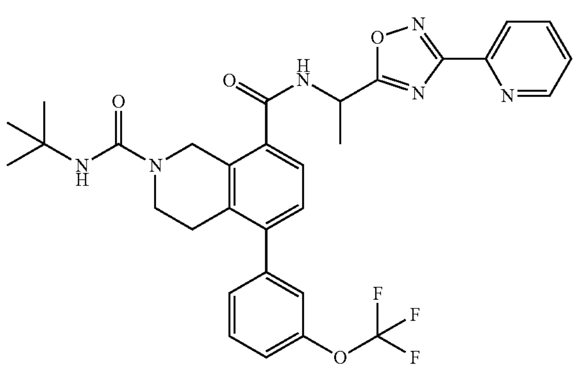 [SMILES: CC(NC(=O)c1ccc(-c2cccc(OC(F)(F)F)c2)c2c1CN(C(=O)NC(C)(C)C)CC2)c1nc(-c2ccccn2)no1] | $N^2$-(tert-butyl)-$N^8$-(1-(3-(pyridin-2-yl)-1,2,4-oxadiazol-5-yl)ethyl)-5-(3-(trifluoromethoxy)phenyl)-3,4-dihydroisoquinoline-2,8(1H)-dicarboxamide | 609.1 |
| 74 | 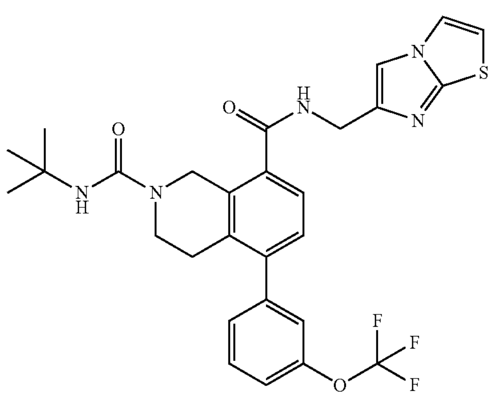 [SMILES: CC(C)(C)NC(=O)N1CCc2c(-c3cccc(OC(F)(F)F)c3)ccc(C(=O)NCc3cn4ccsc4n3)c2C1] | $N^2$-(tert-butyl)-$N^8$-(imidazo[2,1-b]thiazol-6-ylmethyl)-5-(3-(trifluoromethoxy)phenyl)-3,4-dihydroisoquinoline-2,8(1H)-dicarboxamide | 572.1 |

TABLE 2-continued

| Ex. # | Structure | Name | MS |
|---|---|---|---|
| 75 | 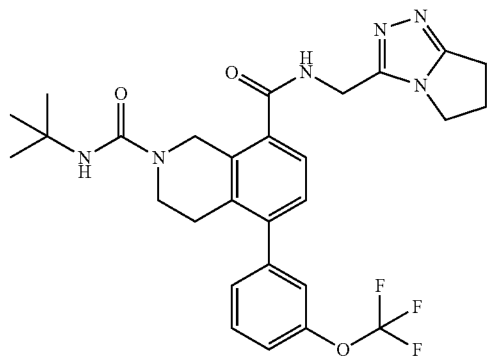 [SMILES: CC(C)(C)NC(=O)N1CCc2c(-c3cccc(OC(F)(F)F)c3)ccc(C(=O)NCc3nnc4n3CCC4)c2C1] | $N^2$-(tert-butyl)-$N^8$-((6,7-dihydro-5H-pyrrolo[2,1-c][1,2,4]triazol-3-yl)methyl)-5-(3-(trifluoromethoxy)phenyl)-3,4-dihydroisoquinoline-2,8(1H)-dicarboxamide | 557.3 |
| 76 | 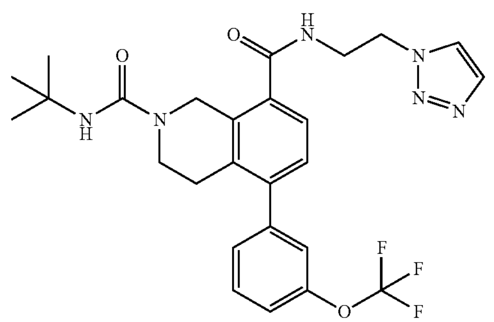 [SMILES: CC(C)(C)NC(=O)N1CCc2c(-c3cccc(OC(F)(F)F)c3)ccc(C(=O)NCCn3ccnn3)c2C1] | $N^8$-(2-(1H-1,2,3-triazol-1-yl)ethyl)-$N^2$-(tert-butyl)-5-(3-(trifluoromethoxy)phenyl)-3,4-dihydroisoquinoline-2,8(1H)-dicarboxamide | 531.2 |
| 77 | 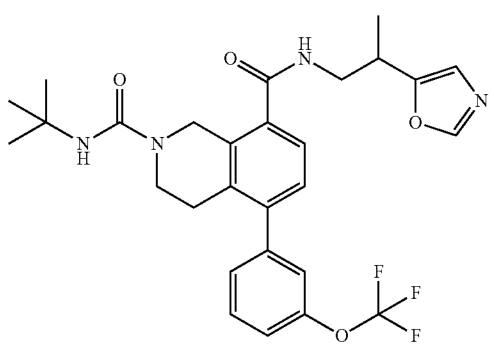 [SMILES: CC(CNC(=O)c1ccc(-c2cccc(OC(F)(F)F)c2)c2c1CN(C(=O)NC(C)(C)C)CC2)c1cnco1] | $N^2$-(tert-butyl)-$N^8$-(2-(oxazol-5-yl)propyl)-5-(3-(trifluoromethoxy)phenyl)-3,4-dihydroisoquinoline-2,8(1H)-dicarboxamide | 545.3 |
| 78 | 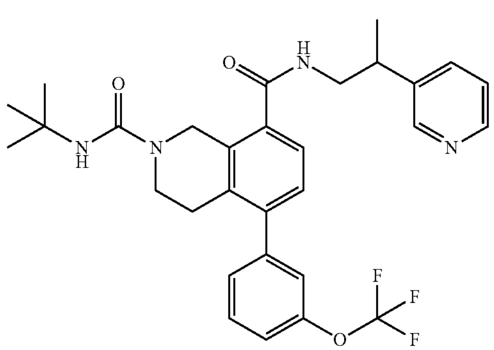 [SMILES: CC(CNC(=O)c1ccc(-c2cccc(OC(F)(F)F)c2)c2c1CN(C(=O)NC(C)(C)C)CC2)c1cccnc1] | $N^2$-(tert-butyl)-$N^8$-(2-(pyridin-3-yl)propyl)-5-(3-(trifluoromethoxy)phenyl)-3,4-dihydroisoquinoline-2,8(1H)-dicarboxamide | 555.3 |

TABLE 2-continued

| Ex. # | Structure | Name | MS |
|---|---|---|---|
| 79 | 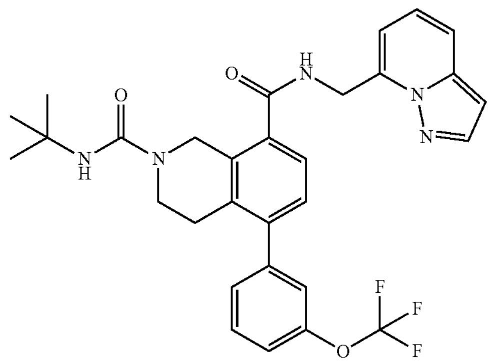 [SMILES: CC(C)(C)NC(=O)N1CCc2c(-c3cccc(OC(F)(F)F)c3)ccc(C(=O)NCc3cccc4ccnn34)c2C1] | N²-(tert-butyl)-N⁸-(pyrazolo[1,5-a]pyridin-7-ylmethyl)-5-(3-(trifluoromethoxy)phenyl)-3,4-dihydroisoquinoline-2,8(1H)-dicarboxamide | 566.1 |
| 80 | 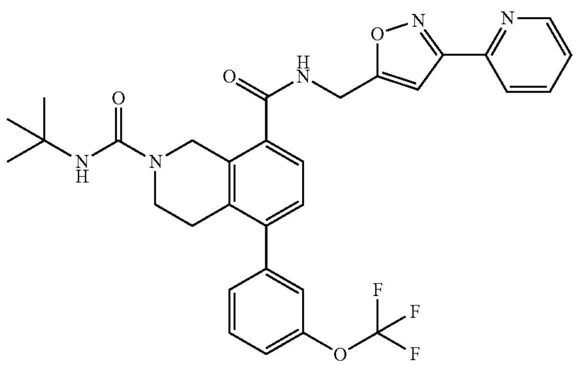 [SMILES: CC(C)(C)NC(=O)N1CCc2c(-c3cccc(OC(F)(F)F)c3)ccc(C(=O)NCc3cc(-c4ccccn4)no3)c2C1] | N²-(tert-butyl)-N⁸-((3-(pyridin-2-yl)isoxazol-5-yl)methyl)-5-(3-(trifluoromethoxy)phenyl)-3,4-dihydroisoquinoline-2,8(1H)-dicarboxamide | 594.1 |
| 81 | 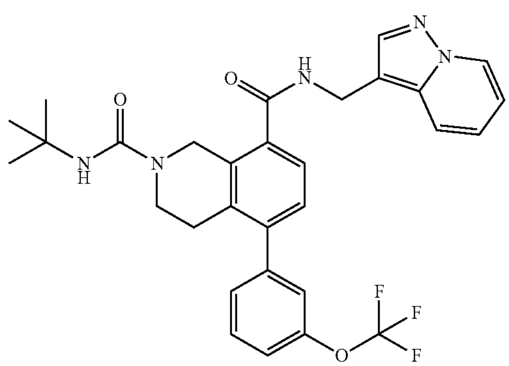 [SMILES: CC(C)(C)NC(=O)N1CCc2c(-c3cccc(OC(F)(F)F)c3)ccc(C(=O)NCc3cnn4ccccc34)c2C1] | N²-(tert-butyl)-N⁸-(pyrazolo[1,5-a]pyridin-3-ylmethyl)-5-(3-(trifluoromethoxy)phenyl)-3,4-dihydroisoquinoline-2,8(1H)-dicarboxamide | 566.1 |

ASSAYS

In Vitro DGAT2 ASSAYS and Determination of $IC_{50}$ Values for DGAT2 Inhibitors Insect Cell Expression and Membrane Preparation Sf-9 insect cells were maintained in Grace's insect cell culture medium with 10% heated-inactivated fetal bovine serum, 1% Pluronic F-68 and 0.14 µg/ml Kanamycine sulfate in Erlenmeyer flasks at 28° C. in a shaker incubator. After infection with untagged hDGAT2 baculovirus at multiplicity of infection (MOI) 0.1 for 48 hours, cells were harvested. Cell pellets were suspended in buffer containing 10 mM Tris-HCl (pH 7.5), 1 mM EDTA (pH 8.0), 250 mM sucrose and Complete Protease Inhibitor Cocktail (Roche Diagnostics Corp., Indianapolis, Ill.), and sonicated on ice. Membrane fractions were isolated by ultracentrifugation (100,000× g pellet), resuspended in the same buffer, and frozen (−80° C.) for later use. The protein concentration was determined with the BCA Protein Assay kit (Pierce Biotechnology Inc., Rockford, Ill.). Expression of protein levels was analyzed by immunoblotting with goat polyclonal DGAT2 antibody C-15 and donkey anti-goat IgG HRP (Santa Cruz Biotechnology, Inc., Santa Cruz, Calif.) followed by detection with ECL reagent (GE Healthcare, Piscataway, N.J.).

LC/MS/MS Analysis Method

LC/MS/MS analyses were performed using Thermal Fisher's LX4-TSQ Vantage system. This system consists of an Agilent binary high-performance liquid chromatography (HPLC) pumps and a TSQ Vantage triple quadrupole MS/MS instrument. For each sample, 2 µL samples from the top organic layer of in-plate liquid-liquid extraction were injected onto a Thermo Betabasic C4 column (2.1 mm×20 mm, 5 µm particle size). The samples were then eluted using the following conditions; mobile phase: methanol/water with 0.1% ammonium format=92/8 (v/v), flow rate: 1 mL/min, temperature: 25° C. Data was acquired in positive mode using a heated electrospray ionization (HESI) interface. The operational parameters for the TSQ Vantage MS/MS instrument were a spray voltage of 3000 V, capillary temperature of 280° C., vaporizer temperature 400° C., sheath gas 60 arbitrary unit, Aux gas 40 arbitrary units, S-lens 113 and collision gas 0.16 Pascals. Standard reference material (SRM) chromatograms of triolein (Q1: 902.9>Q3: 602.3) and internal standard (Q1: 902.9>Q3:602.3) were collected for 40 sec. The peak area was integrated by Xcalibur Quan software. The ratio between the triolein generated in the reaction and spiked in internal standard were used to generate percentage inhibition and IC50 values. Compound percentage inhibition was calculated by the following formula: Inhibition %=1−[(compound response−low control)/(high control−low control)]×100%. Potent compounds were titrated and IC50 were calculated by 4 parameter sigmoidal curve fitting formula.

DGAT2 Enzymatic Activity Assay

DGAT2 activity was determined by measuring the amount of enzymatic product triolein (1,2,3-Tri(cis-9-octadecenoyl) glycerol) using the membrane prep mentioned above. The assay was carried out in deep well 384 plates in a final volume of 40 µL at room temperature. The assay mixture contained the following: assay buffer (100 mM Tris·Cl, pH 7.0, 20 mM $MgCl_2$, 5% ethanol), 25 µM of diolein, 10 µM of oleoyl-CoA and 10 ng/µL of DGAT2 membrane.

TABLE 3

IC50 values for inhibition of DGAT2

| Ex. No. | IC50 (nM) |
|---|---|
| 1 | 1.75 |
| 2 | 103.6 |
| 3 | 17 |
| 4 | 41.43 |
| 5 | 134.7 |
| 6 | 11.9 |
| 7 | 15.88 |
| 8 | 32.89 |
| 9 | 51.09 |
| 10 | 66.9 |
| 11 | 67.64 |
| 12 | 68.58 |
| 13 | 68.93 |
| 14 | 102.9 |
| 15 | 120 |
| 16 | 126 |
| 17 | 131.7 |
| 18 | 133.1 |
| 19 | 197.2 |
| 20 | 204.7 |
| 21 | 214.1 |
| 22 | 235.1 |
| 23 | 243.7 |
| 24 | 265.3 |
| 25 | 271.1 |
| 26 | 291.7 |
| 27 | 314.5 |
| 28 | 326.1 |
| 29 | 329.3 |
| 30 | 350.8 |
| 31 | 504.7 |
| 32 | 538.8 |
| 33 | 588.2 |
| 34 | 664.5 |
| 35 | 727 |
| 36 | 737.2 |
| 37 | 739.4 |
| 38 | 853.6 |
| 39 | 889.5 |
| 40 | 905.4 |
| 41 | 906.8 |
| 42 | 959 |
| 43 | 1143 |
| 44 | 1203 |

TABLE 3-continued

IC50 values for inhibition of DGAT2

| Ex. No. | IC50 (nM) |
|---|---|
| 45 | 1282 |
| 46 | 1305 |
| 47 | 1203 |
| 48 | 1412 |
| 49 | 1574 |
| 50 | 1974 |
| 51 | 2027 |
| 52 | 2421 |
| 53 | 3336 |
| 54 | 3716 |
| 55 | 2149 |
| 56 | 7948 |
| 57 | 8755 |
| 58 | 16.72 |
| 59 | 82.9 |
| 60 | 1350 |
| 61 | 1412 |
| 62 | 3840 |
| 63 | 2059 |
| 64 | 390.4 |
| 65 | 1020 |
| 66 | 53.36 |
| 67 | 244.1 |
| 68 | 474.1 |
| 69 | 528.3 |
| 70 | 958.6 |
| 71 | 177.6 |
| 72 | 659.1 |
| 73 | 511.2 |
| 74 | 1543 |
| 75 | 2492 |
| 76 | 2584 |
| 77 | 867.1 |
| 78 | 1183 |
| 79 | 149.4 |
| 80 | 523.8 |
| 81 | 370 |

What is claimed is:

1. A compound having structural Formula I:

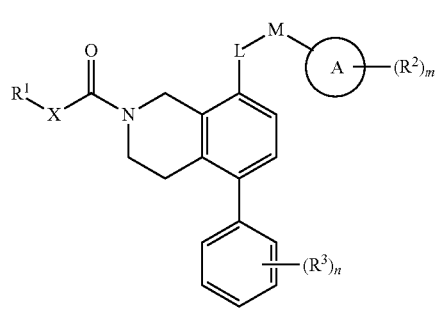

or a pharmaceutically acceptable salt thereof wherein:

L is
(1) —$CH_2$—, or
(2) —C(O)—;

M is
(1) —N($R^4$)—,
(2) *—N($R^4$)—($C_{1-3}$)alkylene wherein the alkylene is unsubstituted or substituted by ($C_{1-3}$)alkyl, hydroxy ($C_{1-3}$)alkyl, or morpholinyl,
(3) *—N($R^4$)—C(O)—,
(4) *—N($R^4$)—C(O)-heterocyclyl-, wherein the heterocyclyl is a 4- to 6-membered monocyclic ring containing 1-2 heteroatoms selected from the group consisting of N, O, and S,
(5) *—N($R^4$)—($C_{3-6}$)cycloalkyl-,
(6) *—N($R^4$)—($C_{1-2}$)alkyl-($C_{3-6}$)cycloalkyl-, or

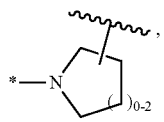

(7)
wherein * indicates the point of attachment to group L;
X is
(1) —O—, or
(2) —NH—;
$R^1$ is
(1) ($C_{1-6}$)alkyl,
(2) halo($C_{1-8}$)alkyl, or
(3) ($C_{3-6}$)cycloalkyl-;
ring A is
(1) 4- to 6-membered heterocyclyl containing 1-2 heteroatoms selected from the group consisting of N, O, and S,
(2) aryl,
(3) fused phenyl,
(4) 5- or 6-membered heteroaryl containing 1-4 heteroatoms selected from the group consisting of N, O, and S, or
(5) fused 8- to 10-membered heteroaryl containing 1-4 heteroatoms selected from the group consisting of N, O, and S;
$R^2$ is
(1) ($C_{1-6}$)alkyl,
(2) halo($C_{1-6}$)alkyl,
(3) ($C_{1-6}$)alkoxy,
(4) halo($C_{1-6}$)alkoxy,
(5) cyano,
(6) aryl,
(7) 5- or 6-membered heteroaryl containing 1-4 heteroatoms selected from the group consisting of N, O, or S,
(8) fused 8- to 10-membered heteroaryl containing 1-4 heteroatoms selected from the group consisting of N, O, and S,
(9) oxo,
(10) ($C_{3-6}$)cycloalkyl, or
(11) halo;
$R^3$ is
(1) ($C_{1-6}$)alkyl,
(2) halo($C_{1-6}$)alkyl,
(3) ($C_{1-6}$)alkoxy,
(4) halo($C_{1-6}$)alkoxy,
(5) —$CO_2$($C_{1-6}$)alkyl,
(6) halo, or
(7) hydroxy;

$R^4$ is
(1) hydrogen, or
(2) ($C_{1-3}$)alkyl;
m is 0, 1, 2, or 3; and
n is 0, 1 or 2.

2. The compound of claim 1 or a pharmaceutically acceptable salt thereof wherein L is —$CH_2$—.

3. The compound of claim 2 or a pharmaceutically acceptable salt thereof wherein M is *—N($R^4$)—C(O)—, or *—N($R^4$)—C(O)-heterocyclyl-, wherein the heterocyclyl is a 5- to 6-membered monocyclic ring containing 1-2 heteroatoms selected from the group consisting of N, O, and S; wherein * indicates the point of attachment to group L.

4. The compound of claim 3 or a pharmaceutically acceptable salt thereof wherein X is —NH—.

5. The compound of claim 1 or a pharmaceutically acceptable salt thereof wherein L is —C(O)—.

6. The compound of claim 5 or a pharmaceutically acceptable salt thereof wherein M is —N($R^4$)—; *—N($R^4$)—($C_{1-3}$)alkylene wherein the alkylene is unsubstituted or substituted by ($C_{1-3}$)alkyl, hydroxy($C_{1-3}$)alkyl or morpholinyl; *—N($R^4$)—($C_{3-6}$)cycloalkyl-; *—N($R^4$)—($C_{1-2}$)alkyl-($C_{3-6}$)cycloalkyl- or

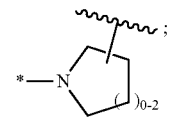

wherein * indicates the point of attachment to group L.

7. The compound of claim 6 or a pharmaceutically acceptable salt thereof wherein X is —NH—.

8. The compound of claim 1 or a pharmaceutically acceptable salt thereof wherein ring A is ring A is 5- or 6-membered heteroaryl containing 1-4 heteroatoms selected from the group consisting of N, O, and S or fused 8- to 10-membered heteroaryl containing 1-4 heteroatoms selected from the group consisting of N, O, and S.

9. The compound of claim 1 or a pharmaceutically acceptable salt thereof wherein ring A is pyrazolyl, isoquinolinyl, quinolinyl, imidazolyl, 1H-benzo[d]imidazolyl, imidazo[1,2-a]pyrimidinyl, imidazo[1,2-a]pyridinyl, benzo[c][1,2,5]oxadiazolyl, imidazo[2,1-b]thiazolyl, pyridinyl, 1,7-naphthyridinyl, imidazo[2,1-b][1,3,4]thiadiazolyl, isoxazolyl, 1,2,4-oxadiazolyl, isothiazolyl, pyrazolo[1,5-a]pyridinyl, 6,7-dihydro-5H-pyrrolo[2,1-c][1,2,4]triazolyl, 1H-benzo[d][1,2,3]triazolyl, 1,4,5,6-tetrahydrocyclopenta[c]pyrazolyl, 1H-1,2,3-triazolyl, pyrimidinyl, 1H-1,2,4-triazolyl, oxazolyl, or 1,2,5-oxadiazolyl.

10. The compound of claim 1 or a pharmaceutically acceptable salt thereof wherein ring A is aryl or fused phenyl.

11. The compound of claim 1, which is

---

1 methyl 3-(2-(tert-butylcarbamoyl)-8-((1-(4-(trifluoromethyl)phenyl)piperidine-4-carboxamido)methyl)-1,2,3,4-tetrahydroisoquinolin-5-yl)benzoate;
2 N-(tert-butyl)-5-(3-(trifluoromethoxy)phenyl)-8-((3-(trifluoromethyl)-1H-pyrazole-5-carboxamido)methyl)-3,4-dihydroisoquinoline-2(1H)-carboxamide;
3 methyl 3-(8-((3-(tert-butyl)-1-methyl-1H-pyrazole-5-carboxamido)methyl)-2-(tert-butylcarbamoyl)-1,2,3,4-tetrahydroisoquinolin-5-yl)benzoate;
4 N-(tert-butyl)-5-(3-methoxyphenyl)-8-((3-(trifluoromethyl)-1H-pyrazole-5-carboxamido)methyl)-3,4-dihydroisoquinoline-2(1H)-carboxamide;
5 N-((2-(tert-butylcarbamoyl)-5-(3-methoxyphenyl)-1,2,3,4-tetrahydroisoquinolin-8-yl)methyl)isoquinoline-1-carboxamide;

| | |
|---|---|
| 6 | $N^2$-(tert-butyl)-$N^8$-(2-(5-chloro-1H-benzo[d]imidazol-2-yl)ethyl)-5-(3-(trifluoromethyl)phenyl)-3,4-dihydroisoquinoline-2,8(1H)-dicarboxamide; |
| 7 | $N^2$-(tert-butyl)-$N^8$-(2-(5,6-dichloro-1H-benzo[d]imidazol-2-yl)ethyl)-5-(3-(trifluoromethyl)phenyl)-3,4-dihydroisoquinoline-2,8(1H)-dicarboxamide; |
| 8 | $N^2$-(tert-butyl)-$N^8$-(2-(5-fluoro-1H-benzo[d]imidazol-2-yl)ethyl)-5-(3-(trifluoromethyl)phenyl)-3,4-dihydroisoquinoline-2,8(1H)-dicarboxamide; |
| 9 | $N^8$-(2-(1H-benzo[d]imidazol-2-yl)ethyl)-$N^2$-(tert-butyl)-5-(3-(trifluoromethyl)phenyl)-3,4-dihydroisoquinoline-2,8(1H)-dicarboxamide; |
| 10 | $N^2$-(tert-butyl)-$N^8$-(isoquinolin-4-ylmethyl)-5-(3-(trifluoromethyl)phenyl)-3,4-dihydroisoquinoline-2,8(1H)-dicarboxamide; |
| 11 | $N^2$-(tert-butyl)-$N^8$-(quinolin-8-ylmethyl)-5-(3-(trifluoromethyl)phenyl)-3,4-dihydroisoquinoline-2,8(1H)-dicarboxamide; |
| 12 | $N^2$-(tert-butyl)-$N^8$-(isoquinolin-5-ylmethyl)-5-(3-(trifluoromethy)phenyl)-3,4-dihydroisoquinoline-2,8(1H)-dicarboxamide; |
| 13 | $N^2$-(tert-butyl)-$N^8$-(2-(6-methoxy-1H-benzo[d]imidazol-2-yl)ethyl)-5-(3-(trifluoromethoxy)phenyl)-3,4-dihydroisoquinoline-2,8(1H)-dicarboxamide; |
| 14 | $N^2$-(tert-butyl)-$N^8$-(2-(5-methyl-1H-benzo[d]imidazol-2-yl)ethyl)-5-(3-(trifluoromethyl)phenyl)-3,4-dihydroisoquinoline-2,8(1H)-dicarboxamide; |
| 15 | $N^2$-(tert-butyl)-$N^8$-((2-methylimidazo[1,2-a]pyridin-3-yl)methyl)-5-(3-(trifluoromethyl)phenyl)-3,4-dihydroisoquinoline-2,8(1H)-dicarboxamide; |
| 16 | N2-(tert-butyl)-$N^8$-(quinolin-5-ylmethyl)-5-(3-(trifluoromethyl)phenyl)-3,4-dihydroisoquinoline-2,8(1H)-dicarboxamide; |
| 17 | $N^8$-(benzo[c][l,2,5]oxadiazol-5-ylmethyl)-$N^2$-(tert-butyl)-5-(3-(trifluoromethyl)phenyl)-3,4-dihydroisoquinoline-2,8(1H)-dicarboxamide; |
| 18 | $N^2$-(tert-butyl)-$N^8$-(2-(imidazo[2,l-b]thiazol-6-yl)ethyl)-5-(3-(trifluoromethyl)phenyl)-3,4-dihydroisoquinoline-2,8(1H)-dicarboxamide; |
| 19 | $N^2$-(tert-butyl)-$N^8$-(isoquinolin-1-ylmethyl)-5-(3-(trifluoromethyl)phenyl)-3,4-dihydroisoquinoline-2,8(1H)-dicarboxamide; |
| 20 | $N^2$-(tert-butyl)-$N^8$-(2-(1-methyl-1H-benzo[d]imidazol-2-yl)ethyl)-5-(3-(trifluoromethyl)phenyl)-3,4-dihydroisoquinoline-2,8(1H)-dicarboxamide; |
| 21 | R)-$N^2$-(tert-butyl)-$N^8$-(2-hydroxy-1-(6-(trifluoromethyl)pyridin-3-yl)ethyl)-5-(3-(trifluoromethyl)phenyl)-3,4-dihydroisoquinoline-2,8(1H)-dicarboxamide; |
| 22 | $N^2$-(tert-butyl)-$N^8$-(isoquinolin-1-ylmethyl)-5-(3-(trifluoromethoxy)phenyl)-3,4-dihydroisoquinoline-2,8(1H)-dicarboxamide; |
| 23 | $N^2$-(tert-butyl)-$N^8$-(2-(imidazo[1,2-a]pyridin-2-yl)ethyl)-5-(3-(trifluoromethyl)phenyl)-3,4-dihydroisoquinoline-2,8(1H)-dicarboxamide; |
| 24 | $N^8$-((1,7-naphthyridin-8-yl)methyl)-$N^2$-(tert-butyl)-5-(3-(trifluoromethyl)phenyl)-3,4-dihydroisoquinoline-2,8(1H)-dicarboxamide; |
| 25 | $N^2$-(tert-butyl)-$N^8$-(2-(2-methylimidazo[2,1-b][1,3,4]thiadiazol-6-yl)ethyl)-5-(3-(trifluoromethyl)phenyl)-3,4-dihydroisoquinoline-2,8(1H)-dicarboxamide; |
| 26 | $N^2$-(tert-butyl)-$N^8$-(quinolin-4-ylmethyl)-5-(3-(trifluoromethyl)phenyl)-3,4-dihydroisoquinoline-2,8(1H)-dicarboxamide; |
| 27 | $N^2$-(tert-butyl)-$N^8$-((3-cyanoisoxazol-4-yl)methyl)-5-(3-(trifluoromethyl)phenyl)-3,4-dihydroisoquinoline-2,8(1H)-dicarboxamide; |
| 28 | $N^2$-(tert-butyl)-$N^8$-((5-phenyl-1,2,4-oxadiazol-3-yl)methyl)-5-)3-(trifluoromethyl)phenyl)-3,4-dihydroisoquinoline-2,8(1H)-dicarboxamide; |
| 29 | $N^2$-(tert-butyl)-$N^8$-(2-(thiazol-4-yl)ethyl)-5-(3-(trifluoromethyl)phenyl)-3,4-dihydroisoquinoline-2,8(1H)-dicarboxamide: |
| 30 | $N^2$-(tert-butyl)-$N^8$-(pyrazolo[1,5-a]pyridin-3-ylmethyl)-5-(3-(trifluoromethyl)phenyl)-3,4-dihydroisoquinoline-2,8(1H)-dicarboxamide; |
| 31 | $N^2$-(tert-butyl)-$N^8$-(2-(3,5-dimethyl-1H-pyrazol-1-yl)ethyl)-5-(3-(trifluoromethyl)phenyl)-3,4-dihydroisoquinoline-2,8(1H)-dicarboxamide; |
| 32 | $N^2$-(tert-butyl)-$N^8$-((5-methyl-2-phenylthiazol-4-yl)methyl)-5-(3-(trifluoromethyl)phenyl)-3,4-dihydroisoquinoline-2,8(1H)-dicarboxamide; |
| 33 | $N^2$-(tert-butyl)-$N^8$-((3-(pyridin-2-yl)-1,2,4-oxadiazol-5-yl)methyl)-5-(3-(trifluoromethyl)phenyl)-3,4-dihydroisoquinoline-2,8(1H)-dicarboxamide; |
| 34 | $N^8$-(2-(1H-benzo[d][1,2,3]triazol-1-yl)ethyl)-$N^2$-(tert-butyl)-5-(3-(trifluoromethyl)phenyl)-3,4-dihydroisoquinoline-2,8(1H)-dicarboxamide; |
| 35 | $N^2$-(tert-butyl)-$N^8$-((1,4,5,6-tetrahydrocyclopenta[c]pyrazol-3-yl)methyl)-5-(3-(trifluoromethyl)phenyl)-3,4-dihydroisoquinoline-2,8(1H)-dicarboxamide; |
| 36 | $N^2$-(tert-butyl)-$N^8$-(2-morpholino-2-(pyridin-2-yl)ethyl)-5-(3-(trifluoromethyl)phenyl)-3,4-dihydroisoquinoline-2,8(1H)-dicarboxamide; |
| 37 | $N^2$-(tert-butyl)-$N^8$-(2-(5-phenyl-1H-1,2,3-triazol-1-yl)ethyl)-5-(3-(trifluoromethyl)phenyl)-3,4-dihydroisoquinoline-2,8(1H)-dicarboxamide; |
| 38 | $N^2$-(tert-butyl)-$N^8$-(2-(4-methyl-6-(trifluoromethyl)pyrimidin-2-yl)ethyl)-5-(3-(trifluoromethyl)phenyl)-3,4-dihydroisoquinoline-2,8(1H)-dicarboxamide; |
| 39 | $N^2$-(tert-butyl)-$N^8$-((4-phenylthiazol-5-yl)methyl)-5-(3-(trifluoromethyl)phenyl)-3,4-dihydroisoquinoline-2,8(1H)-dicarboxamide; |
| 40 | $N^2$-(tert-butyl)-$N^8$-(2-(trifluoromethyl)phenethyl)-5-(3-(trifluoromethyl)phenyl)-3,4-dihydroisoquinoline-2,8(1H)-dicarboxamide; |
| 41 | $N^2$-(tert-butyl)-$N^8$-((2,4-dimethylthiazol-5-yl)methyl)-5-(3-(trifluoromethyl)phenyl)-3,4-dihydroisoquinoline-2,8(1H)-dicarboxamide; |
| 42 | $N^8$-(2-(1H-1,2,4-triazol-5-yl)ethyl)-$N^2$-(tert-butyl)-5-(3-(trifluoromethyl)phenyl)-3,4-dihydroisoquinoline-2,8(1H)-dicarboxamide; |
| 43 | $N^2$-(tert-butyl)-$N^8$-(2-(3,4-dihydroquinolin-1(2H)-yl)ethyl)-5-(3-(trifluoromethyl)phenyl)-3,4-dihydroisoquinoline-2,8(1H)-dicarboxamide; |
| 44 | $N^8$-(2-(1H-pyrazol-1-yl)propyl)-$N^2$-(tert-butyl)-5-(3-(trifluoromethyl)phenyl)-3,4-dihydroisoquinoline-2,8(1H)-dicarboxamide; |

-continued

45  $N^2$-(tert-butyl)-$N^8$-(2-(oxazol-2-yl)propyl)-5-(3-(trifluoromethyl)phenyl)-3,4-dihydroisoquinoline-2,8(1H)-dicarboxamide;
46  $N^2$-(tert-butyl)-$N^8$-(2-(isoxazol-5-yl)propyl)-5-(3-(trifluoromethyl)phenyl)-3,4-dihydroisoquinoline-2,8(1H)-dicarboxamide;
47  $N^2$-(tert-butyl)-$N^8$-(2-(5-methyl-4H-1,2,4-triazol-3-yl)ethyl)-5-(3-(trifluoromethyl)phenyl)-3,4-dihydroisoquinoline-2,8(1H)-dicarboxamide;
48  $N^8$-(2-(1H-1,2,4-triazol-1-yl)ethyl)-$N^2$-(tert-butyl)-5-(3-(trifluoromethyl)phenyl)-3,4-dihydroisoquinoline-2,8(1H)-dicarboxamide;
49  $N^2$-(tert-butyl)-$N^8$-(2-(imidazo[1,2-a]pyrimidin-2-yl)ethyl)-5-(3-(trifluoromethyl)phenyl)-3,4-dihydroisoquinoline-2,8(1H)-dicarboxamide;
50  $N^2$-(tert-butyl)-$N^8$-(2-(3,5-dimethylisoxazol-4-yl)ethyl)-5-(3-(trifluoromethyl)phenyl)-3,4-dihydroisoquinoline-2,8(1H)-dicarboxamide;
51  $N^2$-(tert-butyl)-$N^8$-((6,7-dihydro-5H-pyrrolo[2,1-c][1,2,4]triazol-3-yl)methyl)-5-(3-(trifluoromethyl)phenyl)-3,4-dihydroisoquinoline-2,8(1H)-dicarboxamide;
52  $N^2$-(tert-butyl)-$N^8$-(4-(trifluoromethyl)phenethyl)-5-(3-(trifluoromethyl)phenyl)-3,4-dihydroisoquinoline-2,8(1H)-dicarboxamide;
53  $N^8$-(4-(1H-benzo[d]imidazol-2-yl)-1,2,5-oxadiazol-3-yl)-$N^2$-(tert-butyl)-5-(3-(trifluoromethyl)phenyl)-3,4-dihydroisoquinoline-2,8(1H)-dicarboxamide;
54  $N^2$-(tert-butyl)-$N^8$-(2-(imidazo[1,2-a]pyridin-3-yl)ethyl)-5-(3-(trifluoromethyl)phenyl)-3,4-dihydroisoquinoline-2,8(1H)-dicarboxamide;
55  $N^2$-(tert-butyl)-$N^8$-(imidazo[1,2-a]pyrimidin-2-ylmethyl)-5-(3-(trifluoromethoxy)phenyl)-3,4-dihydroisoquinoline-2,8(1H)-dicarboxamide;
56  $N^2$-(tert-butyl)-$N^8$-(2-(2-methyl-1H-imidazol-1-yl)ethyl)-5-(3-(trifluoromethyl)phenyl)-3,4-dihydroisoquinoline-2,8(1H)-dicarboxamide;
57  N-(tert-butyl)-8-(2-phenylpiperidine-1-carbonyl)-5-(3-(trifluoromethoxy)phenyl)-3,4-dihydroisoquinoline-2(1H)-carboxamide;
58  $N^2$-(tert-butyl)-$N^8$-(2-(6-chloro-1H-benzo[d]imidazol-2-yl)ethyl)-5-(3-(trifluoromethyl)phenyl)-3,4-dihydroisoquinoline-2,8(1H)-dicarboxamide;
59  $N^8$-(2-(6-methoxy-1H-benzo[d]imidazol-2-yl)ethyl)-$N^2$-(2,2,2-trifluoroethyl)-5-(3-(trifluoromethyl)phenyl)-3,4-dihydroisoquinoline-2,8(1H)-dicarboxamide;
60  $N^2$-(tert-butyl)-$N^8$-(2-(5-methyl-4H-1,2,4-triazol-3-yl)ethyl)-5-(3-(trifluoromethyl)phenyl)-3,4-dihydroisoquinoline-2,8(1H)-dicarboxamide;
61  $N^8$-(2-(1H-1,2,4-triazol-1-yl)ethyl)-$N^2$-(tert-butyl)-5-(3-(trifluoromethyl)phenyl)-3,4-dihydroisoquinoline-2,8(1H)-dicarboxamide;
62  $N^8$-(1-(4H-1,2,4-triazol-3-yl)ethyl)-$N^2$-(tert-butyl)-5-(3-(trifluoromethyl)phenyl)-3,4-dihydroisoquinoline-2,8(1H)-dicarboxamide;
63  $N^2$-(tert-butyl)-$N^8$-(1-(pyridin-2-yl)cyclopropyl)-5-(3-(trifluoromethyl)phenyl)-3,4-dihydroisoquinoline-2,8(1H)-dicarboxamide;
64  $N^2$-(tert-butyl)-$N^8$-(1-(imidazo[2,1-b][1,3,4]thiadiazol-6-yl)ethyl)-5-(3-(trifluoromethyl)phenyl)-3,4-dihydroisoquinoline-2,8(1H)-dicarboxamide;
65  $N^2$-(tert-butyl)-$N^8$-((1R)-2-phenylcyclopropyl)-5-(3-(trifluoromethyl)phenyl)-3,4-dihydroisoquinoline-2,8(1H)-dicarboxamide;
67  $N^2$-(tert-butyl)-$N^8$-((4-methyl-1,2,5-oxadiazol-3-yl)methyl)-5-(3-(trifluoromethyl)phenyl)-3,4-dihydroisoquinoline-2,8(1H)-dicarboxamide;
68  $N^2$-(tert-butyl)-$N^8$-((1-methyl-1H-imidazol-2-yl)methyl)-5-(3-(trifluoromethyl)phenyl)-3,4-dihydroisoquinoline-2,8(1H)-dicarboxamide;
69  $N^2$-(tert-butyl)-$N^8$-(((1R,2R)-2-phenylcyclopropyl)methyl)-5-(3-(trifluoromethyl)phenyl)-3,4-dihydroisoquinoline-2,8(1H)-dicarboxamide;
70  $N^8$-(2-(1H-1,2,4-triazol-5-yl)ethyl)-$N^2$-(tert-butyl)-5-(3-(trifluoromethyl)phenyl)-3,4-dihydroisoquinoline-2,8(1H)-dicarboxamide;
71  $N^8$-(2-(4H-1,2,4-triazol-4-yl)ethyl)-$N^2$-(tert-butyl)-5-(3-(trifluoromethyl)phenyl)-3,4-dihydroisoquinoline-2,8(1H)-dicarboxamide;
72  $N^8$-(1-(1,3,4-thiadiazol-2-yl)ethyl)-$N^2$-(tert-butyl)-5-(3-(trifluoromethyl)phenyl)-3,4-dihydroisoquinoline-2,8(1H)-dicarboxamide;
73  $N^2$-(tert-butyl)-$N^8$-(1-(3-(pyridin-2-yl)-1,2,4-oxadiazol-5-yl)ethyl)-5-(3-(trifluoromethoxy)phenyl)-3,4-dihydroisoquinoline-2,8(1H)-dicarboxamide;
74  $N^2$-(tert-butyl)-$N^8$-(imidazo[2,1-b]thiazol-6-ylmethyl)-5-(3-(trifluoromethoxy)phenyl)-3,4-dihydroisoquinoline-2,8(1H)-dicarboxamide;
75  $N^2$-(tert-butyl)-$N^8$-((6,7-dihydro-5H-pyrrolo[2,1-c][1,2,4]triazol-3-yl)methyl)-5-(3-(trifluoromethoxy)phenyl)-3,4-dihydroisoquinoline-2,8(1H)-dicarboxamide;
76  $N^8$-(2-(1H-1,2,3-triazol-1-yl)ethyl)-$N^2$-(tert-butyl)-5-(3-(trifluoromethoxy)phenyl)-3,4-dihydroisoquinoline-2,8(1H)-dicarboxamide;
77  $N^2$-(tert-butyl)-$N^8$-(2-(oxazol-5-yl)propyl)-5-(3-(trifluoromethoxy)phenyl)-3,4-dihydroisoquinoline-2,8(1H)-dicarboxamide;
78  $N^2$-(tert-butyl)-$N^8$-(2-(pyridin-3-yl)propyl)-5-(3-(trifluoromethoxy)phenyl)-3,4-dihydroisoquinoline-2,8(1H)-dicarboxamide;
79  $N^2$-(tert-butyl)-$N^8$-(pyrazolo[1,5-a]pyridin-7-ylmethyl)-5-(3-(trifluoromethoxy)phenyl)-3,4-dihydroisoquinoline-2,8(1H)-dicarboxamide;
80  $N^2$-(tert-butyl)-$N^8$-((3-(pyridin-2-yl)isoxazol-5-yl)methyl)-5-(3-(trifluoromethoxy)phenyl)-3,4-dihydroisoquinoline-2,8(1H)-dicarboxamide; or
81  $N^2$-(tert-butyl)-$N^8$-(pyrazolo[1,5-a]pyridin-3-ylmethyl)-5-(3-(trifluoromethoxy)phenyl)-3,4-dihydroisoquinoline-2,8(1H)-dicarboxamide;

or a pharmaceutically acceptable salt thereof.

12. The compound of claim 1, which is 1. (R)-N²-(tert-butyl)-N⁸-(2-hydroxy-1-(6-(trifluoromethyl)pyridin-3-yl)ethyl)-5-(3-(trifluoromethyl)phenyl)-3,4-dihydroisoquinoline-2,8(1H)-dicarboxamide;
2. (S)-N²-(tert-butyl)-N⁸-(2-hydroxy-1-(6-(trifluoromethyl)pyridin-3-yl)ethyl)-5-(3-(trifluoromethyl)phenyl)-3,4-dihydroisoquinoline-2,8(1H)-dicarboxamide,
3. N²-(tert-butyl)-N⁸-((1R)-2-phenylcyclopropyl)-5-(3-(trifluoromethyl)phenyl)-3,4-dihydroisoquinoline-2,8(1H)-dicarboxamide,
4. N²-(tert-butyl)-N⁸-((1S,2R)-2-phenylcyclopropyl)-5-(3-(trifluoromethyl)phenyl)-3,4-dihydroisoquinoline-2,8(1H)-dicarboxamide,
5. N²-(tert-butyl)-N⁸-((1R,2S)-2-phenylcyclopropyl)-5-(3-(trifluoromethyl)phenyl)-3,4-dihydroisoquinoline-2,8(1H)-dicarboxamide,
6. N²-(tert-butyl)-N⁸-(((1R,2R)-2-phenylcyclopropyl)methyl)-5-(3-(trifluoromethyl)phenyl)-3,4-dihydroisoquinoline-2,8(1H)-dicarboxamide,
7. N²-(tert-butyl)-N⁸-(((1S,2S)-2-phenylcyclopropyl)methyl)-5-(3-(trifluoromethyl)phenyl)-3,4-dihydroisoquinoline-2,8(1H)-dicarboxamide,
8. N²-(tert-butyl)-N⁸-(imidazo[1,2-a]pyridin-3-ylmethyl)-5-(3-(trifluoromethyl)phenyl)-3,4-dihydroisoquinoline-2,8(1H)-dicarboxamide, or a pharmaceutically acceptable salt thereof.

13. The compound of claim 1, which is 1. (R/S)-N²-(tert-butyl)-N⁸-(2-hydroxy-1-(6-(trifluoromethyl)pyridin-3-yl)ethyl)-5-(3-(trifluoromethyl)phenyl)-3,4-dihydroisoquinoline-2,8(1H)-dicarboxamide,
2. N²-(tert-butyl)-N⁸-((trans)-2-phenylcyclopropyl)-5-(3-(trifluoromethyl)phenyl)-3,4-dihydroisoquinoline-2,8(1H)-dicarboxamide,
3. N²-(tert-butyl)-N⁸-(((trans)-2-phenylcyclopropyl)methyl)-5-(3-(trifluoromethyl)phenyl)-3,4-dihydroisoquinoline-2,8(1H)-dicarboxamide, or a pharmaceutically acceptable salt thereof.

14. A pharmaceutical composition comprising of the compound of claim 1, or a pharmaceutically acceptable salt thereof, and a pharmaceutically acceptable carrier.

15. A method of treating atherosclerosis, hepatic steatosis, atherosclerosis, type-2 diabetes mellitus, obesity, hyperlipidemia, or hypercholesterolemia in a patient in need of treatment comprising the administration to the patient of a therapeutically effective amount of a compound of claim 1, or a pharmaceutically acceptable salt thereof.

16. The method according to claim 15 for treating atherosclerosis.

* * * * *